US012111326B2

(12) United States Patent
Schubert et al.

(10) Patent No.: US 12,111,326 B2
(45) Date of Patent: *Oct. 8, 2024

(54) CARTRIDGE DEVICE FOR A MEASURING SYSTEM FOR MEASURING VISCOELASTIC CHARACTERISTICS OF A SAMPLE LIQUID, A CORRESPONDING MEASURING SYSTEM, AND A CORRESPONDING METHOD

(71) Applicant: C A Casyso GmbH, Basel (CH)

(72) Inventors: Axel Schubert, Munich (DE); Jose J. Romero-Galeano, Markt Schwaben (DE); Max Kessler, Munich (DE)

(73) Assignee: C A Casyso GmbH, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/212,002

(22) Filed: Jun. 20, 2023

(65) Prior Publication Data

US 2024/0027477 A1 Jan. 25, 2024

Related U.S. Application Data

(63) Continuation of application No. 17/831,845, filed on Jun. 3, 2022, now Pat. No. 11,768,211, which is a (Continued)

(51) Int. Cl.
*G01N 33/86* (2006.01)
*B01L 3/00* (2006.01)
(Continued)

(52) U.S. Cl.
CPC .............. *G01N 33/86* (2013.01); *B01L 3/502* (2013.01); *B01L 3/52* (2013.01); *G01N 11/00* (2013.01);
(Continued)

(58) Field of Classification Search
CPC ........ B01L 3/52; B01L 3/502; B01L 2200/10; B01L 2300/0636; B01L 2300/0861;
(Continued)

(56) References Cited

U.S. PATENT DOCUMENTS 2,555,937 A 6/1951 Rosenthal
2,995,425 A 8/1961 Fuhrmann
(Continued)

FOREIGN PATENT DOCUMENTS

AU 2011237383 10/2012
CN 1816306 8/2006
(Continued)

OTHER PUBLICATIONS

510(k) Substantial Equivalence Determination Decision Summary for ROTEM delta, FDA clearance No. K083842 (the "Decision Summary for ROTEM delta"), Mar. 23, 2010, 11 pages.
(Continued)

*Primary Examiner* — Paul M. West
(74) *Attorney, Agent, or Firm* — ArentFox Schiff LLP

(57) ABSTRACT

The present invention is directed to a cartridge device for a measuring system for measuring viscoelastic characteristics of a sample liquid, in particular a blood sample, comprising a cartridge body having at least one measurement cavity formed therein and having at least one probe element arranged in said at least one measurement cavity for performing a test on said sample liquid; and a cover being attachable on said cartridge body; wherein said cover covers at least partially said at least one measurement cavity and forms a retaining element for retaining said probe element in a predetermined position within said at least one measurement cavity. The invention is directed to a measurement system and a method for measuring viscoelastic characteristics of a sample liquid.

20 Claims, 13 Drawing Sheets

Related U.S. Application Data continuation of application No. 17/372,637, filed on Jul. 12, 2021, now Pat. No. 11,360,106, which is a continuation of application No. 17/182,502, filed on Feb. 23, 2021, now Pat. No. 11,061,038, which is a continuation of application No. 16/520,004, filed on Jul. 23, 2019, now Pat. No. 10,996,230, which is a continuation of application No. 16/146,333, filed on Sep. 28, 2018, now Pat. No. 10,746,750, which is a continuation of application No. 15/869,782, filed on Jan. 12, 2018, now abandoned, which is a continuation of application No. 15/357,492, filed on Nov. 21, 2016, now Pat. No. 9,915,671, which is a continuation of application No. 15/066,605, filed on Mar. 10, 2016, now Pat. No. 9,739,789, which is a continuation of application No. 13/895,034, filed on May 15, 2013, now Pat. No. 9,285,377, which is a continuation of application No. 12/640,376, filed on Dec. 17, 2009, now Pat. No. 8,448,499.

(60) Provisional application No. 61/140,344, filed on Dec. 23, 2008.

(51) Int. Cl.
*G01N 11/00* (2006.01)
*G01N 11/14* (2006.01)
*G01N 33/49* (2006.01)

(52) U.S. Cl.
CPC ......... *G01N 11/14* (2013.01); *G01N 33/4905* (2013.01); *B01L 2200/10* (2013.01); *B01L 2300/0627* (2013.01); *B01L 2300/0636* (2013.01); *B01L 2300/0861* (2013.01); *B01L 2300/087* (2013.01); *B01L 2400/0475* (2013.01); *G01N 2011/0046* (2013.01); *G01N 2333/96458* (2013.01); *G01N 2800/224* (2013.01)

(58) Field of Classification Search
CPC ....... B01L 2300/087; B01L 2400/0475; B01L 2300/0627; G01N 11/00; G01N 33/86; G01N 2011/0046; G01N 2333/96458; G01N 2800/224
See application file for complete search history.

(56) References Cited

U.S. PATENT DOCUMENTS

| | | |
|---|---|---|
| 3,714,815 A | 2/1973 | Hartert et al. |
| 3,803,903 A | 4/1974 | Lin |
| 3,903,903 A | 9/1975 | Matsumura |
| 4,112,740 A | 9/1978 | Brandestini |
| 4,148,216 A | 4/1979 | Do et al. |
| 4,193,293 A | 3/1980 | Cavallari |
| D260,428 S | 8/1981 | Fekete |
| 4,319,194 A | 3/1982 | Cardinal |
| 4,443,408 A | 4/1984 | Mintz |
| 4,558,589 A | 12/1985 | Hemmes et al. |
| 4,599,219 A | 7/1986 | Cooper |
| 4,671,939 A | 6/1987 | Mintz |
| 4,695,956 A | 9/1987 | Leveen et al. |
| 4,705,756 A | 11/1987 | Spillert et al. |
| 4,726,220 A | 2/1988 | Feier et al. |
| 4,752,449 A | 6/1988 | Jackson et al. |
| 4,753,776 A | 6/1988 | Hillman et al. |
| 4,756,884 A | 7/1988 | Hillman et al. |
| 4,765,180 A | 8/1988 | Clifton |
| 4,767,600 A | 8/1988 | Vicario |
| 4,814,247 A | 3/1989 | Spillert et al. |
| D302,294 S | 7/1989 | Hillman et al. |
| 4,849,340 A | 7/1989 | Oberhardt |
| 4,852,577 A | 8/1989 | Smith et al. |
| 4,868,129 A | 9/1989 | Gibbons et al. |
| D305,360 S | 1/1990 | Fechtner |
| 4,900,679 A | 2/1990 | Spillert et al. |
| 4,948,961 A | 8/1990 | Hillman et al. |
| 4,956,089 A | 9/1990 | Hurst |
| 4,963,498 A | 10/1990 | Hillman et al. |
| 5,009,316 A | 4/1991 | Klein |
| 5,016,469 A | 5/1991 | Henderson |
| 5,028,142 A | 7/1991 | Ostoich et al. |
| 5,056,357 A | 10/1991 | Dymling et al. |
| 5,077,017 A | 12/1991 | Gorin et al. |
| 5,091,304 A | 2/1992 | La Duca et al. |
| 5,104,813 A | 4/1992 | Besemer et al. |
| 5,104,975 A | 4/1992 | McCormick et al. |
| D327,743 S | 7/1992 | Frenkel |
| 5,162,237 A | 11/1992 | Messenger et al. |
| 5,164,598 A | 11/1992 | Hillman et al. |
| 5,169,786 A | 12/1992 | Caroll et al. |
| 5,204,525 A | 4/1993 | Hillman et al. |
| 5,205,159 A | 4/1993 | Carr, Jr. |
| 5,207,988 A | 5/1993 | Lucas |
| 5,222,808 A | 6/1993 | Sugarman et al. |
| 5,223,219 A | 6/1993 | Subramanian et al. |
| 5,223,227 A | 6/1993 | Zuckerman |
| 5,234,839 A | 8/1993 | McCormick et al. |
| 5,273,517 A | 12/1993 | Barone et al. |
| 5,287,732 A | 2/1994 | Sekiguchi |
| 5,300,779 A | 4/1994 | Hillman et al. |
| 5,302,348 A | 4/1994 | Cusack et al. |
| D347,067 S | 5/1994 | Shartle et al. |
| 5,311,908 A | 5/1994 | Barone et al. |
| 5,331,964 A | 7/1994 | Trahey et al. |
| 5,372,946 A | 12/1994 | Cusack et al. |
| 5,378,431 A | 1/1995 | Vogler et al. |
| 5,447,440 A | 9/1995 | Davis et al. |
| 5,473,536 A | 12/1995 | Wimmer |
| 5,487,387 A | 1/1996 | Trahey et al. |
| RE35,171 E | 3/1996 | McCormick et al. |
| 5,504,011 A | 4/1996 | Gavin et al. |
| 5,531,102 A | 7/1996 | Brookfield et al. |
| 5,534,226 A | 7/1996 | Gavin et al. |
| 5,602,037 A | 2/1997 | Ostgaard et al. |
| 5,605,154 A | 2/1997 | Ries et al. |
| 5,606,971 A | 3/1997 | Sarvazyan et al. |
| 5,628,961 A | 5/1997 | Davis et al. |
| 5,629,209 A | 5/1997 | Braun, Sr. et al. |
| 5,655,535 A | 8/1997 | Friemel et al. |
| 5,657,760 A | 8/1997 | Ying et al. |
| 5,660,993 A | 8/1997 | Cathey et al. |
| 5,673,699 A | 10/1997 | Trahey et al. |
| 5,731,212 A | 3/1998 | Gavin et al. |
| 5,744,898 A | 4/1998 | Smith et al. |
| 5,763,199 A | 6/1998 | Coller |
| 5,777,212 A | 7/1998 | Sekiguchi et al. |
| 5,777,215 A | 7/1998 | Calatzis et al. |
| 5,788,928 A | 8/1998 | Carey |
| 5,800,781 A | 9/1998 | Gavin et al. |
| 5,810,731 A | 9/1998 | Sarvazyan et al. |
| 5,854,005 A | 12/1998 | Coller |
| 5,854,076 A | 12/1998 | Kundu et al. |
| 5,854,423 A | 12/1998 | Venegas |
| 5,888,826 A | 3/1999 | Ostgaard et al. |
| 5,899,861 A | 5/1999 | Friemel et al. |
| 5,902,937 A | 5/1999 | Amrani et al. |
| 5,921,928 A | 7/1999 | Greenleaf et al. |
| 5,922,551 A | 7/1999 | Durbin et al. |
| 5,922,591 A | 7/1999 | Anderson et al. |
| 5,952,560 A | 9/1999 | Collings et al. |
| 6,012,712 A | 1/2000 | Bernstein |
| 6,016,712 A | 1/2000 | Warden et al. |
| 6,033,546 A | 3/2000 | Ramsey |
| 6,039,691 A | 3/2000 | Walker et al. |
| 6,046,051 A | 4/2000 | Jina |
| 6,066,243 A | 5/2000 | Anderson et al. |
| 6,083,159 A | 7/2000 | Driscoll, Jr. et al. |
| 6,114,135 A | 9/2000 | Goldstein |
| 6,117,081 A | 9/2000 | Jago et al. |
| 6,135,957 A | 10/2000 | Cohen-Bacrie et al. |

(56) References Cited

U.S. PATENT DOCUMENTS

| | | |
|---|---|---|
| 6,197,595 B1 | 3/2001 | Anderson et al. |
| 6,200,532 B1 | 3/2001 | Wu et al. |
| 6,213,950 B1 | 4/2001 | Cespedes et al. |
| 6,221,672 B1 | 4/2001 | Baugh et al. |
| RE37,171 E | 5/2001 | Busche et al. |
| 6,225,126 B1 | 5/2001 | Cohen et al. |
| 6,232,127 B1 | 5/2001 | Lans et al. |
| 6,242,267 B1 | 6/2001 | Herron et al. |
| 6,264,609 B1 | 7/2001 | Herrington et al. |
| 6,270,459 B1 | 8/2001 | Konofagou et al. |
| 6,277,074 B1 | 8/2001 | Chaturvedi et al. |
| 6,283,917 B1 | 9/2001 | Jago et al. |
| 6,318,191 B1 | 11/2001 | Chen |
| 6,371,912 B1 | 4/2002 | Nightingale et al. |
| 6,398,956 B1 | 6/2002 | Coville et al. |
| 6,402,704 B1 | 6/2002 | McMorrow |
| 6,403,381 B1 | 6/2002 | Mann et al. |
| 6,412,344 B1 | 7/2002 | Danicich et al. |
| 6,413,782 B1 | 7/2002 | Parce et al. |
| 6,429,025 B1 | 8/2002 | Parce et al. |
| 6,436,722 B1 | 8/2002 | Clark et al. |
| 6,448,024 B1 | 9/2002 | Bruegger |
| 6,451,610 B1 | 9/2002 | Gorman et al. |
| 6,454,714 B1 | 9/2002 | Ng et al. |
| 6,479,299 B1 | 11/2002 | Parce et al. |
| 6,494,834 B2 | 12/2002 | Konofagou et al. |
| 6,508,768 B1 | 1/2003 | Hall et al. |
| 6,514,204 B2 | 2/2003 | Alam et al. |
| 6,535,835 B1 | 3/2003 | Rubin et al. |
| 6,537,819 B2 | 3/2003 | Cohen et al. |
| 6,555,381 B2 | 4/2003 | Baugh et al. |
| 6,573,104 B2 | 6/2003 | Carr, Jr. et al. |
| 6,613,286 B2 | 9/2003 | Braun, Sr. et al. |
| 6,613,573 B1 | 9/2003 | Cohen |
| D481,133 S | 10/2003 | Blouin |
| 6,632,678 B2 | 10/2003 | Aiken et al. |
| D482,454 S | 11/2003 | Gebrian |
| 6,662,031 B1 | 12/2003 | Khalil et al. |
| 6,670,133 B2 | 12/2003 | Knapp et al. |
| 6,685,646 B2 | 2/2004 | Cespedes et al. |
| 6,687,625 B2 | 2/2004 | Srinivasan et al. |
| 6,692,439 B1 | 2/2004 | Walker et al. |
| 6,699,718 B1 | 3/2004 | Bruegger |
| 6,716,168 B2 | 4/2004 | Nock et al. |
| 6,726,629 B1 | 4/2004 | Frinking et al. |
| 6,750,053 B1 | 6/2004 | Opalsky |
| 6,764,448 B2 | 7/2004 | Trahey et al. |
| 6,787,363 B2 | 9/2004 | Cohen et al. |
| 6,797,519 B2 | 9/2004 | Cohen et al. |
| 6,830,936 B2 | 12/2004 | Anderson et al. |
| 6,838,055 B2 | 1/2005 | Sando et al. |
| 6,890,299 B2 | 5/2005 | Cohen et al. |
| 6,942,836 B2 | 9/2005 | Freudenthal et al. |
| 6,951,127 B1 | 10/2005 | Bi |
| 6,951,544 B2 | 10/2005 | Trahey et al. |
| 6,979,569 B1 | 12/2005 | Carver, Jr. et al. |
| 7,005,857 B2 | 2/2006 | Stiene et al. |
| 7,132,078 B2 | 11/2006 | Rawson et al. |
| 7,179,652 B2 | 2/2007 | Cohen et al. |
| 7,192,726 B1 | 3/2007 | Carr, Jr. et al. |
| 7,202,048 B2 | 4/2007 | Carr, Jr. |
| 7,205,115 B2 | 4/2007 | McHugh et al. |
| 7,207,939 B2 | 4/2007 | Husher |
| 7,247,488 B2 | 7/2007 | Ghai et al. |
| 7,258,411 B2 | 8/2007 | Parce et al. |
| 7,261,861 B2 | 8/2007 | Kautzky |
| 7,374,538 B2 | 5/2008 | Nightingale et al. |
| 7,399,637 B2 | 7/2008 | Wright et al. |
| 7,412,877 B1 | 8/2008 | Bi |
| 7,419,638 B2 | 9/2008 | Saltsman et al. |
| 7,422,905 B2 | 9/2008 | Clague et al. |
| 7,439,069 B2 | 10/2008 | Nippoldt et al. |
| 7,491,175 B2 | 2/2009 | Ruether et al. |
| 7,497,997 B2 | 3/2009 | Glezer et al. |
| 7,524,670 B2 | 4/2009 | Cohen et al. |
| 7,595,169 B2 | 9/2009 | Swaim et al. |
| 7,674,616 B2 | 3/2010 | Farnam, III et al. |
| 7,732,213 B2 | 6/2010 | Cohen et al. |
| 7,745,223 B2 | 6/2010 | Schubert et al. |
| 7,790,362 B2 | 9/2010 | Coller et al. |
| 7,811,792 B2 | 10/2010 | Cohen |
| 7,842,234 B2 | 11/2010 | Lauks et al. |
| 7,892,188 B2 | 2/2011 | Walker et al. |
| 7,897,114 B2 | 3/2011 | Poissy et al. |
| 7,901,629 B2 | 3/2011 | Calatzis et al. |
| 7,912,661 B2 | 3/2011 | Zeng et al. |
| 7,938,573 B2 | 5/2011 | Gau et al. |
| 7,939,288 B2 | 5/2011 | Wrabetz et al. |
| 7,947,505 B2 | 5/2011 | Kawasaki et al. |
| 7,951,606 B2 | 5/2011 | Pei et al. |
| 7,959,875 B2 | 6/2011 | Zhou et al. |
| 7,972,271 B2 | 7/2011 | Johnson et al. |
| 7,976,795 B2 | 7/2011 | Zhou et al. |
| 8,003,401 B2 | 8/2011 | Tonnessen et al. |
| D645,973 S | 9/2011 | Hoenes |
| 8,017,382 B2 | 9/2011 | Davis et al. |
| 8,058,023 B2 | 11/2011 | Gurbel |
| 8,062,883 B2 | 11/2011 | Woudenberg et al. |
| 8,067,226 B2 | 11/2011 | Woudenberg et al. |
| 8,084,272 B2 | 12/2011 | Campbell et al. |
| 8,110,392 B2 | 2/2012 | Battrell et al. |
| 8,168,442 B2 | 5/2012 | Petersen et al. |
| 8,202,492 B2 | 6/2012 | Linder et al. |
| 8,216,526 B2 | 7/2012 | Locascio et al. |
| 8,222,024 B2 | 7/2012 | Davis et al. |
| 8,238,182 B2 | 8/2012 | Bond et al. |
| 8,318,109 B2 | 11/2012 | Saltsman et al. |
| 8,372,343 B2 | 2/2013 | Goldstein |
| 8,377,392 B2 | 2/2013 | Miller et al. |
| 8,383,045 B2 | 2/2013 | Schubert et al. |
| 8,409,527 B2 | 4/2013 | Linder et al. |
| 8,431,413 B2 | 4/2013 | Dority et al. |
| 8,448,499 B2 | 5/2013 | Schubert et al. |
| 8,475,737 B2 | 7/2013 | Linder et al. |
| 8,548,759 B2 | 10/2013 | Walker et al. |
| 8,574,828 B2 | 11/2013 | Coller et al. |
| 8,591,448 B2 | 11/2013 | Powers et al. |
| 8,591,829 B2 | 11/2013 | Taylor et al. |
| 8,697,009 B2 | 4/2014 | Saltsman et al. |
| 8,709,787 B2 | 4/2014 | Handique |
| 8,740,818 B2 | 6/2014 | Walker et al. |
| 8,765,062 B2 | 7/2014 | Linder et al. |
| 8,802,445 B2 | 8/2014 | Linder et al. |
| 8,857,244 B2 | 10/2014 | Schubert et al. |
| 8,883,510 B2 | 11/2014 | Gehring et al. |
| 8,932,523 B2 | 1/2015 | Linder et al. |
| 9,061,280 B2 | 6/2015 | Tanaami et al. |
| 9,062,342 B2 | 6/2015 | Carrera Fabra et al. |
| 9,063,121 B2 | 6/2015 | Bru Gilbert et al. |
| 9,068,966 B2 | 6/2015 | Delmenico et al. |
| 9,075,047 B2 | 7/2015 | Linder et al. |
| 9,086,423 B2 | 7/2015 | Schubert et al. |
| 9,110,084 B2 | 8/2015 | Schubert et al. |
| D737,993 S | 9/2015 | Tan |
| 9,238,223 B2 | 1/2016 | Handique |
| 9,272,280 B2 | 3/2016 | Viola et al. |
| 9,285,377 B2 | 3/2016 | Schubert |
| 9,341,637 B2 | 5/2016 | Coller et al. |
| 9,354,243 B2 | 5/2016 | Chapman et al. |
| 9,410,971 B2 | 8/2016 | Viola et al. |
| 9,506,938 B2 | 11/2016 | Coller et al. |
| D777,343 S | 1/2017 | Gorin et al. |
| 9,739,789 B2 | 8/2017 | Schubert et al. |
| 9,915,671 B2 | 3/2018 | Schubert et al. |
| 9,977,039 B2 | 5/2018 | Viola et al. |
| 10,023,897 B2 | 7/2018 | Mori et al. |
| 10,031,144 B2 | 7/2018 | Viola et al. |
| 10,175,225 B2 | 1/2019 | McCluskey et al. |
| 10,481,168 B2 | 11/2019 | Viola et al. |
| 10,746,750 B2 | 8/2020 | Schubert et al. |
| 10,843,185 B2 | 11/2020 | Gorin et al. |
| 11,061,038 B2 | 7/2021 | Schubert et al. |
| 11,131,680 B2 | 9/2021 | Schubert et al. |
| 11,360,106 B2 | 6/2022 | Schubert et al. |

(56) References Cited

U.S. PATENT DOCUMENTS

| | | |
|---|---|---|
| 11,879,899 B2 | 1/2024 | Schubert et al. |
| 11,892,459 B2 | 2/2024 | Schubert et al. |
| 2001/0046685 A1 | 11/2001 | Moskowitz et al. |
| 2002/0013530 A1 | 1/2002 | Cespedes et al. |
| 2002/0040187 A1 | 4/2002 | Alam et al. |
| 2002/0081741 A1 | 6/2002 | Braun, Sr. |
| 2002/0177958 A1 | 11/2002 | Opalsky et al. |
| 2003/0013958 A1 | 1/2003 | Govari et al. |
| 2003/0073244 A1 | 4/2003 | Cohen et al. |
| 2003/0105398 A1 | 6/2003 | Vitek |
| 2003/0113929 A1 | 6/2003 | Baugh et al. |
| 2003/0170883 A1 | 9/2003 | Martin et al. |
| 2003/0171676 A1 | 9/2003 | Trahey et al. |
| 2003/0199082 A1 | 10/2003 | Miller |
| 2003/0204141 A1 | 10/2003 | Nock et al. |
| 2004/0053351 A1 | 3/2004 | Fischer et al. |
| 2004/0065143 A1 | 4/2004 | Husher |
| 2004/0068184 A1 | 4/2004 | Trahey et al. |
| 2004/0072278 A1 | 4/2004 | Chou et al. |
| 2004/0072357 A1 | 4/2004 | Stiene et al. |
| 2004/0076546 A1 | 4/2004 | Bissett |
| 2004/0088317 A1 | 5/2004 | Fabrick et al. |
| 2004/0089616 A1 | 5/2004 | Kellogg et al. |
| 2004/0131500 A1 | 7/2004 | Chow |
| 2004/0167403 A1 | 8/2004 | Nightingale et al. |
| 2004/0189311 A1 | 9/2004 | Glezer et al. |
| 2004/0203163 A1 | 10/2004 | Cohen et al. |
| 2004/0214337 A1 | 10/2004 | Kautzky |
| 2005/0004463 A1 | 1/2005 | Chen et al. |
| 2005/0015001 A1 | 1/2005 | Lee et al. |
| 2005/0053305 A1 | 3/2005 | Li et al. |
| 2005/0123447 A1 | 6/2005 | Koike et al. |
| 2005/0136541 A1 | 6/2005 | De Haan |
| 2005/0148899 A1 | 7/2005 | Walker et al. |
| 2005/0164373 A1 | 7/2005 | Oldham et al. |
| 2005/0215901 A1 | 9/2005 | Anderson et al. |
| 2005/0216987 P1 | 9/2005 | Murakami |
| 2005/0220668 A1 | 10/2005 | Coville |
| 2005/0233460 A1 | 10/2005 | Clague et al. |
| 2005/0233466 A1 | 10/2005 | Wright et al. |
| 2007/0038095 A1 | 2/2007 | Greenleaf et al. |
| 2007/0059208 A1 | 3/2007 | Desmond |
| 2007/0059840 A1 | 3/2007 | Cohen et al. |
| 2007/0078631 A1 | 4/2007 | Ariyoshi et al. |
| 2007/0099290 A1 | 5/2007 | Iida et al. |
| 2007/0105236 A1 | 5/2007 | Chang et al. |
| 2007/0140902 A1 | 6/2007 | Calatzis et al. |
| 2007/0184508 A1 | 8/2007 | Cohen et al. |
| 2007/0243105 A1 | 10/2007 | Kratzer et al. |
| 2007/0243632 A1 | 10/2007 | Coller et al. |
| 2007/0245810 A1 | 10/2007 | Carter et al. |
| 2007/0259348 A1 | 11/2007 | Phadke et al. |
| 2007/0266778 A1 | 11/2007 | Corey et al. |
| 2007/0276236 A1 | 11/2007 | Jong |
| 2008/0026476 A1 | 1/2008 | Howell |
| 2008/0038828 A1 | 2/2008 | Cohen et al. |
| 2008/0160500 A1 | 7/2008 | Fuller |
| 2008/0194041 A1 | 8/2008 | Guirguis |
| 2008/0194967 A1 | 8/2008 | Sliwa et al. |
| 2008/0200343 A1 | 8/2008 | Clemens |
| 2008/0227217 A1 | 9/2008 | Yamamoto et al. |
| 2008/0249408 A1 | 10/2008 | Palmeri et al. |
| 2008/0251383 A1 | 10/2008 | Sobek |
| 2008/0261261 A1 | 10/2008 | Grimes et al. |
| 2008/0280285 A1 | 11/2008 | Chen et al. |
| 2008/0297169 A1 | 12/2008 | Greenquist et al. |
| 2008/0299587 A1 | 12/2008 | Durbin |
| 2009/0112483 A1 | 4/2009 | Cohen |
| 2009/0130645 A1 | 5/2009 | Schubert et al. |
| 2009/0181411 A1 | 7/2009 | Battrell et al. |
| 2009/0269837 A1 | 10/2009 | Shevkoplyas et al. |
| 2009/0305315 A1 | 12/2009 | Gandola et al. |
| 2010/0056383 A1 | 3/2010 | Ririe et al. |
| 2010/0104474 A1 | 4/2010 | Van Haag et al. |
| 2010/0154520 A1 | 6/2010 | Schubert et al. |
| 2010/0184201 A1 | 7/2010 | Schubert et al. |
| 2010/0190193 A1 | 7/2010 | Calatzis et al. |
| 2010/0274130 A1 | 10/2010 | Anand et al. |
| 2011/0034805 A1 | 2/2011 | Walker et al. |
| 2011/0151491 A1 | 6/2011 | Dennis et al. |
| 2011/0172661 A1 | 7/2011 | Desinger et al. |
| 2011/0201099 A1 | 8/2011 | Anderson et al. |
| 2011/0237913 A1 | 9/2011 | Schubert et al. |
| 2011/0252352 A1 | 10/2011 | Viola et al. |
| 2012/0084022 A1 | 4/2012 | Giovangrandi et al. |
| 2012/0232803 A1 | 9/2012 | Viola et al. |
| 2012/0244392 A1 | 9/2012 | Kleiman |
| 2012/0252127 A1 | 10/2012 | Gregor et al. |
| 2012/0294767 A1 | 11/2012 | Viola |
| 2012/0329082 A1 | 12/2012 | Viola et al. |
| 2013/0137172 A1 | 5/2013 | Ririe et al. |
| 2013/0190584 A1 | 7/2013 | Walker et al. |
| 2013/0270113 A1 | 10/2013 | Huang |
| 2013/0323846 A1 | 12/2013 | Schubert et al. |
| 2013/0323847 A1 | 12/2013 | Schubert et al. |
| 2013/0323848 A1 | 12/2013 | Schubert et al. |
| 2013/0333448 A1 | 12/2013 | Schubert et al. |
| 2014/0004613 A1 | 1/2014 | Goldstein |
| 2014/0234859 A1 | 8/2014 | Coller et al. |
| 2014/0271409 A1 | 9/2014 | Knight |
| 2014/0328732 A1 | 11/2014 | Delmenico et al. |
| 2015/0253271 A1 | 9/2015 | Giridhar et al. |
| 2015/0260735 A1 | 9/2015 | Delmenico et al. |
| 2015/0316460 A1 | 11/2015 | Redl |
| 2016/0032355 A1 | 2/2016 | Zaman et al. |
| 2016/0091415 A1 | 3/2016 | Gorin |
| 2016/0091483 A1 | 3/2016 | McCluskey et al. |
| 2016/0091509 A1 | 3/2016 | Di Tullio et al. |
| 2016/0091511 A1 | 3/2016 | Di Tullio et al. |
| 2016/0091514 A1 | 3/2016 | Gorin et al. |
| 2016/0091515 A1 | 3/2016 | Gorin et al. |
| 2016/0091516 A1 | 3/2016 | Gorin |
| 2016/0091517 A1 | 3/2016 | Gorin |
| 2016/0139159 A1 | 5/2016 | Viola et al. |
| 2016/0195557 A1 | 7/2016 | Schubert |
| 2016/0313357 A1 | 10/2016 | Viola |
| 2016/0361715 A1 | 12/2016 | Shi et al. |
| 2016/0377638 A1 | 12/2016 | Bels et al. |
| 2017/0097367 A1 | 4/2017 | Schubert et al. |
| 2017/0254318 A1 | 9/2017 | Lee et al. |
| 2018/0133714 A1 | 5/2018 | Wo et al. |
| 2018/0306774 A1 | 10/2018 | Viola et al. |
| 2021/0172966 A1 | 6/2021 | Schubert et al. |
| 2021/0341499 A1 | 11/2021 | Schubert et al. |

FOREIGN PATENT DOCUMENTS

| | | |
|---|---|---|
| CN | 1853104 | 10/2006 |
| CN | 1985168 | 6/2007 |
| CN | 101035479 | 9/2007 |
| CN | 101195112 | 6/2008 |
| CN | 101301632 | 11/2008 |
| CN | 100540145 | 9/2009 |
| CN | 101563562 | 10/2009 |
| CN | 102265151 | 11/2011 |
| CN | 103170377 | 6/2013 |
| CN | 103175950 | 6/2013 |
| CN | 103217401 | 7/2013 |
| CN | 104204787 | 12/2014 |
| CN | 104903728 | 9/2015 |
| CN | 103649751 | 3/2017 |
| DE | 2740932 | 11/1978 |
| DE | 10135569 | 2/2003 |
| DE | 202014002289 | 9/2014 |
| EP | 0404456 | 12/1990 |
| EP | 1162457 | 12/2001 |
| EP | 1347058 | 9/2003 |
| EP | 1367392 | 12/2003 |
| EP | 1394546 | 3/2004 |
| EP | 1627725 | 2/2006 |
| EP | 1884778 | 2/2008 |
| EP | 1901065 | 3/2008 |
| EP | 2202517 | 6/2010 |
| EP | 2208996 | 7/2010 |

(56) References Cited

FOREIGN PATENT DOCUMENTS

| | | |
|---|---|---|
| EP | 2555704 | 2/2013 |
| EP | 2676143 | 12/2013 |
| EP | 3001196 | 3/2016 |
| GB | 2257256 | 1/1993 |
| JP | 1971-004947 | 11/1971 |
| JP | S5550162 | 4/1980 |
| JP | 1987-140047 | 6/1987 |
| JP | 1991-031764 | 2/1991 |
| JP | H04-32767 | 2/1992 |
| JP | H09-504372 | 4/1997 |
| JP | 1997-159596 | 6/1997 |
| JP | 1997-507580 | 7/1997 |
| JP | 2001-258868 | 9/2001 |
| JP | 2001-516880 | 10/2001 |
| JP | 2005-164296 | 6/2005 |
| JP | 2005-534895 | 11/2005 |
| JP | 2006-053142 | 2/2006 |
| JP | 2007517221 A | 6/2007 |
| JP | 2007-532878 | 11/2007 |
| JP | 2008-503722 | 2/2008 |
| JP | 2008-302322 | 12/2008 |
| JP | 2010-078575 | 4/2010 |
| JP | 2010-078608 | 8/2010 |
| JP | 2010-266453 | 11/2010 |
| JP | 2011-174952 | 9/2011 |
| JP | 2012-513582 | 6/2012 |
| JP | 2012-515340 | 7/2012 |
| JP | 2013-524176 | 6/2013 |
| JP | 2014-010109 | 1/2014 |
| JP | 2015-045642 | 3/2015 |
| JP | 2015-516583 | 6/2015 |
| JP | 2016-118530 | 6/2016 |
| WO | 1989006803 | 7/1989 |
| WO | 1996038730 | 12/1996 |
| WO | 1997041432 | 11/1997 |
| WO | 1999014595 | 3/1999 |
| WO | 2002050535 | 6/2002 |
| WO | 2002063273 | 8/2002 |
| WO | 2005026690 | 3/2005 |
| WO | 2005106467 | 11/2005 |
| WO | 2006091650 | 8/2006 |
| WO | 2006126290 | 11/2006 |
| WO | 2006137334 | 12/2006 |
| WO | 2007047961 | 4/2007 |
| WO | 2008075181 | 6/2008 |
| WO | 2008093216 | 8/2008 |
| WO | 2009073851 | 6/2009 |
| WO | 2009152094 | 12/2009 |
| WO | 2010072620 | 7/2010 |
| WO | 2011035162 | 3/2011 |
| WO | 2011117017 | 9/2011 |
| WO | 2011120556 | 10/2011 |
| WO | 2011127436 | 10/2011 |
| WO | 2012159021 | 11/2012 |
| WO | 2013105987 | 7/2013 |
| WO | 2013172003 | 11/2013 |
| WO | 2013173524 | 11/2013 |
| WO | 2014103744 | 7/2014 |
| WO | 2014115478 | 7/2014 |
| WO | 2014162285 | 10/2014 |
| WO | 2014172243 | 10/2014 |
| WO | 2015095658 | 6/2015 |
| WO | 2016196236 | 12/2016 |
| WO | 2017096284 | 6/2017 |

OTHER PUBLICATIONS

510(k) Summary for ROTEM delta, FDA clearance No. K083842 ("the 510 (k) Summary for ROTEM delta"), Mar. 23, 2010, 14 pages.
Alsberg et al., "Magnetically-guided self-assembly of fibrin matrices with ordered nano-scale structure for tissue engineering," Tissue Eng. Nov. 2006; 12(11):3247-56. DOI: 10.1089/ten.2006.12.3247. PMID: 17518638 [10 pages].
Americas Styrenics Styron® 666D Polystyrene; Dow Chemical, 2008. http://www.matweb.com/search/datasheet_print.aspx?matguid=dfc83225fec84437a9a3e9c7262badbe, (accessed Feb. 22, 2019) [3 pages].
Amukele et al., "Comparison of plasma with whole blood prothrombin time and fibrinogen on the same instrument," American Journal of Clinical Pathology, vol. 133, No. 4, pp. 550-556 (Apr. 2010) [7 pages].
Anderson, "Multi-Dimensional Velocity Estimation with Ultrasound Using Spatial Quadrature," IEEE Transactions on Ultrasonics Ferroelectrics & Frequency Control, vol. 45, No. 3, pp. 852-861 (1998) [10 pages].
Anderson, "Preventing Deep Vein Thrombosis and Pulmonary Embolism," Center for Outcomes Research, UMass Med Center, (1998) [33 pages].
Azar et al., "Abciximab in Primary Coronary Angioplasty for Acute Myocardial Infarction Improves Short- and Medium-Term Outcomes," J. Am. Coll. Cardiol. 32(7): 1996-2002. PubMed P.M.I.D.: 9857884 (Dec. 1998) [8 pages].
Becker, R., "Cell-based models of coagulation: a paradigm in evolution," Journal of Thrombosis and Thrombolysis, vol. 20, No. 1, pp. 65-68 (Aug. 2005) [4 pages].
Beer, A., "Thrombophilia: Inherited and Acquired," Center for Reproductive Immunology & Genetics, Retrieved Mar. 18, 2005 from URL: http://repro-med.net/papers/thromb.php [5 pages].
Bell et al., "Thrombelastographic evaluation of coagulation in transurethral prostatectomy," British Journal of Urology, vol. 78, No. 5, pp. 737-741 (1996) [10 pages].
Bercoff et al., "In vivo breast tumor detection using transient elastography," Ultrasound in Medicine & Biology, vol. 29, No. 10, pp. 1387-1396 (2003) [10 pages].
Bercoff et al., "Supersonic Shear Imaging: A New Technique for Soft Tissue Elasticity Mapping," IEEE Transactions on Ultrasonics Ferroelectrics & Frequency Control, vol. 51, No. 4, pp. 396-409 (2004) [14 pages].
Berney et al., "Impedance measurement monitors blood coagulation," Analog Dialogue 42-08, (2008) [3 pages].
Bilgen et al., "Error analysis in acoustic elastography. II. Strain estimation and SNR analysis," Journal of the Acoustical Society of America, vol. 101, pp. 1147-1154 (1997) [9 pages].
Blattler et al., "Effect of in vivo produced fibrinogenfibrin intermediates on viscosity of human blood," Thrombosis Research, vol. 4, iss. 6, pp. 787-801 (1974) [15 pages].
Bohs et al., "A Real Time System for Quantifying and Displaying Two-Dimensional Velocities using Ultrasound," Ultrasound in Medicine & Biology, vol. 19, No. 9, pp. 751-761 (Jul. 1993) [11 pages].
Bombeli et al., "Updates in perioperative coagulation: physiology and management of thromboembolism and haemorrhage," British Journal of Anesthesia; vol. 93, No. 2, pp. 275-287 (Aug. 2004) [13 pages].
Bonnefous et al., "Time Domain Formulation of Pulse-Doppler Ultrasound and Blood Velocity Estimation by Cross Correlation," Ultrasonic Imaging 8, pp. 73-85 (1986) [13 pages].
Born, G.V., "Aggregation of Blood Platelets by Adenosine Diphosphate and its Reversal," Nature, 194:927-9. PubMed P.M. I.D.: 13871375 (Jun. 9, 1962) [3 pages].
Brock et al., "Assessing Thrombin Generation at the Point of Care," Clinical Chemistry, vol. 55, No. 3, pp. 398-399 (Mar. 2009) [3 pages].
Calatzis et al., "Strategies to Assess Individual Susceptibility to Abciximab Therapy Using a New Functional Assay," Annals of Hematology, (Berlin, DE), vol. 76, No. Suppl 1, p. A61, XP009097526 (1998) [2 pages].
Calle et al., "Evaluation of the Sensitivity of an in vitro High Frequency Ultrasound Device to Monitor the Coagulation Process: Study of the Effects of Heparin Treatment in a Murine Model," Ultrasound Med. Biol. 36(2):295-305. PubMed P.M.I.D.: 20045589 (Feb. 2010) [11 pages].
Carr, M., "In vitro assessment of platelet function," Transfusion of Medicine Reviews, vol. 11, No. 2, pp. 106-115 (Apr. 1997) [10 pages].

(56) References Cited

OTHER PUBLICATIONS

Carroll et al., "Measurement of functional fibrinogen levels using the Thrombelastograph," Journal of Clinical Anesthesia, vol. 20, No. 3, pp. 186-190 (May 2008) [5 pages].
Carter, G., "Coherence and time delay estimation," Proc. IEEE, vol. 75, No. 2, pp. 236-255 (1987) [20 pages].
Celanese CoolPoly® E1201 Thermally Conductive Polypropylene; Cool Polymers, Inc., 2014. http://www.matweb.com/search/datasheet_print.aspx?matguid=fb2b886d487d4d15b0abc3d619930ed3, (accessed Feb. 22, 2019) [1 page].
Chakroun et al., "The Influence of Fibrin Polymerization and Platelet-Mediated Contractile Forces on Citrated Whole Blood Thromboelastography Profile," Thromb. Haemost. 95(5):822-828 (May 2006) [7 pages].
Chandler et al., "Development of a rapid emergency hemorrhage panel," Transfusion 50(12):2547-52, DOI: 10.1111/j.1537-2995.2010.02753.x (Dec. 2010) [6 pages].
Chandler et al., "Estimating the rate of thrombin and fibrin generation in vivo during cardiopulmonary bypass," Blood, vol. 101, No. 11, pp. 4355-4362 (Jun. 2003) [8 pages].
Chaturvedi et al., "Testing the limitations of 2-D companding for strain imaging using phantoms," IEEE Transactions on Ultrasonics Ferroelectrics & Frequency Control, vol. 45, pp. 1022-1031 (1998) [10 pages].
Chavez, J., "A novel thrombelaslograph tissue factor I kaolin assay of activated clotting times for monitoring heparin anticoagulation during cardiopulmonary bypass," Anesthesia and Analgesia; vol. 99, No. 5, pp. 1290-1294 (Nov. 2004) [5 pages].
Chonavel et al., "Fast adaptive eigenvalue decomposition: a maximum likelihood approach," Signal Processing, 83, pp. 307-324 (2003) [18 pages].
Cohn et al., "An elasticity microscope. Part I: Methods," IEEE Transactions on Ultrasonics Ferroelectrics & Frequency Control, vol. 44, pp. 1304-1319 (1997) [16 pages].
Cohn et al., "An elasticity microscope. Part II: Experimental Results," IEEE Transactions on Ultrasonics Ferroelectrics & Frequency Control, vol. 44, pp. 1320-1331 (1997) [12 pages].
Coiffic et al., "Inhibition of platelet aggregation by abciximab but not by aspirin can be detected by a new point-of-care test, the Hemostatus," Thromb. Res. 95(2), pp. 83-91 (1999) [9 pages].
Colman et al. (eds.), [Excerpt] Hemostasis and Thrombosis, Basic Principles and Clinical Practice. 3rd Edition. (J.B. Lippincott Company, Philadelphia). Ch. 1 "Overview of Hemostesis" by R.W. Colman, V.J. Marder, E.W. Salzman, J. Hirsh, (1994) [25 pages].
Craft et al., "A novel modification of the Thrombelaslograph assay, isolating platelet function, correlates with optical platelet aggregation," The Journal of Laboratory and Clinical Medicine, vol. 143, No. 5, pp. 301-309 (May 2004) [9 pages].
Crochemore et al., "A new era of thromboelastometry," Einstein (Sao Paulo). Jul.-Sep. 2017;15(3):380-385. DOI: 10.1590/S1679-45082017MD3130. Epub Jun. 12, 2017. PMID: 28614427; PMCID: PMC5823059 [6 pages].
Cuisset et al., "Clopidogrel response: Head-to-head comparison of different platelet assays to identify clopidogrel non-responder patients after coronary stenting," Archives of Cardiovascular Diseases. 2010; 103(1): 39-45 [7 pages].
Curry et al., "Convention and near-patient tests of coagulation," British Journal of Anesthesia, vol. 7, No. 2, pp. 45-50 (Apr. 2007) [6 pages].
Dahlback, B., "Blood Coagulation," Lancet, vol. 355, No. 9215, pp. 1627-1632 (May 2000) [6 pages].
Definition of "Cavity," Merriam-Webster's Collegiate Dictionary, (accessed Nov. 19, 2020) [3 pages].
Definition of "Duct," retrieved from Dictionary.com, for IPR2021-00293 of U.S. Pat. No. 10,746,750, filed Apr. 22, 2021 [8 pages].
Delhaye et al., "Temperature corrected thromboelastometry in hypothermic trauma patients: 6AP24," European Journal of Anaesthesiology 25:84 (May/ Jun. 2008) [1 page].
Despotis et al., "Monitoring of hemostasis in cardiac surgical patients: impact of point-of-care testing on blood loss and transfusion outcomes," Clinical Chemistry, vol. 43, No. 9, pp. 1684-1696 (Sep. 1997) [13 pages].
Dictionary.com online dictionary—cavity; ductwork; duct, of Request for Ex Parte Reexamination filed by a Third-Party Requester, Nov. 3, 2021 [21 pages].
Dorn-Beineke et al., "Evaluation of the Automated Coagulation Analyzer Sysmex CA—7000," Thromb. Res. 116(2):171-9. PubMed P.M.I.D.: 15907533 (2005) [9 pages].
Douning et al., "Temperature Corrected Thrombelastography in Hypothermic Patients," Anesthesia & Analgesia, Oct. 1995; 81(3): 608-611 [5 pages].
Eikelboom et al., "Monitoring Unfractionated Heparin with the aPTT: Time for a Fresh Look," Thromb. Haemost. 96 (5): 547-52. Review. PubMed P.M.I.D.: 17080209 (Nov. 2006) [6 pages].
Embree et al., "Volumetric Blood Flow via Time-Domain Correlation: Experimental Verification," IEEE Transactions on Ultrasonics Ferroelectrics & Frequency Control, vol. 37, No. 2, pp. 176-189 (May 1990) [14 pages].
Emelianov et al., "Ultrasound Elasticity Imaging of Deep Venous Thrombosis," Proc. IEEE Ultrasonics Symp., pp. 1791-1794 (2000) [4 pages].
Euroanaesthesia 2004: Joint Meeting of the European Society of Anaesthesiologists and European Academy of Anaesthesiology, Lisbon, Portugal, Jun. 5-8, 2004, European Journal of Anaesthesiology, 21(S32), DOI:10.1017/S0265021504000419 (2004) [228 pages].
Evans et al., "Rheometry and associated techniques for blood coagulation studies," Med Eng Phys. 30(6):671-9, DOI: 10.1016/j.medengphy.2007.08.005. Epub Sep. 27, 2007. PMID: 17900965 (Jul. 2008) [9 pages].
Fatemi et al., "Application of radiation force in non contact measurement of the elastic parameters," Ultrasonic Imaging, vol. 21, No. 2, pp. 147-154 (Apr. 1999) [8 pages].
Fatemi et al., "C-Scan Imaging by Radiation Force Stimulated Acoustic Emission Method," 1996 IEEE Ultrasonics Symposium. Proceedings, San Antonio, TX, USA, pp. 1459-1462 vol. 2, DOI: 10.1109/ULTSYM.1996.584341 (1996) [4 pages].
Fatemi et al., "Ultrasound-Stimulated Vibro-Acoustic Spectography," Science Magazine, vol. 280, No. 5360, pp. 82-85 (1998) [5 pages].
Faulds, D. et al., "Abciximab (c7E3 Fab). A review of its pharmacology and therapeutic potential in ischaemic heart disease," Drugs, 48(4), pp. 583-598. DOI: 10.2165/00003495-199448040-00007, PubMed P.M.I.D.: 7528131 ("Faulds 1994") (Oct. 1994) [2 pages].
Fayed et al., "Preoperative Thromboelastometry as a Predictor of Transfusion Requirements during Adult Living Donor Liver Transplantation," Transfus. Med. Hemother. 42(2):99-108, DOI: 10.1159/000381733 (2015) [10 pages].
Ferraris et al., "2011 Update to The Society of Thoracic Surgeons and the Society of Cardiovascular Anesthesiologists Blood Conservation Clinical Practice Guidelines," Annals of Thoracic Surgery, vol. 91, pp. 944-982 (2011) [39 pages].
Fertner et al., "Comparison of Various Time Delay Estimation Methods by Computer Simulation," IEEE Transactions on Acoustics, Speech, and Signal Processing, vol. 34, No. 5, pp. 1329-1330 (1986) [2 pages].
Fitch et al., "Point-of-care and standard laboratory coagulation testing during cardiovascular surgery: balancing reliability and timeliness," J. Clin. Monit. Comp., vol. 15, pp. 197-204 (1999) [8 pages].
Flanders et al., "Evaluation and Performance Characteristics of the STA-R Coagulation Analyzer," Clin Chem. 48(9): 1622-1624. PubMed P.M.I.D.: 12194955 (Sep. 2002) [3 pages].
Flax et al., "Phase-Aberration Correction Using Signals from Point Reflectors and Diffuse Scatterers: Basic Principles," IEEE Transactions on Ultrasonics Ferroelectrics & Frequency Control, vol. 35, No. 6, pp. 758-767 (Nov. 1988) [10 pages].
Freedman et al., "A Meta-Analysis of Thromboembolic Prophylaxis Following Elective Total Hip Arthroplasty," Journal of Bone and Joint Surgery, vol. 82-A, pp. 929-938 (2000) [10 pages].
Fricke et al., "A multicenter clinical evaluation of the Clot Signature Analyzer," J. Thromb. Haemostasis 2(5):763-8 (2004) [6 pages].

(56) References Cited

OTHER PUBLICATIONS

Gaetano et al., "Effect of Platelets on Clot Structuration, a Thrombelastographic Study," Thrombosis Research, vol. 3, iss. 4, pp. 425-435 (1973) [12 pages].
Gallippi et al., "Adaptive clutter filtering via blind source," Ultrasonic Imaging, vol. 24, No. 4, pp. 193-214 (2002) [22 pages].
Gallippi et al., "BSS-based filtering of physiological and ARFI induced tissue and blood motion," Ultrasound in Medicine and Biology, vol. 29, No. 11, pp. 1583-1592 (2003) [10 pages].
Gallippi et al., "Complex blind source separation for acoustic radiation force impulse imaging in the peripheral vasculature, in vivo," IEEE Ultrasonics Symposium, vol. 1, pp. 596-601 (2004) [6 pages].
Ganter et al., "Active, personalized, and balanced coagulation management saves lives in patients with massive bleeding," Anesthesiology, vol. 133, No. 5, pp. 1016-1018 (Nov. 2010).
Ganter et al., "Coagulation monitoring: current techniques and clinical use of viscoelastic point-of-care coagulation devices," Anesthesia and Analgesia, vol. 106, No. 5, May 2008, pp. 1366-1375.
Ganter et al., "Kaolin-Based Activated Coagulation Time Measured by Sonoclot in Patients Undergoing Cardiopulmonary Bypass," J. Cardiothorac. Vasc. Anesth. 21(4): 524-8. PubMed P.M.I.D.: 17678778 (Aug. 2007).
Gauss et al., "Adaptive Imagining in the Thyroid Using Fundamental and Harmonic Echo Data," presented at IEEE Ultrasonics Symposium, pp. 1515-1519 (1999).
Gauss et al., "Wavefront Estimation in the Human Breast," presented at SPIE Medical Imaging, vol. 4325, pp. 172-180 (2001).
Giunta et al., "Estimation of Global Motion Parameters by Complex Linear Regression," IEEE Transactions on Image Processing, vol. 8, No. 11, pp. 1652-1657 (1999).
Glidden et al., "Thromboelastograph Assay for Measuring the Mechanical Strength of Fibrin Sealant Clots," Clinical and Applied Thrombosis / Hemostasis, vol. 6, No. 4, pp. 226-233 (Oct. 2000).
Gorlinger et al., "Perioperative Coagulation Management and Control of Platelet Transfusion by Point-of-Care Platelet Function Analysis," Transfus. Med. Hemother. 34:396-411 (2007).
Gorlinger et al., "Recommendations for using the ROTEM® in the management of perioperative bleeding in Cardiac Surgery," Recommendations from the ROTEM® Expert Meeting Working Group, Munich, 10 pages (2007).
Gosselin et al., "Monitoring Oral Anticoagulant Therapy with Point-of-Care Devices: Correlations and Caveats," Clin. Chem. 43(9): 1785-6. PubMed P.M.I.D.: 9299978 (Sep. 1997).
Gottumukkala, Vijaya N., et al., "Assessing Platelet and Fibrinogen Contribution to Clot Strength Using Modified Thromboelastography in Pregnant Women," Anesth. Analg., vol. 89, pp. 1453-1455 (1999).
Greilich et al., "A Modified Thromboelastographic Method for Monitoring c7E3 Fab in Heparinized Patients," Anesth. Analg., vol. 84, pp. 31-38 (1997).
Greilich et al., "Near-Site Monitoring of the Antiplatelet Drug Abciximab Using the Hemodyne Analyzer and Modified Thromboelastograph," J. Cardiothorac. Vasc. Anesth. 13(1):58-64 (Feb. 1999).
Gurbel et al., "Platelet function monitoring in patients with coronary artery disease," Journal of the American College of Cardiology, vol. 50, No. 19, pp. 1822-1834 (Nov. 2007).
Hanecke, P and Klouche, M., "Thrombelastography Today: Practicability and Analytical Power," Transfusion Medicine and Hemotherapy. 34. 421-428 (2007) ("Hanecke").
Hardisty et al., "Fibrinogen as a Co-factor in the Reaction of Platelets with Kaolin," Nature Publishing Group, Edition 210, vol. 644, URL: http://www.nature.com/nature/journal/v210/n5036/abs/210644a0.html (May 7, 1966).
Harris et al., "Coagulation Tests: A Primer on Hemostasis for Clinical Chemists," Clinical Laboratory News, Jan. 1, 2012, retrieved from: https://www.aacc.org/cln/articles/2012/january/coagulation-tests, (4 pages).
Harris et al., "Evaluation of recurrent thrombosis and hypercoagulability," American Family Physician, vol. 56, No. 6, pp. 1591-1596, pp. 1601-1602 (Oct. 1997).
Harrison P., "Assessment of platelet function in the laboratory," Hamostaseologie 29(1):25-31 PM ID:19151842, 7 pages (2009).
Harrison, P., "Platelet Function Analysis," Blood Rev. 19(2): 111-23. Review. PubMed P.M.I.D.: 15603914 (Mar. 2005).
Hartert, "Blood Coagulation Studies with Thromboelastography—A New Research Method," Klin Wochenschrift, 26:577-583 [English translation] (Oct. 1948).
Hartley et al., "Characteristics of Acoustic Streaming Created and Measured by Pulsed Doppler Ultrasound," IEEE Transactions on Ultrasonics, Ferroelectrics, and Frequency Control, vol. 44, No. 6, pp. 1278-1285 (Nov. 1997).
Hartley et al., "Doppler Measurement of Acoustic Streaming," IEEE Ultrasonics Symposium Proceedings, pp. 1537-1540 (1995).
HealthPACT, "Rotational Thromboelastometry (ROTEM)—Targeted Therapy for Coagulation Management in Patients with Massive Bleeding," Health Policy Advisory Committee on Technology; Retrieved from the Internet: URL: https://www.health.qld.gov.au/healthpact/docs/briefs/WP024.pdf, (Nov. 2012) [30 pages].
Hett et al., "Sonoclot Analysis," British Journal of Anaesthesia, vol. 75, No. 6, pp. 771-776. Review. PubMed P.M.I.D.: 8672329 (Dec. 1995).
Hirsh et al., "How we diagnose and treat deep vein thrombosis," Blood, vol. 99, pp. 3102-3110 (2002).
Hirsh et al., "Management of deep vein thrombosis and pulmonary embolism. A statement for healthcare professionals," Council on Thrombosis (in consultation with the Council on Cardiovascular Radiology), American Heart Association, vol. 93, 50 pages (1996).
Hirsh et al., "Oral anticoagulants. Mechanism of Action, Clinical Effectiveness, and Optimal Therapeutic Range," Chest. 102 (4 Suppl.): 312S-326S. Review. PubMed P.M.I.D.: 1345417 (Oct. 1992) [16 pages].
Hoffman et al., "A cell-based model of hemostasis," Thromb. Haemost 2001; 85:958-65 (2001).
Holmes et al., "Novel, Bedside, Tissue Factor-Dependent Clotting Assay Permits Improved Assessment of Combination Antithrombotic and Antiplatelet Therapy," Circulation, vol. 102, pp. 2051-2057 (2000).
Huang et al., "Characterization of Blood Properties from Coagulating Blood of Different Hematocrits Using Ultrasonic Backscatter and Attenuation," Japanese Journal of Applied Physics, vol. 45, No. 9A, pp. 7191-7196 (2006).
Huang et al., "Detection of blood coagulation and clot formation using quantitative ultrasonic parameters," Ultrasound in Medicine and Biology, vol. 31, No. 11, pp. 1567-1573 (Nov. 2005).
Huissoud et al., "Coagulation assessment by rotation thrombelastometry in normal pregnancy," Thromb. Haemostat., vol. 101, pp. 755-761 (2009).
ICKX, B., "Point-of-Care Monitoring of Haemostasis in the OR and the ICU," European Society of Anaesthesiologists., pp. 79-83 (Jun. 5, 2004).
Ivandic et al., "Determination of Clopidogrel Resistance by Whole Blood Platelet Aggregometry and Inhibitors of the P2Y12 Receptor," Clinical Chemistry, vol. 52, No. 3, pp. 383-388. PubMed P.M.I.D.: 16423907 (Mar. 2006).
Jacovitti et al., "Discrete Time Techniques for Time Delay Estimation," IEEE Transactions on Signal Processing, vol. 41, No. 2, pp. 525-533 (Feb. 1993).
Janmey et al., "Kinetics of fibrin oligomer formation observed by electron microscopy," Biochemistry 22(18): 4336-40 (1983).
Janus et al., "Promotion of thrombin-catalyzed activation of factor XIII by fibrinogen," Biochemistry 22(26):6269-72, DOI: 10.1021/bi00295a035, PMID: 6661434 (Dec. 20, 1983).
Jensen et al., "Calculation of pressure fields from arbitrarily shaped, apodized, and excited ultrasound transducers," IEEE Transactions on Ultrasonics, Ferroelectrics, end Frequency Control, vol. 39, pp. 262-267 (1992).
Jensen, "A New Method for Estimation of Velocity Vectors," IEEE Transactions on Ultrasonics, Ferroelectrics and Frequency Control, vol. 45, No. 3, pp. 837-851 (1998).

(56) References Cited

OTHER PUBLICATIONS

Jensen, "Color Flow Mapping Using Phase Shift Estimation," [Excerpt] in Estimation of Blood Velocities Using Ultrasound: A Signal Processing Approach, Cambridge University Press, ISBN: 9780521464840, pp. 195-225 (Mar. 1996). [16 pages].
Jobes et al., "Increased Accuracy and Precision of Heparin and Protamine Dosing Reduces Blood Loss and Transfusion in Patients Undergoing Primary Cardiac Operations," J. Thorac. Cardiovasc. Surg. 110(1): 36-45, PubMed P.M.I.D.: 7609566 (Jul. 1995).
Jolliffe, I.T., [Excerpt: Sec. 1: Introduction] in Principal Component Analysis, Springer Series in Statistics, 2nd edition, Springer, NY, 40 pgs. (2002).
Kadi et al., "On the performance of regression and step-initialized IIR Clutter Filters," IEEE Transactions on Ultrasonics, Ferroelectrics, and Frequency Control, vol. 42, pp. 827-837 (1995).
Kasai et al., "Real-time Two-Dimensional Blood Flow Imaging Using an Autocorrelation Technique," IEEE Ultrasonics Symposium, vol. 32, No. 3, pp. 458-464 (1985).
Katori et al., "The effects of platelet count on clot retraction and tissue plasminogen activator-induced fibrinolysis on thrombelastography," Anesthesia and Analgesia, vol. 100, No. 6, pp. 1781-1785 (Jun. 2005).
Kawasaki et al., "The Effects of Vasoactive Agents, Platelet Agonists and Anticoagulation on Thromboelastography," Act. Anaesthesiol. Scand. 51(9):1273-1244 (Oct. 2007).
Kereiakes et al., "Time Course, Magnitude, and Consistency of Platelet Inhibition by Abciximab, Tirofiban, or Eptifibatide in Patients with Unstable Angina Pectoris Undergoing Percutaneous Coronary Intervention," Am. J. Cardiol. 84(4):391-5, PubMed P.M.I.D.: 10468074 (Aug. 15, 1999).
Keresztes et al., "The PFA-100: analysis and interpretation of a platelet function measurement," The Journal of Cardiovascular Nursing, vol. 20, No. 6, pp. 405-407 (2005).
Kettner et al., "Use of abciximab-Modified Thrombelatography in Patients Undergoing Cardiac Surgery," Anesth. Analg., vol. 89, pp. 580-584 (1999).
Khurana et al., "Monitoring Platelet Glycoprotein IIb/IIIa-fibrin Interaction with Tissue Factor-Activated Thromboelastography," J. Lab. Clin. Med. 130(4):401-411 (Oct. 1997).
Khurana et al., "Thromboelastography Can Rapidly Bioassay Fibrinogen," Anesthesiology, vol. 85, No. 3A, p. A457 (Sep. 1996).
Koepke, J., "Point-of-Care Coagulation Testing," Laboratory Medicine, vol. 31, No. 6, pp. 343-346 (Jun. 2000).
Koster et al., "Evaluation of Post-Cardiopulmonary Bypass Coagulation Disorders by Differential Diagnosis with a Multichannel Modified Thromboelastogram: A Pilot Investigation," J. Extra. Corpor. Technol. 33(3): 153-8, PubMed P.M.I.D.: 11680728 (Sep. 2001).
Kozek-Langenecker, S., "Intensive Care Medicine, Annual Update 2007, Monitoring of Hemostasis in Emergency Medicine," pp. 847-860, Springer New York.
Kruse et al., "A new high-resolution color flow system using an eigendecomposition-based adaptive filter for clutter rejection," IEEE Transactions on Ultrasonics, Ferroelectrics, and Frequency Control, vol. 49, No. 10, pp. 1384-1399 (2002).
Kuntamukkula et al., "Rheological studies of the contractile force within platelet-fibrin clots: effects of prostaglandin E1, dibutyryl-cAMP and dibutyryl-cGMP," Thromb. Res. 13(6):957-69, DOI: 10.1016/0049-3848(78)90225-6, PMID: 219559 (Dec. 1978).
Lang et al., "Different effects of abciximab and cytochalasin D on clot strength in thrombelastography," Journal of Thrombosis and Haemostasis, 2:147-153 (2004), PubMed P.M.I.D.: 14717978.
Lang et al., "Evaluation of the new device ROTEM platelet," [retrieved on Dec. 28, 2015]. Retrieved from the Internet:<URL: https://www.rotem.de/wp-content/uploads/2014/09/Lang-et-al-2014.pdf>, Jan. 1, 2014, 1 page.
Lang et al., "Multi-centre investigation on reference ranges of ROTEM thromboelastometry," Blood Coagulation and Fibrinolysis, 2005, 16: 301-310.
Lang et al., "Possibilities and Limitations of Thromboelastometry/Thromboelastography [Diagnostische Moglichkeiten und Grenzen der Thrombelastometrie/-graphie]," Haemostaseologie 26(3 Suppl 1):S20-9. [German language version]; PMID: 16953288 (Aug. 2006) [13 pages].
Lang et al., "Possibilities and Limitations of Thromboelastometry/Thromboelastography [Diagnostische Moglichkeiten und Grenzen der Thrombelastometrie/-graphie]," Hamostaseologie 26(3 Suppl 1):S20-9. English Translation, with Declaration. PMID: 16953288 (Aug. 2006) [27 pages].
Lang et al., "Possibilities and Limitations of Thromboelastometry/Thromboelastography," Haemostaseologie 26, S21-S29, DOI: 10.1055/s-0037-1617078 (2006) [9 pages].
Ledoux et al., "Reduction of the clutter component in Doppler ultrasound signals based on singular value decomposition: a simulation study," vol. 19, No. 1, pp. 1-18 (1997).
Lerner et al., "Sono-elasticity: medical elasticity images derived from ultrasound signals in mechanically vibrated targets," Ultrasound in Medicine & Biology, vol. 16, pp. 317-327 (1998).
Li et al., "The Xylum Clot Signature Analyzer: A Dynamic Flow System that Simulates Vascular Injury,". Thromb. Res. 92 (6 Suppl. 2):S67-77, PubMed P.M.I.D.: 9886913 (Dec. 15, 1998).
Libgot-Calle et al., "High Frequency Ultrasound Device to Investigate the Acoustic Properties of Whole Blood During Coagulation," Ultrasound Med. Biol. 34.2, pp. 252-264, (2008).
Liptak (CRC Press). Process Measurement and Analysis, vol. 1, Chapter 8, Analytical Instrumentation. 8.53 Rheometers, 1628-1636 (2003).
Liu et al., "Dual fluorescence/contactless conductivity detection for microfluidic chip," Anal Chim Acta. Jul. 28, 2008;621(2):171-7. DOI: 10.1016/j.aca.2008.05.040. Epub May 24, 2008. PMID: 18573381, (7 pages).
Lo, R. et al., "Integrated and reusable in-plane microfluidic interconnects," Sensors and Actuators B: Chemical, vol. 132, iss. 2, pp. 531-539, ISSN 0925-4005 (2008).
Loupas et al., "An axial Velocity Estimator for Ultrasound Blood flow imaging, by means of a two-dimensional autocorrelation approach," IEEE Transactions on Ultrasonics, Ferroelectrics, and Frequency Control, vol. 42, No. 4, pp. 672-688 (1995).
Lubinski et al., "Adaptive strain estimation using retrospective processing medical US elasticity imaging," IEEE Transactions on Ultrasonics Ferroelectrics & Frequency Control, vol. 46, pp. 97-107 (1999).
Machado et al., "Evaluation of an Ultrasonic Method Applied to the Measurement of Blood Coagulation Time," Physiol. Meas. 18(2):129-43, PubMed P.M.I.D.: 9183807 (May 1997).
Mahla et al., "Thromboelastography for monitoring prolonged hypercoagulability after major abdominal surgery," Anesthesia and Analgesia, vol. 92, No. 3, pp. 572-577 (Mar. 2001).
Malinin et al., "Validation of a VerifyNow-P2Y12 cartridge for monitoring platelet inhibition with clopidogrel," Methods and Findings in Experimental and Clinical Pharmacology, vol. 28, No. 5, pp. 315-322 (Jun. 2006).
Mauldin et al., "Adaptive force sonorheometry for assessment of whole blood coagulation," Clin. Chim. Acta. Int. J. Clin. Chem., 411.9-10 pp. 638-644 (2010).
Mauldin et al., "Robust Principal Component Analysis and Clustering Methods for Automated Classification of Tissue Response to ARFI Excitation," Ultrasound in Medicine & Biology, vol. 34, No. 2, pp. 309-325 (2008) [34 pages].
McAleavey et al., "Estimates of echo correlation and measurement bias in acoustic radiation force impulse imaging," IEEE Transactions on Ultrasonics Ferroelectrics & Frequency Control, vol. 50, pp. 631-641 (2003).
Moake, J., "Overview of Hemostasis," Merck Manuals, URL: http://www.merckmanuals.com/professional/hematology-and-oncology/hemostasis/overview-of-hemostasis (2016).
Motovska et al., "Benefits and Risks of Clopidogrel Use in Patients with Coronary Artery Disease: Evidence from Randomized Studies and Registries," Clin. Ther. 30 Pt. 2: 2191-202, J. Clinthera., 2008.12.001. Review. PubMed P.M.I.D.: 19281914. (2008).
Mueller et al., "Utility of the PFA-100 Instrument and the Novel Multiplate Analyzer for the Assessment of Aspirin and Clopidogrel

(56) References Cited

OTHER PUBLICATIONS

Effects on Platelet Function in Patients with Cardiovascular Disease," Clin. Appl. Thromb. Hemost. 15(6): 652-9, PubMed P.M.I.D.: 18805846 (Dec. 2009).
Multiplate® Analyzer Product Guide, © 2013, Roche Diagnostics International Ltd. [21 pages].
Nam et al., "Evaluation of the Roche CoaguChek XS Handheld Coagulation Analyzer in a Cardiac Outpatient Clinic," Ann. Clin. Lab. Sci. 38(1): 37-40, PubMed P.M.I.D.: 18316780 (Winter 2008).
Ng et al., "A Comparative Evaluation of Several Algorithms for Phase Aberration Correction," IEEE Transactions on Ultrasonics Ferroelectrics & Frequency Control, vol. 41, No. 5, pp. 631-643 (Sep. 1994).
Nield et al., "MRI-Based Blood Oxygen Saturation Measurements in Infants and Children with Congenital Heart Disease," Pediatr. Radiol. 32(7):518-522 (Epub Apr. 16, 2002).
Nielsen et al., "A Comparison of the Thrombelastograph and ROTEM," Blood Coagulation and Fibrinolysis 18: 3, 247-252, DOI: 10.1097/MBC.0b013e328092ee05 (2007).
Nielsen et al., "Effects of coagulation factor deficiency on plasma coagulation kinetics determined via thrombelastography: critical roles of fibrinogen and factors II, VII, X and XII," Acta Anesthesiologica Scandanavia, vol. 49, No. 2, pp. 222-231 (Feb. 2005).
Nielsen et al., "Evaluation of the Contribution of Platelets to Clot Strenth by Thromboelastography in Rabbits: The Role of Tissue Factor and Cytochalasin D," Anesth. Analg. 91(1):35-39 (Jul. 2000).
Niewiarowski et al.., "ADP, thrombin, and Bothropsatrox thrombin-like enzyme in platelet dependent fibrin retraction," The American Journal of Physiology 229 (3): 737-45 (1975).
Nightingale et al., "Acoustic Radiation Force Impulse Imaging: In Vivo Demonstration of Clinical Feasibility," Ultrasound in Medicine & Biology, vol. 28, pp. 227-235 (2002).
Nightingale et al., "Acoustic Remote Palpation: Initial in vivo results," presented at IEEE Ultrasonics Symposium, pp. 1553-1558 (2000).
Nightingale et al., "Shear-Wave Generation Using Acoustic Radiation Force: In Vivo and EX Vivo Results," Ultrasound in Medicine & Biology, vol. 29, No. 12, pp. 1715-1723 (2003).
Nock et al., "Synthetic receive aperture imaging with correction for motion and for tissue inhomogeneities. II. Effects of and correction for motion," IEEE Transactions on Ultrasonics, Ferroelectrics, and Frequency Control, vol. 39, No. 4, pp. 496-501 (1992).
Noon et al., "Reduction of Blood Trauma in Roller Pumps for Long-Term Perfusion," World J. Surg. 9(1):65-71 (Feb. 1985).
Novotny et al., "Platelets Secrete a Coagulation Inhibitor Functionally and Antigenically Similar to the Lipoprotein Associated Coagulation Inhibitor," Blood 72(6):2020-2025 (Dec. 1988).
Oberhardt et al., "Dry reagent technology for rapid, convenient measurements of blood coagulation and fibrinolysis," Clinical Chemistry, vol. 37, No. 4, pp. 520-526 (Apr. 1991).
O'Donnell et al., "Internal Displacement and Strain Imaging using Ultrasonic Speckle Tracking," IEEE Transactions on Ultrasonics, Ferroelectrics and Frequency Control, vol. 41, pp. 314-325 (1994).
O'Donnell et al., "Role of the Thrombelastograph as an adjunctive test in thrombophilia screening," Blood Coagulation and Fibrinolysis, vol. 15, No. 3, pp. 207-211 (Apr. 2004).
Ophir et al., "Elastography: A Quantitative Method for Imaging the Elasticity of Biological Tissues," Ultrasonic Imaging, vol. 13, No. 2, pp. 111-134 (1991).
Ozkaya—Fundamentals of biomechanics Equiolobrium, Motion, and Deformation. 2nd Edition. Eds. Nihat Ozkaya and Margareta Nordin. (Springer Science + Business Media, Inc., New York, NY). Chapter 9 "Mechanical Properties of Biological Tissues," pp. 197-218 (1999), 36 pages.
Ozkaya—Fundamentals of biomechanics Equiolobrium, Motion, and Deformation. 3rd Edition. Eds. Nihat Ozkaya and Margareta Nordin. (Springer Science + Business Media, Inc., New York, NY). Chapter 15 "Mechanical Properties of Biological Tissues." pp. 221-236 (2012), 24 pages.
Packham, M., "Role of platelets in thrombosis and hemostasis," Canadian Journal of Physiology and Pharmacology, vol. 72, No. 3, pp. 278-284 (Mar. 1994).
Pallister, C. and Watson, M. (eds.), [Excerpt] "Overview of haemostasis," in Haematology, 2nd ed., Scion Publishing, pp. 336-347, ISBN 978-1904842-39-2 (2011).
Palmeri et al., "Ultrasonic tracking of acoustic radiation force-induced displacements in homogeneous media," IEEE Transactions on Ultrasonics, Ferroelectrics, and Frequency Control, vol. 53, No. 7, pp. 1300-1313 (2006).
Parsons et al., "Age Determiniation of Experimental Venous Thrombi by Ultrasonic Tissue Characterization," Journal of Vascular Surgery, vol. 17, pp. 470-478 (1993).
Patil et al., "3D prostate elastography: algorithm, simulations and experiments," Physics in Medicine & Biology, vol. 52, No. 12, pp. 3643-3663 (2007).
Peeters et al., "Ultrasonic Measurements of Coagulation and Fibrinolysis," J. Clin. Pathol. 17: 320-3, PubMed P.M.I.D.: 14159472; PubMed Central P.M.C.I.D.: PMC480759 (May 1964).
Perry et al., "Point-of-care testing in haemostasis," British Journal of Haematology, vol. 150, No. 5, pp. 501-514 (Sep. 2010).
Pivalizza et al., "Perioperative thromboelastography and sonoclot analysis in morbidly obese patients," Canadian Journal of Anaesthesia, vol. 44, No. 9, pp. 942-945 (Sep. 1997).
Plotkin et al., "A Reduction in Clot Formation Rate and Strength Assessed by Thromboelastography is Indicative of Transfusion Requirements in Patents with Penetrating Injuries," The Journal of Trauma: Injury, Infection, and Critical Care, 64:S64-S68 (2008).
Price et al., "Prognostic Significance of Post-Clopidogrel Platelet Reactivity Assessed by a Point-of-Care Assay on Thrombotic Events after Drug-Eluting Stent Implantation," Eur. Heart Apr. 2008; 29(8):992-1000, PubMed P.M.I.D.: 18263931 (2008).
Prisco et al., "Point-of-Care Testing of Hemostasis in Cardiac Surgery," Thromb. J. 1(1):1 (May 6, 2003).
Puckett et al., "Monitoring blood coagulation with magnetoelastic sensors," Biosensors and Bioelectronics, vol. 18, iss. 5-6, pp. 675-681, ISSN 0956-5663 (2003).
Rahe-Meyer, N. et al., "Multicentric comparison of single portion reagents and liquid reagents for thromboelastometry," Blood Coagul Fibrinolysis Apr. 2009; 20 (3): 218-22. PubMed P.M.I.D.: 19657320.
Rao, G., "Need for a point-of-care assay for monitoring antiplatelet and antithrombotic therapies," Stroke, vol. 40, No. 6, pp. 2271-2272 (Jun. 2009).
Riegger et al., "Teflon-carbon black as new material for the hydrophobic patterning of polymer labs-on-a-chip," Transducers 2009—15th International Conference on Solid-State Sensors, Actuators and Microsystems, pp. 2026-2029, DOI: 10.1109/SENSOR.2009.5285661 (2009).
Rodzynek et al., "The Transfer Test: A New Screening Procedure for Thrombotic Diseases," J. Surg. Res. 35(3):227-233 (Sep. 1983).
ROTEM® delta, "Whole Blood Haemostasis System using Thromboelastometry Operating Manual," 164 pages, Nov. 17, 2014 [brochure].
ROTEM™ "When Minutes Count to Stop the Bleeding," Pentapharm GmbH, www.rotem.de, 6 pages [brochure] (Jun. 2007).
ROTEM™ delta Whole Blood Haemostasis System using Thromboelastometry US Operating Manual, [retrieved on Oct. 30, 2015], Retrieved from the Internet: URL:http://www.sfgh-poct.org/wp-content/uploads/2013/02/ROTEM-delta-US-Operating-Manual-Part-12.pdf, 76 pages (Sep. 2012).
ROTEM™ delta, "Targeted Therapy Stops the Bleeding," 6 pages [brochure] (Jan. 6, 2014).
Rubin et al., "Clinical application of sonographic elasticity imaging for aging of deep venous thrombosis: preliminary findings," Journal of Ultrasound in Medicine, vol. 22, pp. 443-448 (2003).
Rugeri et al., "Diagnosis of early coagulation abnormalities in trauma patients by rotation thrombelastography," J Thromb Haemost., 5 (2): 289-295 (Epub Nov. 16, 2006).
Rumbaut et al., "Chapter 4: Platelet Aggregation," Excerpt from Platelet-Vessel Wall Interactions in Hemostasis and Thrombosis, Morgan & Claypool Life Sciences (pub.), San Rafael, CA, 5 pages (2010).

(56) References Cited

OTHER PUBLICATIONS

Ruzicka et al., "Evaluation of Bedside Prothrombin Time and Activated Partial Thromboplastin Time Measurement by Coagulation Analyzer Coagucheck Plus in Various Clinical Settings," Throm. Res. 87(5) pp. 431-440 (1997). See also, Hillman, R., 1988 U.S. Pat. No. 4,756,884. Capillary Fill Device.
Sakharov et al., "Acceleration of Fibrinolysis by High-Frequency Ultrasound: The Contribution of Acoustic Streaming and Temperature Rise," Thrombosis Research, vol. 100, No. 4, pp. 333-340 (2000).
Salooja et al., "Thromboelastography," Blood Coagul. Fibrinolysis 12(5):327-37 (Jul. 2001).
Sarvazyan et al., "Shear Wave Elasticity Imaging—A New Ultrasonic Technology of Medical Diagnostics," Ultrasound in Medicine and Biology, vol. 24, pp. 1419-1436 (1998).
Scharbert et al., "Evaluation of the Platelet Mapping Assay on Rotational Thromboelastometry ROTEM," Platelets 20(2): 125-30, PubMed P.M.I.D. 19235055 (Mar. 2009).
Schmitt et al., "Characterization of blood clot viscoelasticity by dynamic ultrasound elastography and modeling of the rheological behavior," Journal of Biomechanics, vol. 44, No. 4, pp. 622-629 (2011).
Schocl et al., "Use of Rotation Thromboelastometry (ROTEM®) to Achieve Successful Treatment of Polytrauma with Fibrinogen Concentrate and Prothrombin Complex Concentrate," Anaesthesia, J. Assoc. Anaes. of Great Britain and Ireland, vol. 65, pp. 199-203 (2010).
Shi et al., "Color Doppler Detection of Acoustic Streaming in a Hematoma Model," Ultrasound in Medicine and Biology, vol. 27, No. 9, pp. 1255-1264 (2001).
Shi et al., "Color Doppler imaging of acoustic streaming in blood and clot," IEEE Ultrasonics Symposium, vol. 2, pp. 1315-1318 (1999).
Shi et al., "Experimental Investigation and Finite Element Simulation of Streaming in Blood in Cylindrical Models," IEEE Ultrasonics Symposium, vol. 2, pp. 1509-1512 (2000).
Shi, "Quantitative Investigation of Acoustic Streaming in Blood," J. Acoust. Soc. Am. 111, pp. 1110-1121 (Feb. 2002).
Shih et al., "In Vitro Assessments of Viscoelastic Properties of Fibrin Clot by Using Acoustic Radiation Force on a Solid Sphere," International Ultrasonics Symposium Proceedings, IEEE, pp. 479-482 (2010).
Shore-Lesseron et al., "Thromboelastography-Guided Transfusion Algorithm Reduces Transfusions in Complex Cardiac Surgery," Anesth. Analg. 88(2):312-319 (Feb. 1999).
Shore-Lesseron, "Evidence Based Coagulation Monitors: Heparin Monitoring, Thromboelastography, and Platelet Function," Sem. Cardiothoracic Vasc. Anesthesia. 9(1): 42-52 (Mar. 2005).
Shung et al., "Ultrasonic characterization of blood during coagulation," Journal of Clinical Ultrasound, vol. 12, No. 3, pp. 147-153 (1984).
Sinn et al., "Platelet aggregation monitoring with a newly developed quartz crystal microbalance system as an alternative to optical platelet aggregometry," Analyst, vol. 135, pp. 2930-2938 (2010).
Skovoroda et al., "Tissue elasticity reconstruction based on ultrasonic displacement and strain images," IEEE Transactions on Ultrasonics, Ferroelectrics, and Frequency Control, vol. 42, No. 4, pp. 747-765 (1995).
Soria et al., "Fibrin Stabilizing Factor (F XIII) and Collagen Polymerization," Experientia 31(11):1355-1357 (Nov. 15, 1975).
Spannagl et al., "Point-of-Care Analysis of the Homeostatic System," Laboratoriumsmedizin (Kirchheim, DE) 26(1-2):68-76 (Feb. 2002).
Spiel et al., "Validation of rotation thrombelastography in a model of systemic activation of fibrinolysis and coagulation in humans," Journal of Thrombosis and Haemostasis 4:411-416 (2006).
Srinivasa et al., "Thromboelastography: Where is it and Where is it Heading?" Int'l. Anesthesiology Clinics 39(1):35-49 (Winter 2001).
Srinivasan et al., "Elastographic imaging using staggered strain estimates," Ultrasonic Imaging, vol. 24, pp. 229-245 (2002).

Stony Brook Portable Field Viscometer (For a quick 'Pass' or 'Fail' decision) [undated], 2 pgs.
Straub et al., "Using Reagent-Supported Thromboelastometry (ROTEM®) to Monitor Haemostatic Changes in Congenital Heart Surgery Employing Deep Hypothermic Circulatory Arrest," European Journal of Cardio-thoracic Surgery, vol. 34, pp. 641-647 (2008).
Strobach, P., "Low-rank adaptive filters," IEEE Trans Signal Process, vol. 44, No. 12, pp. 2932-2947 (1996).
Sugimoto et al., "Tissue Hardness Measurement Using the Radiation Force of Focused Ultrasound," Proc. IEEE Ultrason. Symp., pp. 1377-1380 (1990).
Sumino et al., "Measurements of ultrasonic pulse arrival time differences produced by abdominal wall specimens," Journal of the Acoustical Society of America, vol. 90, No. 6, pp. 2924-2930 (1991).
Taborski et al., "Analytical Performance of the New Coagulation Monitoring System INRatio for the Determination of INR Compared with the Coagulation Monitor Coaguchek S and an Established Laboratory Method," J. Thromb. Thrombolysis. 18(2): 103-7, PubMed P.M.I.D.: 15789176 (Oct. 2004).
Tanaka et al., "Thrombin Generation Assay and Viscoelastic Coagulation Monitors Demonstrate Differences in the Mode of Thrombin Inhibition Between Unfractionated Heparin and Bivalirudin," Anesth. Analg. 105(4):933-939 (Oct. 2007).
TEG 5000 Thrombelastograph Hemostasis System User Manual with TEG Analytical Software (TAS) Version 4.2.3 including 8 pages. an addendum (2008) for TEG Analytical Software (TAS) Version 4.3 (the "TEG 5000 User Manual"), 278 pages (2007).
Theusinger et al., "Rotation thromboelastometry (ROTEM) stability and reproducibility over time," Eur. J. Cardio-Thor. Surg. 37.3, pp. 677-683 (2009).
Thuerlemann et al., "Monitoring thrombin generation by electrochemistry: development of an amperometric biosensor screening test for plasma and whole blood," Clinical Chemistry, vol. 55, No. 3, pp. 505-512 (Mar. 2009).
Thurston GB., "Viscoelasticity of Human Blood," Biophysical Journal 12: 1205-1217 (1972).
Tomauiolo et al., "Regulation of Platelet Activation and Coagulation and Its Role in Vascular Injury and Arterial Thrombosis," Interv. Cardiol. Clin. 6 (1): 1-12 (Jan. 2017).
Tonal et al., "Comparison of procoagulatory markers in function of anesthesic/analgesic technique used on the surgery of traumathology prosthesis replacement," European Journal of Anaesthesiology: May 2008—vol. 25—Issue—p. 84.
Toner et al., "Blood-on-a-chip," Annual Review of Biomedical Engineering, vol. 7, pp. 77-103 (2005).
Torr, "The Acoustic Radiation Force," Am. J. Phys., vol. 52, pp. 402-408 (1984).
Traverso et al., "Prospective assessment of the risk of deep vein thrombosis in elective abdominal surgery. Predictive role of [Thrombelastograph® analysis]." Thromb. Haemorrh. Disorders 71:9-15 (1993).
Tripodi et al., "International Sensitivity Index Calibration of the Near-Patient Testing Prothrombin Time Monitor, Pro Time," Am. J. Clin. Pathol. 119 (2): 241-5, PubMed P.M.I.D.: 12579994 (Feb. 2003).
Tucci et al., "Platelet function monitoring with the Sonoclot analyzer after in vitro tirofiban heparin administration," J. Thor. Cardiovasc. Surg. 131.6, pp. 1314-1322 (2006).
Van Den Berg A., Lammerink T.S.J., "Micro Total Analysis Systems: Microfluidic Aspects, Integration Concept and Applications," In: Manz A., Becker H. (eds) Microsystem Technology in Chemistry and Life Science. Topics in Current Chemistry, vol. 194. Springer, Berlin, Heidelberg. DOI: 10.1007/3-540-69544-3_2 (1998).
Venema et al., "An assessment of clinical interchangeability of TEG and ROTEM thromboelastographic variables in cardiac surgical patients," Anesth. Analg. 111.2:339-344 (2010).
VerifyNow® Product Guide, [undated; Exh. 2018 / IPR2017-00855] 10 pages.
Versteeg et al., "New Fundamentals in Hemostasis," Physiol. Rev. 93 (1): 327-58. Review. PubMed P.M.I.D.: 23303912 (Jan. 2013).

(56) References Cited

OTHER PUBLICATIONS

Vig et al., "Thromboalastography: a reliable test?" Blood Coagulation and Fibrinolysis, vol. 12, No. 7, pp. 555-561 (Oct. 2001).
Viola et al., "A Comparison between spline-based and phase domain time-delay estimators," IEEE Transactions on Ultrasonics, Ferroelectrics, and Frequency Control, vol. 53, No. 3, pp. 515-517 (2006).
Viola et al., "A comparison of the performance of time-delay estimators in medical ultrasound," IEEE Transactions on Ultrasonics Ferroelectrics & Frequency Control, vol. 50, pp. 392-401 (2003).
Viola et al., "A Novel Ultrasound-Based Method to Evaluate Hemostatic Function of Whole Blood," Clin Chim Acta, vol. 411, Nos. 1-2, 2010, pp. 106-113.
Viola et al., "A Spline Based Algorithm for Continuous Time Delay Estimation Using Sampled Data," IEEE Transactions on Ultrasonics Ferroelectrics & Frequency Control, in press, pp. 80-93 (2005).
Viola et al., "Analysis of Clot Formation with Acoustic Radiation Force," SPIE Proceedings, vol. 4689, pp. 235-242 and pp. 1-2 (2002).
Viola et al., "Comparison of Time Delay Estimators in Medical Ultrasound," IEEE Ultrasonics Symposium, vol. 2, pp. 1485-1488 (2001).
Viola et al., "Efficient and Accurate Spline-Based Time Delay Estimation," IEEE Ultrasonics Symposium, vol. 2, pp. 870-873 (2004).
Viola et al., "Imaging Viscoelastic Properties of the Vitreous," Ultrasonics Symposium, vol. 2, pp. 1623-1626 (2001).
Viola et al., "Radiation Force Imaging of Viscoelastic Properties with Reduced Artifacts," IEEE Trans. on Ultrasonics, Ferroelectrics, and Frequency Control, vol. 50, No. 6, pp. 736-742 (2003).
Viola et al., "Sonorheometry: A new Method for Assessing Coagulation Potential," IEEE Ultrasonics Symposium, vol. 1, pp. 1001-1004 (2007).
Viola et al., "Sonorheometry: A Noncontact Method for the Dynamic Assessment of Thrombosis," The Annals of Biomedical Engineering, vol. 32, pp. 696-705 (2004).
Viola et al., "Ultrasound Echo Decorrelation Due to Acoustic Radiation Force," IEEE Ultrasonics Symposium Proceedings, vol. 2, pp. 1903-1906 (2002).
Voleisis et al., "Ultrasonic Method for the Whole Blood Coagulation Analysis," Ultrasonics, vol. 40, pp. 101-107 (May 2002).
Walker et al., "A Fundamental Limit on Delay Estimation Using Partially Correlated Speckle Signals," IEEE Transactions on Ultrasonics, Ferroelectrics and Frequency Control, vol. 42, pp. 301-308 (1995).
Walker et al., "A Fundamental Limit on the Accuracy of Speckle Signal Alignment," IEEE Ultrasonics Symposium Proceedings, vol. 3, pp. 1787-1791 (1994).
Walker et al., "A Method of Imaging Viscoelastic Parameters with Acoustic Radiation Force," Physics in Medicine and Biology, vol. 45, No. 6, pp. 1437-1447 (2000).
Walker et al., "Application of Acoustic Radiation Force in Opthalmic Ultrasound," Proc. IEEE Symp., vol. 2, pp. 1291-1295 (1997).
Walker et al., "Real-Time Imaging of Tissue Vibration Using a Two-Dimensional Speckle Tracking System," 1993 IEEE Ultrason. Symp., pp. 873-877 (1993).
Walker et al., "The Significance of Correlation in Ultrasound Signal Processing," SPIE Proc., vol. 4325, pp. 159-171 (2001).
Webster, J. (ed.), [Excerpt] Medical Instrumentation: Application and Design, New York: John Wiley & Sons, 696 pages (2010). Fourth Edition.
Webster, J. (ed.), [Excerpt] Medical Instrumentation: Application and Design, New York: John Wiley & Sons, 7 pages (1998).
Weisel, J., "The Mechanical Properties of Fibrin for Basic Scientists and Clinicians," Biophys. Chem. 112(2-3):267-76, DOI: 10.1016/j.bpc.2004.07.029, PMID: 15572258 (Dec. 2004).
Weiss et al., "The Effect of Salicylates on the Hemostatic Properties of Platelets in Man," The Journal of Clinical Investigation, vol. 47, No. 9, pp. 2169-2180, DOI: 10.1172/JCI05903 (1968).

Westbrook et al., "Protocol Based on Thromboelastograph (TEG) Out-Performs Physician Preference Using Laboratory Coagulation Tests to Guide Blood Replacement During and After Cardiac Surgery: A Pilot Study," Heart, Lung and Circulation, vol. 18, No. 4, pp. 277-288 (Aug. 2009).
Whitten et al., "Thromboelastography: Past, Present and Future," Anesthesiology, vol. 92, No. 5, pp. 1223-1225 (May 2000).
Wolberg AS., "Plasma and cellular contributions to fibrin network formation, structure and stability," Haemophilia, 16 (Suppl 3), pp. 7-12, DOI: 10.1111/j.1365-2516.2010.02253.x, PMID: 20586795 (2010).
Wolff et al., "Aspirin for the Primary Prevention of Cardiovascular Events: An Update of the Evidence for the U.S. Preventive Services Task Force," Ann. Intern. Med. 150(6):405-10, Review, PMID: 19293073 (Mar. 17, 2009).
Yu et al., "Single-Ensemble-Based Eigen-Processing Methods for Color Flow Imaging," IEEE Transactions on Ultrasonics, Ferroelectrics and Frequency Controls, vol. 55, No. 3, pp. 573-587 (2008).
Appendix A—SNQ No. 1 of Request for Ex Parte Reexamination of U.S. Pat. No. 11,061,038 filed by a Third Party Requester, Nov. 3, 2021, 102 pages.
Appendix B—SNQ No. 2 of Request for Ex Parte Reexamination of U.S. Pat. No. 11,061,038 filed by a Third Party Requester, Nov. 3, 2021, 112 pages.
Appendix C—SNQ No. 3 of Request for Ex Parte Reexamination of U.S. Pat. No. 11,061,038 filed by a Third Party Requester, Nov. 3, 2021, 126 pages.
Appendix D—SNQ No. 4 of Request for Ex Parte Reexamination of U.S. Pat. No. 11,061,038 filed by a Third Party Requester, Nov. 3, 2021, 139 pages.
Corrected Citations for the Petition as filed for Inter Partes Review of U.S. Pat. No. 9,272,280 B2, dated Jul. 26, 2017 [IPR2017-00852], 4 pages [Exhibit 1012].
Corrected Citations for the Petition as filed for Inter Partes Review of U.S. Pat. No. 9,410,972 dated Jul. 26, 2017, 6 pages.
Curriculum Vitae for Frank M. Laduca, Ph.D., For Inter Partes Review of U.S. Pat. No. 9,915,671 dated Jan. 30, 2019, 4 pages.
Curriculum Vitae for James P. Landers, For Inter Partes Review of U.S. Pat. No. 10,031,144 dated May 28, 2019, 25 pages.
Curriculum Vitae for James P. Landers, For Inter Partes Review of U.S. Pat. No. 9,977,039 dated May 28, 2019, 25 pages.
Curriculum Vitae for Patrick D. Mize, Ph.D., For Inter Partes Review of U.S. Pat. No. 9,272,280 dated Sep. 26, 2017, 4 pages.
Curriculum Vitae for Scott Diamond, Ph.D., For Inter Partes Review of U.S. Pat. No. 9,272,280 dated Jan. 9, 2018, [IPR2017-00852] 15 pages.
Curriculum Vitae for Scott Diamond, Ph.D., For Inter Partes Review of U.S. Pat. No. 9,410,971 dated Jan. 18, 2018, 15 pages.
Curriculum Vitae for Scott Diamond, Ph. D., For Inter Partes Review of U.S. Pat. No. 9,915,671 dated Apr. 15, 2019, 15 pages.
Curriculum Vitae of Keith B. Neeves dated Sep. 1, 2020, (25 pages) [Exhibit 1003. IPR2021-00293].
Decision Denying Institution of Inter Partes Review for Inter Partes Review of U.S. Pat. No. 9,410,971, dated May 10, 2018, 15 pages.
Decision Denying Patent Owner's Request for Rehearing of Final Decision [Paper 32] on U.S. Pat. No. 9,915,671, entered Dec. 5, 2019, 12 pages [IPR2018-00950].
Decision Denying Petitioner's Motion to Withdraw Grounds for Inter Partes Review of U.S. Pat. No. 9,410,971, entered Jul. 11, 2018, 9 pages.
Decision Denying Petitioner's Request for Rehearing for Inter Partes Review of U.S. Pat. No. 9,410,971, entered Nov. 3, 2017, 7 pages [Paper 20].
Decision Granting Institution of Inter Partes Review [Paper 9] dated Jul. 1, 2021 [U.S. Pat. No. 10,746,750], of Request for Ex Parte Reexamination filed by a Third-Party Requester, Nov. 3, 2021, 30 pages [IPR2021-00293 ].
Decision Granting Patent Owner's Motion to Seal & Enter Jointly Proposed Protective Order for Inter Partes Review of U.S. Pat. No. 9,915,671, dated May 15, 2019, 6 pages.

(56) References Cited

OTHER PUBLICATIONS

Decision Granting Patent Owner's Motion to Submit Supplemental Information for Inter Partes Review [IPR2017-00852] of U.S. Pat. No. 9,272,280, dated Jul. 11, 2018, 10 pages.
Decision Granting Patent Owner's Motion to Submit Supplemental Information for Inter Partes Review of U.S. Pat. No. 9,410,971, dated Jul. 11, 2018, [IPR2017-00855] 10 pages.
Decision Granting Patent Owner's Motion to Submit Supplemental Information for Inter Partes Review of U.S. Pat. No. 9,915,671, dated Jun. 12, 2019, 8 pages.
Decision Institution of Inter Partes Review for Inter Partes Review [IPR2017-00852]of U.S. Pat. No. 9,272,280, dated Sep. 1, 2017, 13 pages.
Decision Institution of Inter Partes Review for Inter Partes Review of U.S. Pat. No. 9,410,971 [Paper 14], dated Sep. 1, 2017, 27 pages.
Decision to Institute for Inter Partes Review of U.S. Pat. No. 9,915,671, dated Oct. 5, 2018, 27 pages.
Declaration of Frank M. Laduca as filed for Inter Partes Review of U.S. Pat. No. 10,031,144 dated Apr. 29, 2019, 130 pages.
Declaration of Frank M. Laduca, Ph.D., For Inter Partes Review of U.S. Pat. No. 9,915,671 dated Jan. 4, 2019, 37 pages.
Declaration of Frank M. Laduca, Ph.D., For Inter Partes Review of U.S. Pat. No. 9,977,039 dated Feb. 21, 2019, 117 pages.
Declaration of James P. Landers, For Inter Partes Review of U.S. Pat. No. 10,031,144 dated Jul. 29, 2019, 56 pages.
Declaration of James P. Landers, For Inter Partes Review of U.S. Pat. No. 9,977,039 dated May 28, 2019, 51 pages.
Declaration of John Avila for Inter Partes Review of U.S. Pat. No. 9,915,671, dated Jan. 4, 2019, 38 pages.
Declaration of Keith B. Neeves, Ph. D. filed on Dec. 14, 2020, [IPR2021-00293 / Exhibit 1002 / U.S. Pat. No. 10,746,750], 151 pgs.
Declaration of Patrick D. Mize, Ph.D., For Inter Partes Review of U.S. Pat. No. 9,272,280 dated Feb. 3, 2017, 67 pages.
Declaration of Patrick D. Mize, Ph.D., For Inter Partes Review of U.S. Pat. No. 9,410,971 dated Feb. 3, 2017, 124 pages.
Declaration of Scott Diamond, Ph.D., For Inter Partes Review of U.S. Pat. No. 9,272,280 dated Dec. 1, 2017, 48 pages.
Declaration of Scott Diamond, Ph.D., For Inter Partes Review of U.S. Pat. No. 9,410,971 [IPR2017-00855] dated Dec. 1, 2017, 70 pages.
Declaration of Scott L. Diamond filed Apr. 20, 2018 in Request for Ex Parte Reexamination of U.S. Pat. No. 9,915,671 [IPR2018-00950 / PTAB], 200 pages.
Deposition of Frank M. Laduca, Ph.D., For Inter Partes Review of U.S. Pat. No. 9,915,671 dated Feb. 13, 2019, 271 pages.
Deposition of John Avila for Inter Partes Review of U.S. Pat. No. 9,915,671, dated Feb. 5, 2019, 75 pages.
Deposition of Patrick D. Mize, Ph.D., For Inter Partes Review of U.S. Pat. No. 9,410,971 dated Oct. 5, 2017, 81 pages.
Deposition of Scott Diamond, Ph.D., For Inter Partes Review of U.S. Pat. No. 9,272,280 [IPR2017-00852] and U.S. Pat. No. 9,410,971 [IPR2017-00855] dated Jan. 18, 2018, 229 pages.
Deposition of Scott Diamond, Ph.D., For Inter Partes Review of U.S. Pat. No. 9,915,671 dated Apr. 26, 2019, 385 pages.
Deposition of Scott Diamond, Ph.D., For Inter Partes Review of U.S. Pat. No. 9,915,671 dated Nov. 15, 2018, 330 pages.
Deposition on Motion for Leave to File for Inter Partes Review of U.S. Pat. No. 9,272,280 B2, dated Jun. 26, 2017, 72 pages.
Electronic Acknowledgment Receipt of Request for Ex Parte Reexamination of U.S. Pat. No. 11,061,038 [U.S. Appl. No. 90/019,032] filed by a Third Party Requester Nov. 3, 2021, 7 pages.
Events Relating to Motion to Submit Supplemental Information as filed for Inter Partes Review of U.S. Pat. No. 9,915,671 dated May 28, 2019, [Exhibits 1069 and 1074], 2 pages.
File History of U.S. Appl. No. 13/397,398 as filed for Inter Partes Review of U.S. Pat. No. 9,272,280 dated Dec. 1, 2017, 873 pages.
File History of U.S. Appl. No. 15/202,059 (filed Jul. 24, 2018) for Inter Partes Review of U.S. Pat. No. 10,031,144, 472 pages.
File History of U.S. Appl. No. 17/182,502 [U.S. Pat. No. 11,061,038, issued Jul. 13, 2021] for Request for Ex Parte Reexamination filed by a Third Party Requester, 416 pages.
File History of U.S. Appl. No. 16/146,333 (filed Sep. 28, 2018) [U.S. Pat. No. 10,746,750], 156 pages.
Final Written Decision [Paper 47] in *Instrumentation Laboratory Co.* v. *HemoSonics LLP* ["852 FWD"] For *Inter Partes* Review [IPR2017-00852] of U.S. Pat. No. 9,272,280 B2, dated Feb. 13, 2019, 25 pages.
Final Written Decision in *Instrumentation Laboratory Co.* v. *HemoSonics LLP* ["971 FWD"] For *Inter Partes* Review of U.S. Pat. No. 9,410,971, dated Feb. 13, 2019, [Paper 55 / IPR2017-00855] 55 pages.
Final Written Decision in IPR2018-00950 for U.S. Pat. No. 9,915,671, entered Oct. 2, 2019, [Paper 30] 49 pages.
Final Written Decision, *Hemosonics LLC* v. *C.A. Casyso GMBH*, Case IPR2021-00293, [Paper 18], for Request for *Ex Parte* Reexamination of U.S. Pat. No. 10,746,750, [Exhibit 1009], 32 pages, Jun. 21, 2022.
General Order in Cases Remanded Under *Arthrex, inc.* v. *Smith & Nephew, Inc.* [PTAB / 914 F.3D 1320 (Fed. Cir. 2019)], of Request for *Ex Parte* Reexamination filed by a Third-Party Requester, 6 pages [IPR2018-00950].
Grant of Good Cause Extension for Inter Partes Review [IPR2017-00852] of U.S. Pat. No. 9,272,280 B2 [Paper 44] dated Aug. 28, 2018, 3 pages.
Grant of Good Cause Extension for Inter Partes Review of U.S. Pat. No. 9,410,971 B2, [Paper 52], dated Aug. 28, 2018, 3 pages.
*Instrumentation Laboratory Co.* v. *HemoSonics LLP*, For *Inter Partes* Review of U.S. Pat. No. 9,410,971, (IPR201700855 Conference Call Transcript), (PTAB May 22, 2018), 50 pages.
*Instrumentation Laboratory Co.* v. *HemoSonics LLP*, For *Inter Partes* Review of U.S. Pat. No. 9,410,971, (IPR201700855 Conference Call Transcript), (PTAB May 4, 2018), 72 pages.
Joint Request for Change of Oral Argument Location for Inter Partes Review of U.S. Pat. No. 9,915,671, dated Oct. 11, 2018, 2 pages.
Jointly Proposed Protective Order [Motion to Seal] for Inter Partes Review of U.S. Pat. No. 9,915,671, dated Jan. 8, 2019, 14 pages.
Judgement Affirming PTAB, *C.A. Casyso GMBH* v. *Hemosonics LLC*, Appeal No. 2020-1444 (Fed. Cir. Jun. 13, 2022) for Request for *Ex Parte* Reexamination of U.S. Pat. No. 10,175,225 [IPR2018-00950], 3 pages.
Notice concerning Alternative Dispute Resolution Date for InterPartes Review of U.S. Pat. No. 10,031,144, dated Apr. 29, 2019, 2 pages.
Notice of Deposition for Frank M. Laduca, Ph.D., For Inter Partes Review of U.S. Pat. No. 9,915,671 dated Jan. 30, 2019, 3 pages.
Notice of Deposition for John Avila for Inter Partes Review of U.S. Pat. No. 9,915,671, dated Jan. 25, 2019, 3 pages.
Notice of Deposition for Patrick D. Mize, Ph.D., For Inter Partes Review of U.S. Pat. No. 9,272,280 B2 [IPR2017-00852] and U.S. Pat. No. 9,410,971 [IPR2017-00855], dated Sep. 26, 2017, 3 pages.
Notice of Deposition for Scott Diamond, Ph.D., For Inter Partes Review of U.S. Pat. No. 9,272,280 [IPR2017-00852] and U.S. Pat. No. 9,410,971 [IPR2017-00855] dated Jan. 9, 2018, 3 pages.
Notice of Deposition for Scott Diamond, Ph.D., For Inter Partes Review of U.S. Pat. No. 9,915,671 dated Apr. 15, 2019, 3 pages.
Notice of Filing Date for Inter Partes Review [IPR2017-00852] of U.S. Pat. No. 9,272,280 B2, [Paper 5] dated Mar. 6, 2017, 5 pages.
Notice of Filing Date for Inter Partes Review of U.S. Pat. No. 10,031,144, dated Apr. 29, 2019, 3 pages.
Notice of Filing Date for Inter Partes Review of U.S. Pat. No. 9,410,971 dated Dec. 12, 2017, 4 pages.
Notice of Filing Date for Inter Partes Review of U.S. Pat. No. 9,915,671, dated May 8, 2018, 5 pages.
Notice of Filing Date for Inter Partes Review of U.S. Pat. No. 9,977,039, dated Feb. 27, 2019, 5 pages.
Notice of Refund for InterPartes Review of U.S. Pat. No. 9,410,971 dated Jun. 4, 2018, 2 pages.
Order Extending One-Year Pendency for Good Cause for Inter Partes Review of U.S. Pat. No. 9,272,280 B2, [Paper 45], dated Aug. 28, 2018, 4 pages.

(56) References Cited

OTHER PUBLICATIONS

Order Extending One-Year Pendency for Good Cause for Inter Partes Review of U.S. Pat. No. 9,410,971, entered Aug. 28, 2018, 3 pages.
Order Granting Request for Ex Parte Reexamination of U.S. Pat. No. 11,061,038, issued Dec. 10, 2021, 15 pages.
Order re: Conduct of Proceeding for Inter Partes Review of U.S. Pat. No. 9,272,280 B2 and U.S. Pat. No. 9,410,971 B2, [Paper 11] dated Jul. 10, 2017, 7 pages.
Order re: Conduct of Proceeding for Inter Partes Review of U.S. Pat. No. 9,272,280 B2 and U.S. Pat. No. 9,410,971 B2, [Paper 13] dated Jul. 10, 2017, 7 pages.
Order re: Conduct of Proceeding for Inter Partes Review of U.S. Pat. No. 9,410,971 B2, [Paper 28], dated Apr. 26, 2018, 3 pages.
Order re: Conduct of Proceeding for Inter Partes Review of U.S. Pat. No. 9,410,971 dated Mar. 9, 2018, 6 pages.
Order re: Conduct of Proceeding for Inter Partes Review of U.S. Pat. No. 9,410,971 dated May 5, 2017, 3 pages.
Order re: Conduct of the Proceeding for Inter Partes Review [IPR2017-00852] of U.S. Pat. No. 9,272,280 B2 dated Apr. 26, 2018, 3 pages.
Order re: Supplemental Trial Hearing for Inter Partes Review of U.S. Pat. No. 9,272,280 B2 dated Aug. 6, 2018, 6 pages.
Order re: Trial Hearing for Inter Partes Review of U.S. Pat. No. 9,272,280 B2 [IPR2017-00852] and U.S. Pat. No. 9,410,971 B2 [IPR2017-00855] dated Jun. 4, 2018, [Paper 31] 6 pages.
Order re: Trial Hearing for Inter Partes Review of U.S. Pat. No. 9,915,671, dated Jun. 5, 2019, 6 pages.
Order: Conduct of Proceeding for Inter Partes Review of U.S. Pat. No. 9,410,971 dated May 24, 2018, 5 pages.
Panel Change Order Conduct of the Proceeding for Inter Partes Review of U.S. Pat. No. 9,915,671, dated Jan. 10, 2019, 3 pages.
Patent Owner's Mandatory Notices for Inter Partes Review of U.S. Pat. No. 10,031,144, dated May 8, 2019, 4 pages.
Patent Owner's Mandatory Notices for Inter Partes Review of U.S. Pat. No. 9,272,280 B2 [IPR2017-00852], dated Jun. 5, 2018, 4 pages.
Patent Owner's Mandatory Notices for Inter Partes Review of U.S. Pat. No. 9,272,280 B2, dated Feb. 23, 2017, 4 pages.
Patent Owner's Mandatory Notices for Inter Partes Review of U.S. Pat. No. 9,410,971, dated Dec. 13, 2017, 5 pages.
Patent Owner's Mandatory Notices for Inter Partes Review of U.S. Pat. No. 9,410,971, dated Feb. 23, 2017, 4 pages.
Patent Owner's Mandatory Notices for Inter Partes Review of U.S. Pat. No. 9,915,671, dated May 10, 2018, 3 pages.
Patent Owner's Mandatory Notices for Inter Partes Review of U.S. Pat. No. 9,977,039, dated Mar. 7, 2019, 4 pages.
Patent Owner's Motion to Seal for Inter Partes Review of U.S. Pat. No. 9,915,671, dated Jan. 4, 2019, 14 pages.
Patent Owner's Motion to Submit Supplemental Information for Inter Partes Review of U.S. Pat. No. 9,915,671, dated May 21, 2019, 35 pages.
Patent Owner's Objection to Evidence for Inter Partes Review of U.S. Pat. No. 9,272,280, dated Sep. 18, 2017, 3 pages.
Patent Owner's Objection to Evidence for Inter Partes Review of U.S. Pat. No. 9,410,971, dated Sep. 18, 2017, 3 pages.
Patent Owner's Objection to Petitioner's Demonstrative Exhibits for Inter Partes Review of U.S. Pat. No. 9,272,280 B2, dated Aug. 10, 2018, [IPR2017-00852], 4 pages.
Patent Owner's Objection to Petitioner's Demonstratives for Inter Partes Review of U.S. Pat. No. 9,410,971, dated Aug. 10, 2018, 4 pages.
Patent Owner's Objection to Petitioner's Motion to Submit Supplemental Information for Inter Partes Review of U.S. Pat. No. 9,272,280 B2, dated May 30, 2018, [IPR2017-00852 / Paper 29], 10 pages.
Patent Owner's Objection to Petitioner's Motion to Submit Supplemental Information for Inter Partes Review of U.S. Pat. No. 9,410,971, dated May 30, 2018, 10 pages.
Patent Owner's Objection to Petitioner's Motion to Withdraw Grounds for Inter Partes Review of U.S. Pat. No. 9,410,971, dated Jun. 8, 2018, 11 pages.
Patent Owner's Preliminary Response for Inter Partes Review for U.S. Pat. No. 9,272,280 dated Jun. 6, 2017, [IPR2017-00852] 34 pages.
Patent Owner's Preliminary Response for Inter Partes Review for U.S. Pat. No. 9,410,971 dated Jun. 7, 2017, 60 pages.
Patent Owner's Preliminary Response for Inter Partes Review for U.S. Pat. No. 9,915,671 dated Jul. 20, 2018, 14 pages.
Patent Owner's Preliminary Response for IPR2021-00293 of U.S. Pat. No. 10,746,750, filed Apr. 22, 2021, 6 pages.
Patent Owner's Preliminary Response to Petition for Post Grant Review for Inter Partes Review of U.S. Pat. No. 10,031,144, dated Jul. 29, 2019, 51 pages.
Patent Owner's Preliminary Response to Petition for Post Grant Review for Inter Partes Review of U.S. Pat. No. 9,977,039, dated May 28, 2019, 53 pages.
Patent Owner's Preliminary Response to Petition Requesting Inter Partes Review of U.S. Pat. No. 9,410,971, dated Feb. 14, 2018, 33 pages.
Patent Owner's Request for Oral Argument for Inter Partes Review of U.S. Pat. No. 9,272,280 B2, dated Apr. 10, 2018, [IPR2017-00852] 3 pages.
Patent Owner's Request for Oral Argument for Inter Partes Review of U.S. Pat. No. 9,410,971, dated Apr. 10, 2018, 3 pages.
Patent Owner's Request for Oral Argument for Inter Partes Review of U.S. Pat. No. 9,915,671, dated Jun. 3, 2019, 3 pages.
Patent Owner's Request for Supplemental Oral Hearing for Inter Partes Review of U.S. Pat. No. 9,272,280 B2, dated Aug. 3, 2018, [IPR2017-00852] 3 pages.
Patent Owner's Request for Supplemental Oral Hearing for Inter Partes Review of U.S. Pat. No. 9,410,971, dated Aug. 3, 2018, 3 pages.
Patent Owner's Response for IPR2018-00950 of U.S. Pat. No. 9,915,671, filed Jan. 4, 2019, 37 pages.
Patent Owner's Response to Petition under 37 C.F.R. §42.120 for IPR2021-00293 of U.S. Pat. No. 10,746,750, filed Sep. 24, 2021, 24 pages.
Patent Owner's Response to the Decision to Institute Inter Partes Review of U.S. Pat. No. 9,272,280 B2, [Paper 19], dated Dec. 1, 2017, [IPR2017-00852] 39 pages.
Patent Owner's Response to the Decision to Institute Inter Partes Review of U.S. Pat. No. 9,410,971, entered Dec. 1, 2017, 59 pages.
Patent Owner's Sur-Reply for IPR2018-00950 [Paper 21] of U.S. Pat. No. 9,915,671, filed May 6, 2019, 34 pages. [Exhibit 1031].
Patent Owner's Updated Exhibit List for Inter Partes Review of U.S. Pat. No. 9,272,280 B2, [Paper 10], dated Jun. 30, 2017, 2 pages.
Patent Owner's Updated Exhibit List for Inter Partes Review of U.S. Pat. No. 9,272,280 B2, [Paper 20], dated Dec. 1, 2017, [IPR2017-00852] 3 pages.
Patent Owner's Updated Exhibit List for Inter Partes Review of U.S. Pat. No. 9,410,971, dated Dec. 1, 2017, 4 pages.
Patent Owner's Updated Exhibit List for Inter Partes Review of U.S. Pat. No. 9,410,971, dated Jun. 30, 2017, 2 pages.
Patent Owner's Updated Mandatory Notices for Inter Partes Review of U.S. Pat. No. 9,272,280 B2, [Paper 7 / IPR2017-00852], dated Jun. 8, 2017, 4 pages.
Patent Owner's Updated Mandatory Notices for Inter Partes Review of U.S. Pat. No. 9,272,280 B2, dated Jun. 22, 2017, [Paper 8 / IPR2017-00852] 4 pages.
Patent Owner's Updated Mandatory Notices for Inter Partes Review of U.S. Pat. No. 9,272,280 B2, dated Jun. 5, 2018, [Paper 38 / IPR2017-00852], 4 pages.
Patent Owner's Updated Mandatory Notices for Inter Partes Review of U.S. Pat. No. 9,410,971, dated Jun. 22, 2017, 4 pages.
Patent Owner's Updated Mandatory Notices for Inter Partes Review of U.S. Pat. No. 9,410,971, dated Jun. 8, 2017, 3 pages.
Patent Owner's Updated Mandatory Notices for Inter Partes Review of U.S. Pat. No. 9,915,671, dated Jun. 8, 2018, 3 pages.
Pertinent Materials reviewed & considered by James P. Landers, For Inter Partes Review of U.S. Pat. No. 10,031,144 dated May 28, 2019, 2 pages.

(56) References Cited

OTHER PUBLICATIONS

Pertinent Materials reviewed & considered by James P. Landers, For Inter Partes Review of U.S. Pat. No. 9,977,039 dated May 28, 2019, 2 pages.
Pertinent Materials reviewed & considered by Scott Diamond, Ph.D., For Inter Partes Review of U.S. Pat. No. 9,272,280 dated Jan. 9, 2018, 2 pages.
Pertinent Materials reviewed & considered by Scott Diamond, Ph.D., For Inter Partes Review of U.S. Pat. No. 9,410,971 dated Jan. 18, 2018, 2 pages.
Pertinent Materials reviewed & considered by Scott Diamond, Ph.D., For Inter Partes Review of U.S. Pat. No. 9,915,671 dated Apr. 15, 2019, 2 pages.
Pertinent Materials Reviewed and Considered by Keith Neeves, Ph.D. filed on Dec. 14, 2020 [IPR2021-00293 / U.S. Pat. No. 10,746,750], 3 pages [Exhibit 1019].
Petition for Inter Partes Review of U.S. Pat. No. 10,746,750 dated Dec. 14, 2020 [Paper 2], of Request for Ex Parte Reexamination filed by a Third Party Requester, Nov. 3, 2021, 79 pages [IPR2021-00293].
Petition for Inter Partes Review of U.S. Pat. No. 9,915,671 dated Apr. 20, 2018 [Paper 2], of Request for Ex Parte Reexamination filed by a Third-Party Requester, Nov. 3, 2021, 76 pages [IPR2018-00950].
Petition for Inter Partes Review of U.S. Pat. No. 9,272,280 B2, dated Feb. 3, 2017, 28 pages.
Petition for Inter Partes Review of U.S. Pat. No. 9,410,971 B2, dated Feb. 3, 2017, 51 Pages.
Petition for Inter Partes Review of U.S. Pat. No. 9,410,971 B2, dated Nov. 30, 2017, 74 pages.
Petition for Post-Grant Review of U.S. Pat. No. 10,031,144, dated Apr. 24, 2019, 104 pages.
Petition for Post-Grant Review of U.S. Pat. No. 9,977,039, dated Feb. 21, 2019, 95 pages.
Petitioner's Motion to Submit Supplemental Information for Inter Partes Review of U.S. Pat. No. 9,272,280 B2, dated May 22, 2018, 11 pages.
Petitioner's Motion to Submit Supplemental Information for Inter Partes Review of U.S. Pat. No. 9,410,971, dated May 22, 2018, 11 pages.
Petitioner's Motion to Withdraw Grounds for Inter Partes Review of U.S. Pat. No. 9,410,971, dated Jun. 1, 2018, 6 pages.
Petitioner's Objection to Patent Owner's Demonstratives for Inter Partes Review of U.S. Pat. No. 9,410,971, dated Aug. 10, 2018, 6 pages.
Petitioner's Objections to Patent Owner's Demonstratives for Inter Partes Review of U.S. Pat. No. 9,272,280 B2, dated Aug. 10, 2018, 6 pages.
Petitioner's Objections to Patent Owner's Demonstratives for Inter Partes Review of U.S. Pat. No. 9,272,280 B2, dated Jun. 8, 2018, 4 pages.
Petitioner's Opposition to Patent Owner's Motion to Submit Supplemental Information for Inter Partes Review of U.S. Pat. No. 9,915,671, dated May 28, 2019, 71 pages.
Petitioner's Reply to Patent Owner's Objection to Motion to Withdraw for Inter Partes Review of U.S. Pat. No. 9,410,971, dated Jun. 15, 2018, 8 pages.
Petitioner's Reply to Patent Owner's Response for Inter Partes Review of U.S. Pat. No. 9,410,971, dated Mar. 1, 2018, 25 pages.
Petitioner's Reply to Patent Owner's Response for Inter Partes Review of U.S. Pat. No. 9,915,671, dated Apr. 4, 2019, 32 pages.
Petitioner's Reply to Patent Owner's Response of U.S. Pat. No. 9,272,280 dated Mar. 1, 2018, 17 pages.
Petitioner's Reply to Patent Owner's Response under 37 C.F.R. §42.120 for IPR2021-00293 of U.S. Pat. No. 10,746,750, filed Dec. 16, 2021, 30 pages.
Petitioner's Request for Oral Argument for Inter Partes Review of U.S. Pat. No. 9,272,280, dated Apr. 23, 2018, 3 pages.
Petitioner's Request for Oral Argument for Inter Partes Review of U.S. Pat. No. 9,410,971, dated Apr. 23, 2018, 3 pages.
Petitioner's Request for Oral Argument for Inter Partes Review of U.S. Pat. No. 9,915,671, dated May 29, 2019, 3 pages.
Petitioner's Request for Refund for Inter Partes Review of U.S. Pat. No. 9,410,971, dated May 26, 2018, 3 pages.
Petitioner's Request for Rehearing for Inter Partes Review of U.S. Pat. No. 9,410,971, dated Sep. 15, 2017, 18 pages.
Petitioner's Supplemental Reply for Inter Partes Review of U.S. Pat. No. 9,272,280 B2 dated May 18, 2018, 10 pages.
Petitioner's Supplemental Reply in view of Apr. 26, 2018 Institution of Previously Non-Instituted Grounds for Inter Partes Review of U.S. Pat. No. 9,410,971, dated May 18, 2018, 15 pages.
Petitioner's Supplemental Request for Oral Argument for Inter Partes Review of U.S. Pat. No. 9,272,280 B2, dated Aug. 2, 2018, 3 pages.
Petitioner's Updated Exhibit List for Inter Partes Review of U.S. Pat. No. 9,272,280 B2, dated Mar. 1, 2018, 4 pages.
Petitioner's Updated Exhibit List for Inter Partes Review of U.S. Pat. No. 9,410,971, dated Mar. 1, 2018, 3 pages.
Petitioner's Updated Mandatory Notices for Inter Partes Review of U.S. Pat. No. 9,272,280 B2, dated Jun. 8, 2018, 3 pages.
Preliminary Amendment filed in U.S. Appl. No. 15/357,492, as filed for Inter Partes Review of U.S. Pat. No. 9,915,671, [IPR2018-00950], 34 pages.
Provisional Application (filed Feb. 15, 2011; U.S. Appl. No. 61/443,088) for Inter Partes Review of U.S. Pat. No. 9,977,039, 46 pages.
Record of Oral Hearing for Inter Partes Review of U.S. Pat. No. 9,272,280 B2 [IPR2018-00852] and U.S. Pat. No. 9,410,971 B2 [IPR2017-00855] dated Jun. 12, 2018, 46 pages.
Record of Oral Hearing for Inter Partes Review of U.S. Pat. Nos. 9,272,280B2 [IPR2017-00852] and U.S. Pat. No. 9,410,971B2 [IPR2017-00855], dated Aug. 14, 2018, 34 pages.
Reply Declaration of Scott Diamond, Ph.D., for Inter Partes Review of U.S. Pat. No. 9,915,671 dated Apr. 3, 2019, 19 pages.
Request for Ex Parte Reexamination by third Party Requestor of U.S. Pat. No. 10,175,225, filed Jul. 15, 2022, (124 pages).
Request for Ex Parte Reexamination of U.S. Pat. No. 11,061,038 [U.S. Appl. No. 90/019,032] filed by a Third Party Requester Nov. 3, 2021, 340 pages.
Request for Rehearing of U.S. Pat. No. 9,915,671, filed Nov. 1, 2019, 15 pages [Exhibit 1032. IPR2018-00950].
Response to Notice of Filing for Inter Partes Review for Inter Partes Review of U.S. Pat. No. 9,410,971, dated May 5, 2017, 7 pages.
Scheduling Order for Inter Partes Review of U.S. Pat. No. 9,272,280 B2 dated Sep. 1, 2017, [Paper 15 / IPR2017-00852], 8 pages.
Scheduling Order for Inter Partes Review of U.S. Pat. No. 9,410,971, dated Sep. 1, 2017, 8 pages.
Scheduling Order for Inter Partes Review of U.S. Pat. No. 9,915,671, dated Oct. 5, 2018, 8 pages.
Scheduling Order for IPR2021-00293 [Paper 10] of U.S. Pat. No. 10,746,750, issued Jul. 1, 2021, 11 pages.
Statutory Terminal Disclaimer for IPR2021-00293 of U.S. Pat. No. 10,746,750, filed Apr. 22, 2021, 3 pages.
Third party observation filed in European Patent Application No. 11766842.6, dated Mar. 6, 2017, 10 pages.
Third Party Observation filed in European Patent Application No. 12865280.7, dated Nov. 23, 2016, 4 pages.
Third party observation filed in U.S. Appl. No. 15/202,059, filed Nov. 30, 2016, 40 pages.
Transmittal of Request for Ex Parte Reexamination of U.S. Pat. No. 11,061,038 filed by a Third Party Requester Jul. 13, 2021, 3 pages.
Prosecution History of the '225 Patent [U.S. Appl. No. 14/500,248] for Request for Ex Parte Reexamination of U.S. Pat. No. 10,175,225, filed Jul. 15, 2022, 1,670 pages [Exhibit 1002].
U.S. Pat. No. 10,175,225 McCluskey et al., ("the '225 Patent") for Request for Ex Parte Reexamination of U.S. Pat. No. 10,175,225, filed Jul. 15, 2022, 35 pages.
U.S. Pat. No. 11,061,038, issued Jul. 13, 2021, of Request for Ex Parte Reexamination filed by a Third Party Requester, Nov. 3, 2021, 39 pages.
U.S. Pat. No. 5,629,209, issued May 13, 1997, of Request for Ex Parte Reexamination filed by a Third Party Requester, Nov. 3, 2021, 39 pages.

(56) References Cited

OTHER PUBLICATIONS

U.S. Pat. No. 6,016,712, issued Jan. 25, 2000, of Request for Ex Parte Reexamination filed by a Third Party Requester, Nov. 3, 2021, 24 pages.
U.S. Pat. No. 6,613,286, issued Sep. 2, 2003, of Request for Ex Parte Reexamination filed by a Third Party Requester, Nov. 3, 2021, 20 pages.
U.S. Pat. No. 9,915,671, issued May 13, 2018, of Request for Ex Parte Reexamination filed by a Third Party Requester, Nov. 3, 2021, 25 pages.
U.S. Publication No. 20040189311A1, published Sep. 30, 2004, of Request for Ex Parte Reexamination filed by a Third Party Requester, Nov. 3, 2021, 91 pages.
U.S. Publication No. 20050220668A1 to Coville ("Coville"), published Oct. 6, 2005, of Request for Ex Parte Reexamination filed by a Third Party Requester, Nov. 3, 2021, 18 pages.
U.S. Publication No. 20050233460A1, published Oct. 20, 2005, of Request for Ex Parte Reexamination filed by a Third Party Requester, Nov. 3, 2021, 32 pages.
U.S. Publication No. 20100154520 to Schubert et al. ("Schubert") for Request for Ex Parte Reexamination of U.S. Pat. No. 10,175,225, filed Jul. 15, 2022, 20 pages.
U.S. Publication No. 20100190193 to Calatziz et al. ("Calatziz") for Request for Ex Parte Reexamination of U.S. Pat. No. 10,175,225, filed Jul. 15, 2022, 13 pages.
U.S. Publication No. 20120329082 to Viola et al. ("Viola") for Request for Ex Parte Reexamination of U.S. Pat. No. 10,175,225, filed Jul. 15, 2022, 28 pages.
U.S. Publication No. 20150260735 to Delmenico et al. ("Delmenico") for Request for Ex Parte Reexamination of U.S. Pat. No. 10,175,225, filed Jul. 15, 2022, 11 pages.
Certificate of Correction for U.S. Pat. No. 10,031,144 filed on Apr. 24, 2019, Exhibit 1003 to PGR2019-00047.
Certificate of Correction for U.S. Pat. No. 9,977,039 filed on Feb. 21, 2019, Exhibit 1003 to PGR2019-00033.
Decision Denying Institution of Post-Grant Review filed on Aug. 23, 2019 for PGR2019-00033, 26 pgs.
Decision Denying Institution of Post-Grant Review filed on Oct. 24, 2019 for PGR2019-00047, 29 pages.
Decision Denying Petitioner's Request for Rehearing filed on Nov. 8, 2019 for U.S. Pat. No. 9,977,093 [PGR2019-00033], 13 pages.
Email from Trials@USPTO.gov Gabriel Goldman on Jun. 5, 2019, Exhibit 1015 to PGR2019-00033, 5 pages.
Final Written Decision filed on Apr. 24, 2019, Exhibit 1028 to PGR2019-00047.
Final Written Decision filed on Apr. 24, 2019, Exhibit 1029 to PGR2019-00047.
Final Written Decision filed on Feb. 21, 2019, Exhibits 1011 and 1012 to PGR2019-00033.
Gabriel Goldman email to the Patent Trial and Appeal Board on Jun. 3, 2019, Exhibit 1014 to PGR2019-00033, 3 pages.
Patent Owner's Notice of Appeal filed on Feb. 4, 2020 for IPR2018-00950.
Pertinent Materials Reviewed and Considered by James P. Landers, Ph.D filed on Jul. 29, 2019, Exhibit 2003 to PGR2019-00047.
Provisional Application for Patent Cover Sheet filed on Apr. 24, 2019, Exhibit 1004 to PGR2019-00047.
Request for Rehearing and Request to Enter New Exhibits filed on Sep. 22, 2019 for PGR2019-00033, 21 pages.
Table of Prior Art Devices filed on Feb. 3, 2017 [Exhibit 1010 to IPR2017-00852].
Examination Report issued in Australian Application No. 2017248548, dated Jul. 9, 2018, 3 pages.
Examination Report issued in Australian Application No. 2012364908, dated Jul. 23, 2016, 4 pages.
Examination Report issued in Australian Application No. 2012364908, dated Jun. 27, 2017, 5 pages.
Examination Report No. 1 issued in Australian Application No. 2021200600, dated Mar. 17, 2021, 5 pages.
Examination Report No. 2 issued in Australian Application No. 2016364931, dated Mar. 4, 2019, 4 pages.
Examination Report in Australian Application No. 2022201777 dated May 16, 2023, 2 pages.
Examiner Requisition for Canadian Patent Application No. 3,033,000, dated Apr. 15, 2020, 4 pages.
Office Action issued for Canadian Application No. 2,823,729, dated Mar. 9, 2018, 4 pages.
Office Action issued for Canadian Application No. 2,823,729, dated Nov. 14, 2018, 4 pages.
Office Action for Chinese Application No. 2016800743389, dated Apr. 23, 2020, 16 pages, (with English translation).
Office Action in Chinese Application No. 200980151858.5, dated Jan. 16, 2014, w/English translation (Feb. 14, 2014), 4 pages.
Office Action in Chinese Application No. 200980151858.5, dated May 21, 2013, 16 pages.
Office Action in Chinese Application No. 201680074338.9, dated Feb. 3, 2019, 4 pages (w/out English translation).
Search Report in Chinese Application No. 201680074338.9, dated Jan. 25, 2019, 3 pages (w/out English translation).
Office Action in Chinese Application No. 2016800743389 dated Aug. 12, 2019, 13 pages, with English translation.
Office Action in Chinese Application No. 201880056029.8, dated Sep. 15, 2020, 12 pages (with concise explanation of relevance).
Extended European Search Report in EP Application No. 08172769.5 dated Jun. 4, 2009, 11 pages.
Office Action in EP Application No. 08172769.5, dated Jun. 1, 2011, 4 pages.
Extended European Search Report in EP Application No. 12179576.9, dated Oct. 5, 2012, 5 pages.
Communication pursuant to Article 94(3) in EP Application No. 12179576.9, dated May 22, 2013, 2 pages.
Extended European Search Report in EP Application No. 13163014.7, dated May 23, 2013, 3 pages.
Extended European Search Report in EP Application No. 13167983.9, dated Nov. 6, 2013, 3 pages.
Extended European Search Report in EP Application No. 13167979.7, dated Nov. 6, 2013, 5 pages.
Communication pursuant to Article 94(3) in EP Application No. 13163014.7, dated Mar. 24, 2014, 3 pages.
Extended European Search Report issued in European Patent Application No. 11766842.6, dated Oct. 21, 2015, 9 pages.
Extended European Search Report and Opinion for Application No. 15187347.8, Jun. 1, 2016, 21 pages.
Extended Search Report issued in European Patent Application No. 12865280.7, dated Oct. 24, 2016, 5 pages.
Communication pursuant to Article 94(3) in EP Application No. 13167979.7, dated Nov. 15, 2016, 3 pages.
Communication pursuant to Rule 114(2) EPC issued in European Patent Application No. 12865280.7, dated Dec. 13, 2016, 5 pages.
Communication pursuant to Rule 94(3) EPC issued in European Patent Application No. 12865280.7, dated Jul. 3, 2017, 3 pages.
Communication pursuant to Article 94(3) EPC dated Apr. 3, 2018 in EP Application No. 12865280.7, 3 pages.
Communication Pursuant to Article 94(3) EPC for European Application No. 12865280.7, dated Oct. 8, 2018 for Inter Partes Review of U.S. Pat. No. 9,915,671, 4 pages.
Response to EPO Communication Pursuant to Article 94(3) EPC for European Application No. 12865280.7, dated Feb. 18, 2019 for Inter Partes Review of U.S. Pat. No. 9,915,671, 13 pages.
Partial European Search Report in EP Application No. 18193752.5, dated Feb. 12, 2019, 15 pages.
Communication Pursuant to Article 94(3) EPC issued for European Application No. 12865280.7, dated Mar. 18, 2019, 7 pages.
Extended European Search Report in Application No. EP18193752.5, dated May 13, 2019, 13 pages.
Extended European Search Report in Application No. EP16871654.6, dated May 27, 2019, 7 pages.
Extended European Search Report for European Patent Application No. 17847520.8, dated Feb. 27, 2020, 7 pages.
Communication under Article 94(3) EPC for EP Patent Application No. 20175351.4, issued Feb. 15, 2022, with English summary (4 pages).

(56) References Cited

OTHER PUBLICATIONS

Communication pursuant to Article 94(3) EPC in Application No. 20175351.4 dated Mar. 13, 2023, 5 pages.
Communication pursuant to Article 94(3) EPC in Application No. 18193752.5 dated Mar. 1, 2023, 5 pages.
European Search Report in corresponding application No. 20175351.4 dated Sep. 21, 2020 (8 pages).
International Search Report and Written Opinion in Application No. PCT/EP2009/067181, dated Mar. 22, 2010, 12 pages.
International Search Report & Written Opinion of the International Searching Authority, received in corresponding application No. PCT/US2010/049342, dated Nov. 16, 2010, 13 pgs.
International Preliminary Report on Patentability for PCT/EP2009/067181, dated Jun. 29, 2011, 9 pages.
International Search Report & Written Opinion of the International Searching Authority, received in corresponding application No. PCT/US2011/031832, dated Dec. 15, 2011, 9 pgs.
International Preliminary Report on Patentability & Written Opinion, dated Mar. 20, 2012, in connection with International Application No. PCT/US2010/049342, 12 pgs.
International Preliminary Report on Patentability & Written Opinion, dated Oct. 9, 2012, in connection with International Application No. PCT/US2011/031832, 6 pgs.
International Search Report, dated Jan. 2, 2013, in connection with International Application No. PCT/US2012/038553, 7 pgs.
International Search Report, dated Aug. 20, 2013, in connection with International Application No. PCT/US2012/025278, 13 pgs.
International Preliminary Report on Patentability & Written Opinion, dated Aug. 27, 2013, in connection with International Application No. PCT/US2012/025278, 9 pgs.
International Search Report, dated Sep. 30, 2013, in connection with International Application No. PCT/US2012/025270, 16 pgs.
International Preliminary Report on Patentability & Written Opinion, dated Oct. 8, 2013, in connection with International Application No. PCT/US2012/025270, 12 pgs.
International Preliminary Report on Patentability & Written Opinion, dated Nov. 19, 2013, in connection with International Application No. PCT/US2012/038553, 5 pgs.
International Search Report & Written Opinion for International Application No. PCT/US2016/034501, dated Aug. 31, 2016, 10 pages.
International Search Report and Written Opinion in Application No. PCT/US2016/064790, Feb. 15, 2017, 17 pages.
International Search Report and Written Opinion in Application No. PCT/US2016/064797, Feb. 15, 2017, 16 pages.
International Search Report and Written Opinion in Application No. PCT/US2016/064806, Feb. 15, 2017, 18 pages.
International Search Report and Written Opinion in Application No. PCT/US2016/064800, Feb. 16, 2017, 14 pages.
International Search Report & Written Opinion for International Application No. PCT/US2017/049505, dated Nov. 2, 2017, 8 pages.
International Search Report & Written Opinion for International Application No. PCT/US2018/040120, dated Sep. 20, 2018, 7 pages.
Notifications of Reasons for Refusal in Japanese Application No. 2011-541392, dated Jun. 14, 2013, 4 pages.
Notifications of Reasons for Refusal in Japanese Application No. 2014-165975, dated Jul. 17, 2015, 8 pages.
Notification of Reasons for Refusal in Japanese Application No. 2015-237571, dated Nov. 7, 2016, 5 pages.
Notification of Reasons for Refusal in Japanese Application No. 2015-191180, dated Nov. 17, 2017, (9 pages including English Translation).
Notice of Rejection in Japanese Application No. 2018-528982 dated Jul. 2, 2019, 14 pages, with English translation.
Notification of Reasons for Refusal in Japanese Application No. 2019-001775, dated Jan. 31, 2020, 13 pages, with English translation.
Official Notice of Rejection in Japanese Patent Application No. 2020-501278, dated Jul. 14, 2020, 8 pages (with English translation).
Notice of Rejection in Japanese Application No. 2019-215835 dated Jul. 20, 2021, 8 pages (English translation).
Official Notice of Rejection in Japanese Patent Application No. 2021-210802 dated Jan. 17, 2023 (with English translation), 9 pages.
Notification of Reasons for Refusal for Japanese Patent Application No. 2021-143317, dated Aug. 29, 2022 (with English translation), 4 pages.
Notification of Reasons for Refusal in Japanese Application No. 2015-132034 dated Jul. 22, 2016 (5 pages).
Office Action in Korean Application No. 1020117017187, dated Mar. 28, 2016, 11 pages.
Office Action in Korean Application No. 1020167029191, dated Nov. 17, 2016, 5 pages.
Information Disclosure Statement accompanying Request for Ex Parte Reexamination of U.S. Pat. No. 11,061,038 filed by a Third Party Requester Nov. 3, 2021, 2 pages.
Action and Response History in U.S. Appl. No. 12/640,376 [now U.S. Pat. No. 8,448,499], downloaded Jun. 14, 2023, 47 pages.
Action and Response History in U.S. Appl. No. 13/895,034 [now U.S. Pat. No. 9,285,377], downloaded Jun. 14, 2023, 42 pages.
Action and Response History in U.S. Appl. No. 15/066,605 [now U.S. Pat. No. 9,739,789], downloaded Jun. 14, 2023, 38 pages.
Action and Response History in U.S. Appl. No. 15/357,492 [now U.S. Pat. No. 9,915,671], downloaded Jun. 14, 2023, 177 pages.
Action and Response History in U.S. Appl. No. 15/869,782, downloaded Jun. 14, 2023, 17 pages.
Action and Response History in U.S. Appl. No. 16/146,333 [now U.S. Pat. No. 10,746,750], downloaded Jun. 14, 2023, 165 pages.
Action and Response History in U.S. Appl. No. 16/520,006 [now U.S. Pat. No. 11,131,680], downloaded Jun. 14, 2023, 143 pages.
Action and Response History in U.S. Appl. No. 16/520,004 [now U.S. Pat. No. 10,996,230], downloaded Jun. 14, 2023, 114 pages.
Action and Response History in U.S. Appl. No. 17/182,502 [now U.S. Pat. No. 11,061,038], downloaded Jun. 14, 2023, 51 pages.
Action and Response History in U.S. Appl. No. 17/372,637 [now U.S. Pat. No. 11,360,106], downloaded Jun. 14, 2023, 64 pages.
Action and Response History in U.S. Appl. No. 17/393,036, downloaded on Oct. 31, 2023, 60 pages.
Action and Response History in U.S. Appl. No. 17/831,845 [now U.S. Pat. No. 11,768,211], downloaded Oct. 31, 2023, 54 pages.
Action and Response History in U.S. Appl. No. 14/500,248 [now U.S. Pat. No. 10,175,225], downloaded Jun. 14, 2023, 77 pages.
Action and Response History in U.S. Appl. No. 14/958,876 [now U.S. Pat. No. 10,288,630], downloaded Jun. 14, 2023, 65 pages.
Action and Response History in U.S. Appl. No. 14/958,878 [now U.S. Pat. No. 10,539,579], downloaded Jun. 14, 2023, 80 pages.
Action and Response History in U.S. Appl. No. 14/958,889 [now U.S. Pat. No. 10,816,559], downloaded Jun. 14, 2023, 137 pages.
Action and Response History in U.S. Appl. No. 14/958,890 [now U.S. Pat. No. 9,897,618], downloaded Jun. 14, 2023, 42 pages.
Action and Response History in U.S. Appl. No. 16/201,522 [now U.S. Pat. No. 11,327,069], downloaded Jun. 14, 2023, 108 pages.
Action and Response History in U.S. Appl. No. 17/343,960 [now U.S. Pat. No. 11,719,688], downloaded Jun. 14, 2023, 105 pages.
Action and Response History in U.S. Appl. No. 16/572,567, downloaded on Oct. 31, 2023, 97 pages.
Action and Response History in U.S. Appl. No. 15/648,345 [now U.S. Pat. No. 10,843,185], downloaded Jun. 14, 2023, 58 pages.
Action and Response History in U.S. Appl. No. 15/904,984 [now U.S. Pat. No. 10,481,168], downloaded Jun. 14, 2023, 238 pages.
Action and Response History in U.S. Appl. No. 15/991,677 [now U.S. Pat. No. 10,161,944], downloaded Jun. 14, 2023, 41 pages.
Action and Response History in U.S. Appl. No. 15/202,059 [now U.S. Pat. No. 10,031,144], downloaded Jun. 14, 2023, 162 pages.
Action and Response History in U.S. Appl. No. 15/644,124 [now U.S. Pat. No. 9,977,039], downloaded Jun. 14, 2023, 142 pages.
Action and Response History in Reexam U.S. Appl. No. 90/019,032, downloaded on Jun. 15, 2023, 570 pages.

(56) References Cited

OTHER PUBLICATIONS

Action and Response History in Reexam U.S. Appl. No. 90/019,098, downloaded on Oct. 31, 2023, 233 pages.
Action and Response History in U.S. Appl. No. 13/397,398 [now U.S. Pat. No. 9,272,280], downloaded Jun. 14, 2023, 221 pages.
Action and Response History in U.S. Appl. No. 18/089,505, downloaded on Oct. 31, 2023, 18 pages.
Non-Final Office Action in U.S. Appl. No. 18/211,917 dated Oct. 31, 2023, 14 pages.
Reply to Non-Final Office Action in U.S. Appl. No. 18/211,917 dated Dec. 5, 2023, 4 pages.
Action and Response History in U.S. Appl. No. 16/708,334, downloaded on Oct. 31, 2023, 56 pages.
Non-Final Rejection in Reexamination U.S. Appl. No. 90/019,032 dated Apr. 26, 2022 (18 pages).
Interview Summary and Amendment in Reply to Action of Apr. 26, 2022 and Declaration of Dr. Robert Hillman in Reexamination U.S. Appl. No. 90/019,032, filed Jul. 26, 2022 (65 pages).
Non-Final Rejection in Reexamination U.S. Appl. No. 90/019,032 dated Sep. 29, 2022 (61 pages).
Interview Agenda in Reexamination U.S. Appl. No. 90/019,032 dated Nov. 10, 2022 (20 pages).
Interview Summary and Amendment in Reply to Action of Sep. 29, 2022 and Declaration of Dr. Gerald G. Fuller in Reexamination U.S. Appl. No. 90/019,032, filed Nov. 29, 2022 (218 pages).
Final Rejection in Reexamination U.S. Appl. No. 90/019,032 dated Jan. 27, 2023 (27 pages).
Examiner Interview Summary in Reexamination U.S. Appl. No. 90/019,032 dated Mar. 2, 2023 (9 pages).
Interview Summary and Amendment in Reply to Action of Jan. 27, 2023 and Declaration of Dr. Gerald G. Fuller in Reexamination U.S. Appl. No. 90/019,032, filed Mar. 27, 2023 (148 pages).
Advisory Action in Reexamination U.S. Appl. No. 90/019,032 dated Apr. 12, 2023 (5 pages).
Extended European Search Report in Application No. 23201178.3 dated Jan. 31, 2024, 11 pages.
Reply to Office Action in U.S. Appl. No. 18/089,505, filed Feb. 6, 2024, 12 pages.
Cimbala, J., "Introduction to Pressure in Fluid Mechanics," Learning Module, The Pennsylvania State University, [online] Retrieved from the Internet <URL:https://www.me.psu.edu/cimbala/Learning/Fluid/Pressure/pressure_basics.htm> [retrieved on Jan. 22, 2024], 3 pages.
Extended European Search Report in Application No. 24157405.2 dated May 14, 2024, 10 pages.
Notification of Reasons for Refusal in Japanese Application No. 2023-082050 dated Mar. 22, 2024 [with English translation], 5 pages.

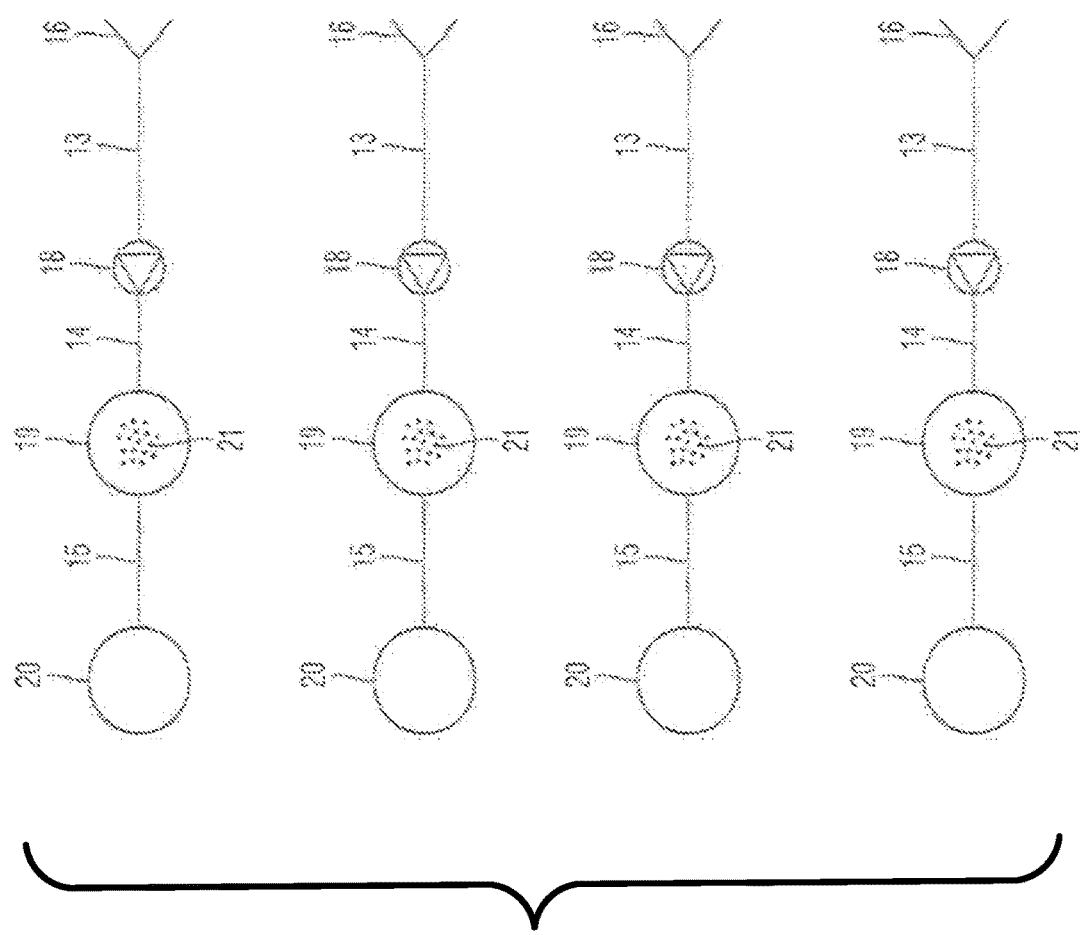
FIG. 16 (NEW)

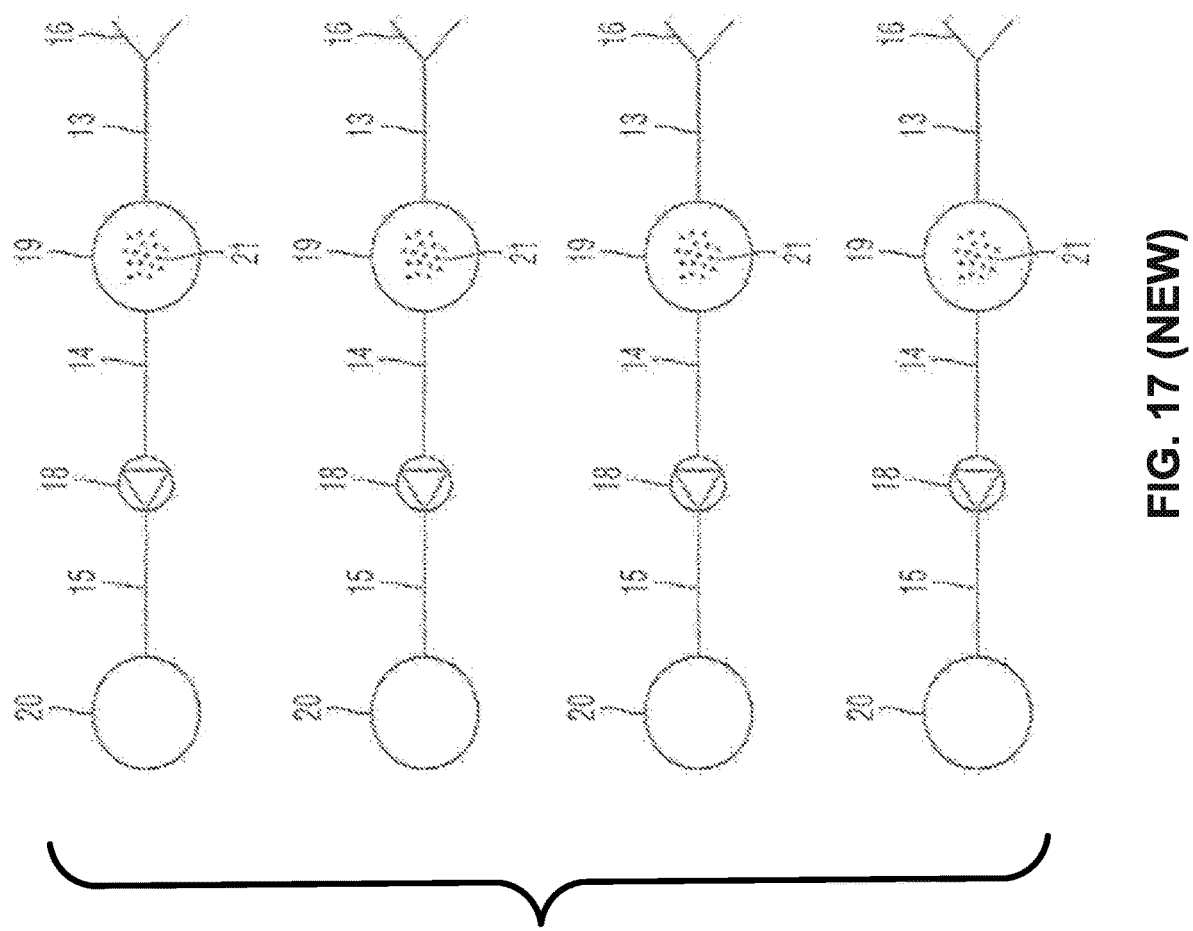
FIG. 17 (NEW)

CARTRIDGE DEVICE FOR A MEASURING SYSTEM FOR MEASURING VISCOELASTIC CHARACTERISTICS OF A SAMPLE LIQUID, A CORRESPONDING MEASURING SYSTEM, AND A CORRESPONDING METHOD

CROSS-REFERENCE TO RELATED APPLICATIONS

This application is a continuation application and claims the benefit of co-pending U.S. application Ser. No. 17/831,845, which was filed on Jun. 3, 2022, which is a continuation and claims the benefit of U.S. application Ser. No. 17/372,637 filed on Jul. 12, 2021 now U.S. Pat. No. 11,360,106 issued on Jun. 14, 2020, which is a continuation of and claims the benefit of U.S. application Ser. No. 17/182,502 filed on Feb. 23, 2021, now U.S. Pat. No. 11,061,038 issued on Jul. 13, 2020, which is a continuation of and claims the benefit of U.S. patent application Ser. No. 16/520,004 filed Jul. 23, 2019, now U.S. Pat. No. 10,996,230 issued on May 4, 2021, which is a continuation of and claims the benefit of U.S. application Ser. No. 16/146,333, filed Sep. 28, 2018, now U.S. Pat. No. 10,746,750, which is a continuation of and claims the benefit U.S. application Ser. No. 15/869,782, filed Jan. 12, 2018, which is a continuation of and claims the benefit of U.S. application Ser. No. 15/357,492, filed Nov. 21, 2016, now U.S. Pat. No. 9,915,671, issued on Mar. 13, 2018, which is a continuation of and claims the benefit of U.S. application Ser. No. 15/066,605, filed Mar. 10, 2016, now U.S. Pat. No. 9,739,789, issued on Aug. 22, 2017, which is a continuation of and claims the benefit of U.S. application Ser. No. 13/895,034, filed on May 15, 2013, now U.S. Pat. No. 9,285,377, issued on Mar. 15, 2016, which is a continuation of and claims the benefit of U.S. application Ser. No. 12/640,376, filed on Dec. 17, 2009, now U.S. Pat. No. 8,448,499 issued on May 28, 2013, which claims priority to and the benefit of U.S. Provisional Application No. 61/140,344 filed on Dec. 23, 2008. This application is related to co-pending U.S. application Ser. No. 17/393,036 filed Aug. 3, 2021, to U.S. application Ser. No. 16/520,006 filed Jul. 23, 2019 now U.S. Pat. No. 11,131,680, issued on Jul. 13, 2021, to U.S. application Ser. No. 13/895,053 filed on May 15, 2013, now U.S. Pat. No. 9,086,423, issued on Jul. 21, 2015, to U.S. application Ser. No. 13/895,002, filed on May 15, 2013, now U.S. Pat. No. 8,857,244 issued on Oct. 14, 2014, and to U.S. application Ser. No. 13/894,998, filed on May 15, 2013, now U.S. Pat. No. 9,110,084 issued on Aug. 18, 2015, which are continuation applications of and claim the benefit of U.S. application Ser. No. 12/640,376, filed on Dec. 17, 2009, now U.S. Pat. No. 8,448,499 issued on May 28, 2013, which claims priority to and the benefit of U.S. Provisional Application Ser. No. 61/140,344 filed on Dec. 23, 2008. The entire contents of each of the above patents and applications are incorporated herein in their entirety by reference for all purposes.

FIELD OF THE INVENTION

The present invention relates to a cartridge device for a measuring system for measuring viscoelastic characteristics of a sample liquid, in particular of a blood sample liquid. The present invention also relates to a corresponding measuring system and method.

It is essential for survival that a wound stops bleeding, i.e. that the body possesses an adequate mechanism for haemostasis. The process of blood clotting can be activated in the case of injuries or inflammations by either extrinsic or intrinsic factors, e.g. tissue factor (TF) or Hagemann factor (F XII), respectively. Both activation channels are continued in a common branch of the cascade resulting in thrombin formation. The thrombin itself finally initiates the formation of fibrin fibres which represent the protein backbone of blood clots.

The other main constituent of the final blood clot are the thrombocytes which are interconnected by the fibrin fibres and undergo a number of physiological changes during the process of coagulation. Within limits a lack of thrombocytes can be substituted by an increased amount of fibrin or vice versa. This is reflected in the observation that the thrombocyte counts as well as the fibrinogen concentration varies even within a healthy population Various methods have been introduced to assess the potential of blood to form an adequate clot and to determine the blood dots stability. Common laboratory tests such as thrombocyte counts or the determination of fibrin concentration provide information on whether the tested component is available in sufficient amount but lack in answering the question whether the tested component works properly under physiological conditions (e.g. the polymerisation activity of fibrinogen under physiological conditions can not be assessed by common optical methods). Besides that, most laboratory tests work on blood-plasma and therefore require an additional step for preparation and additional time which is unfavourable especially under POC (point of care) conditions.

Another group of tests which overcomes these problems is summarized by the term "viscoelastic methods". The common feature of these methods is that the blood clot firmness (or other parameters dependent thereon) is continuously determined, from the formation of the first fibrin fibres until the dissolution of the blood clot by fibrinolysis. Blood clot firmness is a functional parameter, which is important for haemostasis in vivo, as a clot must resist blood pressure and shear stress at the site of vascular injury. Clot firmness results from multiple interlinked processes: coagulation activation, thrombin formation, fibrin formation and polymerization, platelet activation and fibrin-platelet interaction and can be compromised by fibrinolysis. Thus, by the use of viscoelastic monitoring all these mechanisms of the coagulation system can be assessed.

A common feature of all these methods used for coagulation diagnosis is that the blood clot is placed in the space between a cylindrical pin and an axially symmetric cup and the ability of the blood clot to couple those two bodies is determined.

The first viscoelastometric method was called "thrombelastography" (Hartert H: Blutgerinnungsstudien mit der Thrombelastographie, einem neuen Untersuchungsverfahren. Klin Wochenschrift 26:577-583, 1948). As illustrated in FIG. 1, in the thromboelastography, the sample as a sample liquid 1 is placed in a cup 2 that is periodically rotated to the left and to the right by about 5°, respectively. A probe pin 3 is freely suspended by a torsion wire 4. When a clot is formed it starts to transfer the movement of the cup 2 to the probe pin 3 against the reverse momentum of the torsion wire 4. The movement of the probe pin 3 as a measure for the clot firmness is continuously recorded and plotted against time. For historical reasons the firmness is measured in millimetres.

The result of a typical measurement of this kind is illustrated in FIG. 2. One of the most important parameters is the time between the activator induced start of the coagulation cascade and the time until the first long fibrin fibres have been build up which is indicated by the firmness signal exceeding a defined value. This parameter will be called clotting time or just CT in the following. Another important parameter is the clot formation time (CFT) which gives a measure for the velocity of the development of a clot. The CFT is defined as the time it takes for the clot firmness to increase from 2 to 20 mm. The maximum firmness a clot reaches during a measurement, further on referred to as maximum clot firmness or just MCF, Is also of great diagnostic importance.

Modifications of the original thromboelastography technique (Hartert et al. (U.S. Pat. No. 3,714,815) have been described by Cavallari et aL (U.S. Pat. No. 4,193,293), by Do et al. (U.S. Pat. No. 4,148,216), by Cohen (U.S. Pat. No. 6,537,819). A further modification by Calatzis et al. (U.S. Pat. No. 5,777,215) illustrated in FIG. 3 is known under the term thromboelastometry.

Contrary to the modifications mentioned above, thromboelastometry is based on a cup 2 fixed in a cup holder 12 while the probe pin 3 is actively rotated. For this purpose the probe pin 3 is attached to a shaft 6 which is suspended by a ball bearing 7 in a base plate 11 and has a spring 9 connected to it. An oscillating motion perpendicular to the drawing plane induced at the opposite end of the spring is transformed into a periodically rotation of the shaft 6 and the connected cup 2 around a rotation axis 5 by about 5° in each direction. As the sample liquid 1 begins to coagulate the motion amplitude of the shaft 6 which is detected by the deflection of a light beam from detecting means 10 and a mirror 9 starts to decrease.

During coagulation the fibrin backbone creates a mechanical elastic linkage between the surfaces of the blood-containing cup 2 and a probe pin 3 plunged therein. A proceeding coagulation process induced by adding one or more activating factor(s) can thus be observed. In this way, various deficiencies of a patient's haemostatic status can be revealed and can be interpreted for proper medical intervention.

A general advantage of viscoelastometric, e.g. thromboelastometric, techniques compared to other laboratory methods in this field therefore is that the coagulation process and the change of mechanical properties of the sample are monitored as a whole. This means that—in contrary to other laboratory methods mentioned above thromboelastometry does not only indicate if all components of the coagulation pathways are available in sufficient amounts but also if each component works properly.

To obtain detailed information on the correct amount and function of the thrombocytes as well as the fibrinogen and certain factors nowadays there is an increasing amount of compounds available which activate or inhibit certain components of the coagulation system. This allows determining at which point of the coagulation system a problem is located.

For practical reasons theses compounds are usually injected into the disposable plastic cup which later on is used for the measurement by using a pipette (either a manual or an automatic one). In the last preparation step, after the blood or plasma sample has been added, the whole amount of sample (blood/plasma and the additional chemicals) is mixed by drawing it into the pipette by and dispensing it into the cup again.

The possibility to activate or to inhibit certain components of the coagulation system is especially useful in conjunction with state-of-the-art thromboelastometers such as the ROTEM (Pentapharm GmbH, Munich, Germany) which allows conducting four measurements in parallel. This allows detailed information on the current status of the coagulation-situation of a patient to be achieved and therefore allows an appropriate therapy within several minutes.

This is of particular importance in case of patients struck by massive blood loss as it often occurs in context with multiple traumata or major surgery. The blood of such patients often is diluted due to infusions which are administered to replace the loss in volume. This leads to a decrease of the concentration of thrombocytes as well as coagulation factors including fibrinogen.

Main advantages of thromboelastometry and thromboelastography are the possibility to perform several differential tests in parallel in order to precisely determine which kinds of blood products are the appropriate medication, the possibility to perform the measurement at or close to the point of care (POC) and—compared to other methods—the relatively small amount of time until valid results are available.

On the other hand the operator has to perform a significant number of steps in order to start the measurement (preparation of the reagents, attachment of the probe pin and the cup to the instrument, pipeting and mixing the blood sample and the reagents, adjustment of computer settings, etc.) on which the time spent is considerable, especially in the case of surgery being performed.

Furthermore this rather complex preparation also increases the risk of operating errors. There have been several approaches to simplify the usage of thromboelastometers. The Rotem-System (Pentapharm GmbH, Munich, Germany)

e.g. is supplied with an automatic pipette which simplifies the handling to a large degree and thereby decreases the risk of operating errors.

WO 2008093216 describes the approach to provide the adequate amount of each of the reagents needed for one specific test in a ready-to-use mixture. In order to prevent the reaction of the reagents prior to the measurement, they are supplied in a lyophilisate state. This is additionally advantageous as the reagents can be stored at room temperature. Using this approach the preparation is reduced to the steps of adding the blood sample into the reagent container, mixing of blood with the reagent and transferring the mixture to the instrument.

US 2007/0059840 A1 describes a hemostasis analysis device and method. The device includes a container for holding a sample to be tested and a bobber configured to be buoyantly suspended on the sample. A magnet is secured to the bobber. The container can be driven in an oscillating motion. An external magnetic field is generated adjacent to the bobber. A magnetic field strength detector detects changes in the magnetic field as a result of movement of the bobber and magnet responsive to the oscillating motion of the container and clotting of the sample.

Such a new measuring system entails acceptability problems and uncertainties for a user. Moreover, that analysis device does not fit in existing measuring systems. Therefore new systems have to be completely designed.

All these modifications lead to a significant improvement of handling of modern thromboelastometers and thromboelastographs, however, no successful approach to develop a widely automated technique has been made since Hartert's invention 60 years ago. One of the two main reasons of that is the fact that the measurement requires two disposable parts (cup and pin) being moved in relation to each other and thus have to be reversibly attached to different parts of the measurement device.

E.g. in FIG. 3, the probe pin 3 is attached to the shaft 6 and the cup 2 to the cup holder 12, respectively. The other main reason is that different tests are required to get comprehensive information of a current bleeding status of a patient. These different tests require different reagents which have to be mixed with the blood sample.

SUMMARY OF THE INVENTION

It is a problem underlying the presented invention to provide a cartridge device for a measuring system for measuring viscoelastic characteristics of a sample liquid, in particular a blood sample.

Directly connected to this invention is the problem to provide a corresponding measuring system for measuring viscoelastic characteristics of a sample liquid, in particular the coagulation characteristics of a blood sample liquid.

It is a further problem underlying the invention to provide a method for measuring viscoelastic characteristics of a sample liquid using said measuring system.

These problems are solved by the subject-matter of the independent claims. Preferred embodiments are set forth in the dependent claims.

In a first aspect, the present invention provides a cartridge device for a measuring system for measuring viscoelastic characteristics of a sample liquid, in particular a blood sample, comprising
  a cartridge body having at least one measurement cavity formed therein and having at least one probe element arranged in said at least one measurement cavity for performing a test on said sample liquid; and
  a cover being attachable on said cartridge body;
  wherein said cover covers at least partially said at least one measurement cavity and forms a retaining element for retaining said probe element in a predetermined position within said at least one measurement cavity.

In a second aspect, the present invention provides a measuring system for measuring viscoelastic characteristics of a sample liquid, in particular a blood sample, comprising:
  at least one interface element; at least one shaft rotatably supported by the interface element to be rotated by drive means; at least one cartridge device fixed to the interface element for holding the sample liquid, the at least one cartridge device comprising a cartridge body with a cover and at least one probe element arranged in a measurement cavity formed in said cartridge body for cooperating with the at least one shaft; at least one detecting means cooperating with the shaft for measuring viscoelastic characteristics of the sample liquid; and control means to control the measuring system.

In a third aspect, the present invention provides a method for measuring viscoelastic characteristics of a sample liquid by means of said measuring system, comprising the following steps:
  a) providing the cartridge device having at least one measurement cavity with at least one probe element arranged therein;
  b) attaching the cartridge device to said interface element, said shaft being inserted into said probe element;
  c) filling said measurement cavity of said cartridge device with sample liquid;
  d) rotating said shaft in an oscillating motion around said rotation axis; and
  e) measuring viscoelastic characteristics of said sample liquid by detecting the rotation of said shaft by said detecting means.

In a preferred embodiment the probe element comprises a probe pin to cooperate with the sample liquid and a connector section for a connection to the measuring system. The connector section is formed e.g. as a bore extending within the probe element and comprises frictional connection means which can be e.g. clip means or a thread. An insertion guide facilitates an insertion of a part, in particular a shaft, of a measuring system. Thereby the shaft can be connected securely to the probe element.

The at least one measurement cavity can comprise bearing or supporting means for the probe element to align or hold the probe element prior to insertion of the shaft.

After the shaft has been inserted into the connector section, the shaft can be lifted to position the probe element at a working position.

In an alternative preferred embodiment the probe element is formed as a detachably fixed component part of the cover. An operator only has to attach the cartridge device to the measuring system the shaft being inserted into the probe element will detach the probe element from the cover and hold it securely in a position ready to carry out a measurement. Therefore the probe element comprises a fixing section for detachably fixing the probe element at fixing means of the cover.

After a measurement the cartridge device can be detached from the measuring system wherein the shaft is removed from the probe element. Then the probe element will seal the measurement cavity against the cover by means of e.g. a flange adapted to form a sealing. The cover retains the probe element within the measurement cavity.

It is preferred that the fixing means of the cover comprises clip means cooperating with corresponding clip means of the fixing section of the probe element.

In an alternative embodiment the fixing section of the probe element is integrally formed with the cover, the fixing means of the cover comprising a perforation.

The cover can be fixed on the cartridge body either by bonding or welding. In an alternative embodiment the cover is integrally formed with the cartridge body, e.g. made of a plastic material. It is also possible that the cover is made of a material which is different from the cartridge body. That can be done for example by two- or more-component-moulding.

In a further preferred embodiment the cartridge device further comprises at least one receiving cavity formed therein for receiving the sample liquid; at least one reagent cavity for holding at least one reagent; a ductwork connecting said cavities and the at least one measurement cavity; and at least one pump means connected to the ductwork for transporting the sample liquid from the at least one receiving cavity to the at least one measurement cavity by means of the ductwork, wherein the cover covers and at least partially forms said cavities and said ductwork and forms at least partially the pump means.

In a further embodiment the at least one reagent cavity is integrally formed with the pump means or/and with the at least one measurement cavity or/and with one or more of the ductworks. The reagent cavity can be formed as a deep cavity or just a small place where reagent can be deposited. Thus the sample liquid being pumped through the ductwork and the pump means into the measurement cavity can be mixed with the reagent.

The pump means comprise at least one valve for a directed flow of the sample liquid in order to direct the pumped liquid into the measurement cavity.

In another embodiment the reagent or an additional reagent can be stored in at least one reagent receptacle which can be opened by external means.

In a further embodiment the at least one reagent receptacle storing a reagent is integrated in the cover.

In another embodiment the at least one reagent receptacle comprises a bottom part which can be opened by external means to discharge the reagent into the ductwork and/or into one of the cavities. The receptacle can be adapted as a blister receptacle, for example.

The at least one reagent can be stored within the cartridge device in pulverized, solid or liquid form.

The cartridge device can be further provided with at least one reagent stored therein.

Filling in sample liquid can be done directly into the measurement cavity if no receiving cavity is provided. To this end the sample liquid can be injected through the cover via an opening or passage hole in the interface element or through a ductwork by an operator or by a control apparatus.

In case of a receiving cavity the sample liquid can be filled into the receiving cavity and be pumped by the pump means to the measuring cavity.

To fill in sample liquid, operate the pump means, add reagents and/or open the reagent receptacle the measuring system is equipped with a control apparatus. The control apparatus has means to access the pump means through a pump access formed as a passage of the interface element. Further the control apparatus can inject sample liquid through an inlet opening in the interface element into the receiving cavity. The control apparatus comprises also operating means to inject or to add reagents into the cartridge device as well as to open reagent receptacles.

Further features and advantages of the present invention will be evident from a description of embodiments with reference to the figures.

BRIEF DESCRIPTION OF THE DRAWINGS

The figures are showing the following:

FIG. 8a . . . c are technical drawings of the preferred probe element of FIG. 7a.

FIG. 9b is a sectional view B-B of the cartridge device of FIG. 9a.

FIG. 9c is a sectional view C-C of the cartridge device of FIG. 9a.

FIG. 9d is a sectional view D-D of the cartridge device of FIG. 9a.

FIG. 10a is a top view of the cartridge device of FIG. 9a.

FIG. 10b is a sectional view E-E of the cartridge device of FIG. 10a.

FIG. 11a is a sectional view of a pump means of the cartridge device of FIG. 9a.

FIG. 12 is a schematic top view of the pump means of FIG. 11a.

FIG. 13b is a top view of the measuring system of FIG. 13a.

FIG. 16 shows components of a cartridge having four arrangements of the type shown in FIG. 4.

FIG. 17 shows components of a cartridge having four arrangements of the type shown in FIG. 5.

DESCRIPTION OF EXEMPLARY EMBODIMENTS

Figure 1:
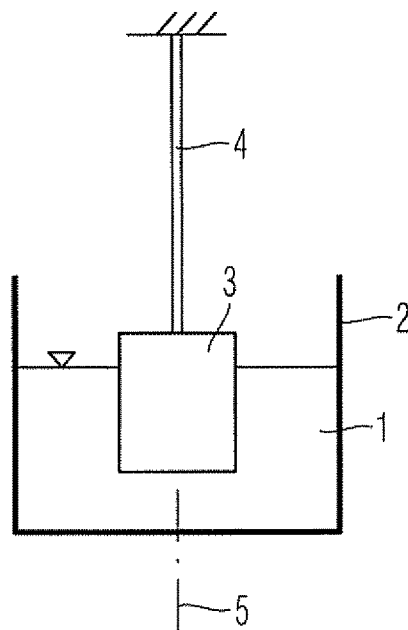
FIG. 1 is a schematic drawing of the principle of thromboelastography according to Hartert.
Figure 2:
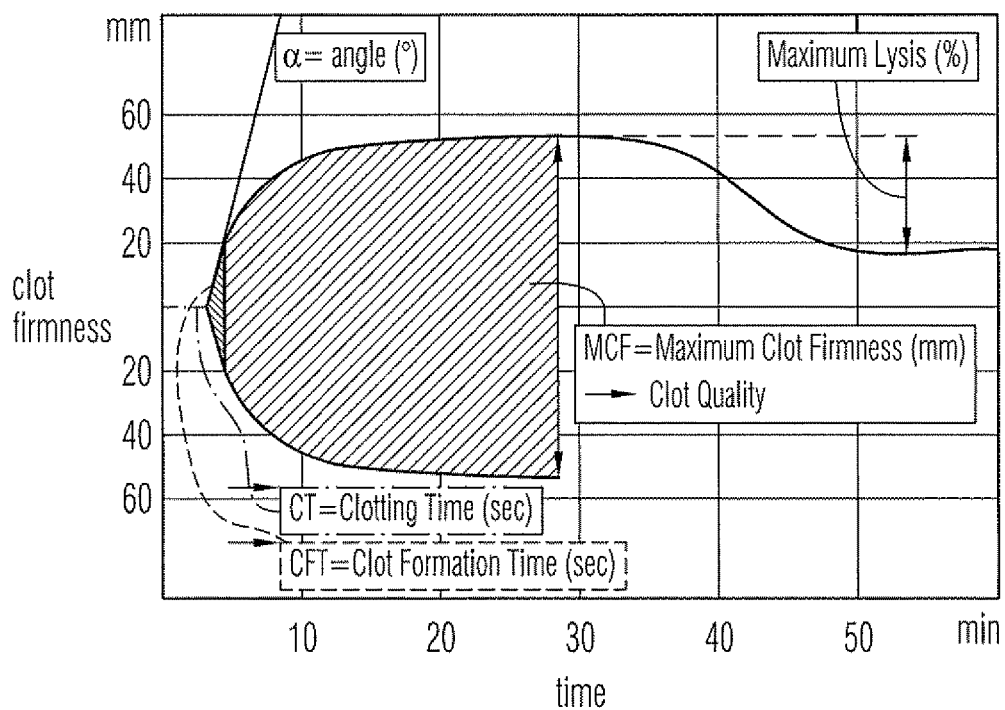
FIG. 2 is an exemplary diagram showing a typical thromboelastometric measurement.

Parts and components having same functions are depicted with same references.

Prior to a detailed description of the preferred embodiments the basic features and a basic practical implementation are summoned as follows. All embodiments refer to a cartridge device 50 (see FIG. 13c) which can be formed in a first embodiment (see FIGS. 4, 5 and 6), in a second embodiment (see FIGS. 7b, 7c and 15) or in a third embodiment (see FIGS. 9 to 10). The cartridge device 50 contains all parts coming into contact with a sample liquid 1 to be tested. These can be also reagents the sample liquid has to be mixed with for a measurement. The cartridge device 50 is part of a measuring system 40 (see FIG. 13c) to which the cartridge device 50 is attached before measurement. The measuring system 40 also comprises a control apparatus (not shown) which has been adapted to interact with the cartridge device 50 by electrical and/or mechanical means to control flow of sample liquid 1 (see FIG. 7c) and measurements as well as collect data. Furthermore this apparatus contains mechanical and electronic parts required for measurement, data analysis and user interaction. The present invention is not only suitable for thromboelastometry, thromboeleastography and platelet aggregometry but also for other blood tests usually performed regarding surgery.

A first embodiment of a cartridge device 50 of the invention will be described with reference to FIGS. 4 and 5. The cartridge device 50 for the measuring system 40 for measuring medical relevant, e.g. viscoelastic, characteristics like coagulation or platelet function of a sample liquid 1, particularly a blood sample, comprises a receiving cavity 16 for receiving the sample liquid 1, pump means 18 for pumping the sample liquid, a reagent cavity 19 for storing a reagent 21, a measurement cavity 20 for measuring the sample liquid 1 and a ductwork connecting said cavities. The ductwork comprises an inlet duct 13 from the receiving cavity 16 to the pump means 18, an intermediate duct from the pump means 18 to the reagent cavity 19 and an outlet duct 15 from the reagent cavity 19 to the measurement cavity 20. In a variation said cavities and ducts can be arranged in different ways one of which is shown in FIG. 5, wherein pump means 18 and reagent cavity 19 are changed.

In this embodiment the receiving cavity 16 consists of a cavity within the cartridge device 50. The sample liquid 1 can be applied by means of a syringe, pipette etc, e.g. through a self sealing cap shown as a receiving cavity cover 33a in FIG. 10b. By operating the pump means 18, e.g. by means of the control apparatus mentioned above, the sample liquid is transported to the reagent cavity 19, where the reagent 21 required for measurement is mixed with the sample liquid 1. Further pumping the sample liquid 1 will transfer it into the measurement cavity 20 in which the measurement (described below) is carried out.

In an alternative embodiment the reagent cavity 19 is integral formed with the pump means 18 and/or with the measurement cavity 20 and/or with the ductwork. The transport of the sample liquid 1 can be controlled by said control apparatus.

Figure 6:
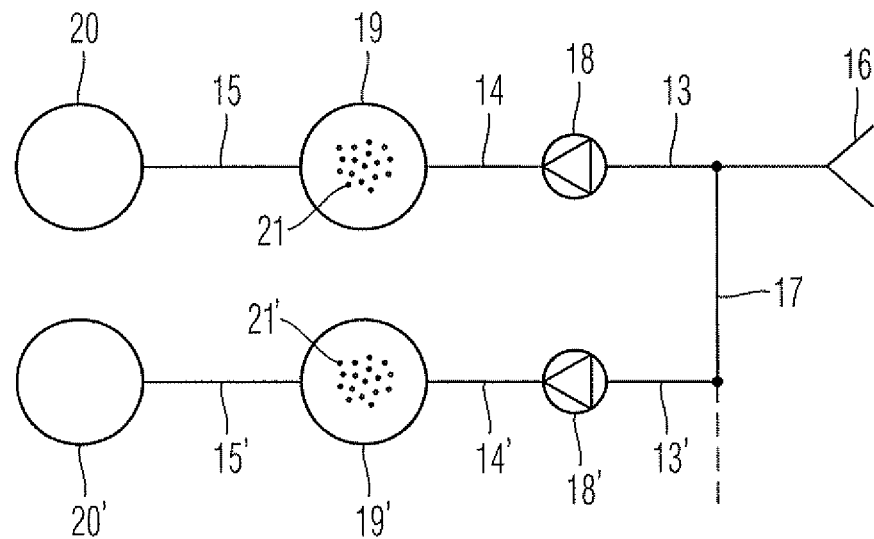
FIG. 6 is a schematic drawing of another variation of the first embodiment of the cartridge device according to the invention.

FIG. 6 shows another variation of the first embodiment. Two arrangements of FIG. 4 with only one receiving cavity 16 are arranged in parallel, wherein a first inlet duct 13 communicates with a second inlet duct 13' connected to second pump means 18'. A second intermediate duct 14' leads to a second reagent cavity 19' storing a second reagent 21'. A second outlet duct 15' connects the second reagent cavity 19' to the second measurement cavity 20'. FIG. 6 shows only one possible variation of a plurality of different arrangements easily imagined. The sample liquid 1 is shared among the arrangements in parallel. Controlled by the external control apparatus the shared portions of the sample liquid 1 are mixed with different reagents 21, 21' during transport. It is apparent to a person skilled in the art that in order to achieve a maximum benefit for a user different types of tests can be combined in one cartridge device 50.

Figure 4:
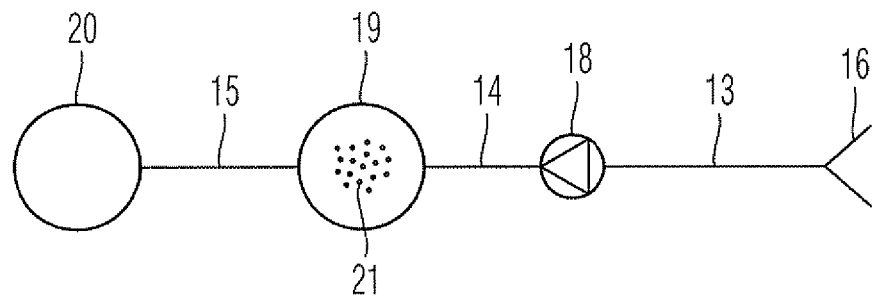
FIG. 4 is a schematic drawing of a first embodiment of a cartridge device according to the invention.
Figure 5:
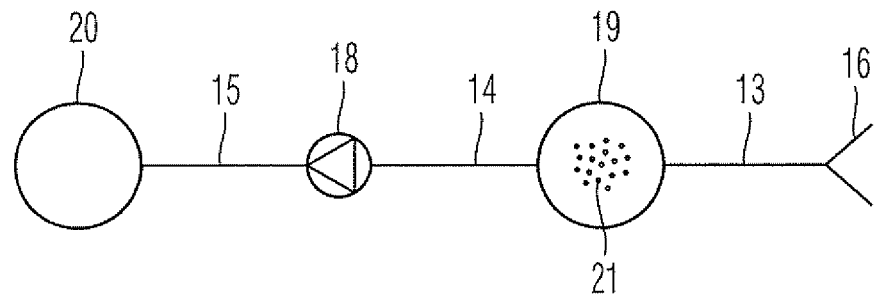
FIG. 5 is a schematic drawing of a variation of the first embodiment of the cartridge device according to the invention.

In a preferred embodiment the cartridge device 50 comprises four arrangements of FIG. 4 or 5 (see FIGS. 16 and 17, respectively) having 4 measurement cavities 20, 20'. Thus measurements can be done with different reagents on the same liquid sample or with same reagents as well to check plausibility.

Regarding e.g. blood coagulation there are different reagents available which activate or suppress different parts of the coagulation cascade. Pentapharm GmbH (Munich, Germany) for example amongst others provide tests for intrinsic and extrinsic activation of a blood sample (INTEM or EXTEM respectively), and also a test for extrinsic activation in which the thrombocyte function is suppressed by administration of cytochalasin D (FIBTEM). It is state of the art that it is possible by wise combination of such tests to be able to determine very precisely at which point within the coagulation cascade a problem occurs. This is of great importance in order to determine a proper medication. By comparison of the results on an EXTEM test of a pathologic sample to those of a FIBTEM test of the same sample it is possible to
e.g. precisely determine if a coagulation disorder results from lack of fibrinogen or a malfunction of platelets. Generally, there are different typical medical scenarios in which coagulation disorders are very likely to occur. For example coagulation disorders occurring during liver transplantation are merely caused by lack of certain coagulation factors etc., while coagulation disorders during open heart surgery are most likely due to the influence of heparin. This means basically that different medical settings require different coagulation tests. Referring to FIG. 6 it is possible and worthwhile to provide different cartridge devices 50 for different typical operations. It is also possible to combine e.g. an INTENT, an EXTEM and a FIBTEM coagulation test with a platelet aggregometry test within one cartridge. Using such a cartridge the preparation of a measurement which provides almost overall information about the coagulation status of a patient merely requires the two steps of attaching the cartridge device 50 to the measuring system 40 with the external control apparatus and injecting the blood sample as one sample liquid 1. Considering the significance of more complex and time consuming preparation of several thromboelastography or thromboelastometry tests, it is evident that the invention is of great advantage for easier, safer and more accurate POC-tests.

It is important to note that the cartridge devices 50 of the described embodiments are suitable for different diagnostic tests like thromboelastometry, thromboelastography, platelet aggregometry and others. Depending on which type of test or tests the cartridge device 50 is designed for, there are different additional parts required which interact with the sample during measurement and/or an external control apparatus. Possible adaptations for thromboelastometry and platelet aggregometry are described below.

Figure 7C:
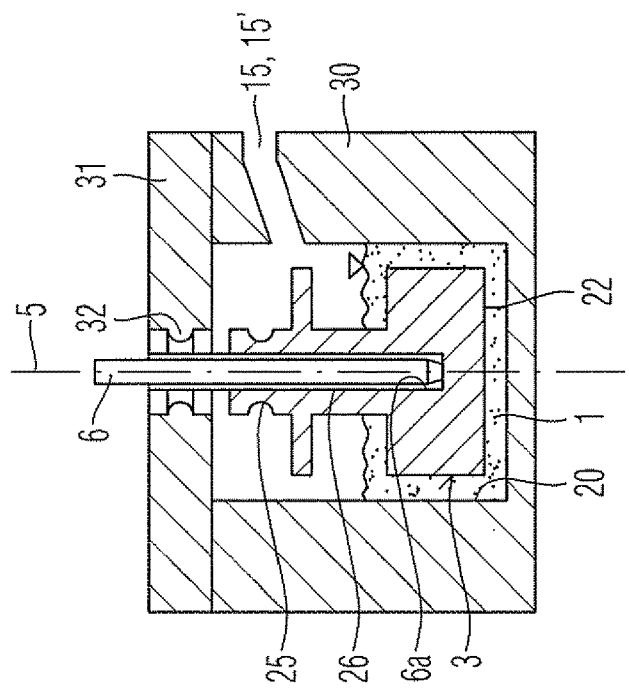
FIG. 7c is a schematic drawing of the first embodiment of the probe element of FIG. 7a within a measuring cavity of the first or the second embodiment of the cartridge device according to the invention in use.
Figure 7B:
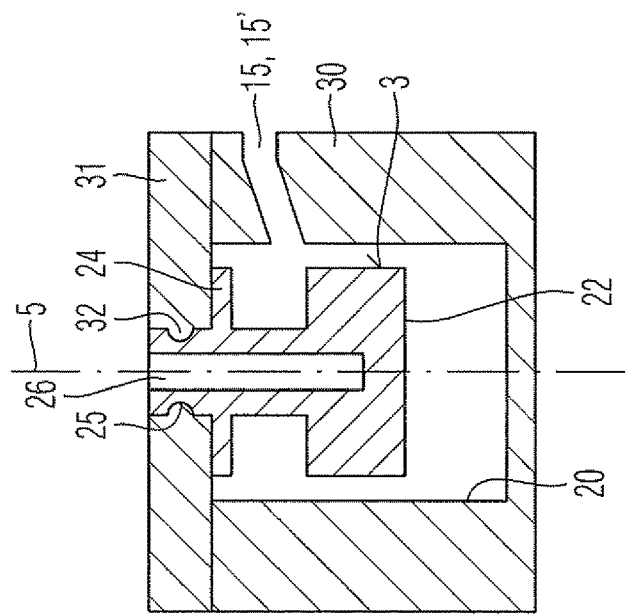
FIG. 7b is a schematic drawing of the first embodiment of the probe element of FIG. 7a within a measuring cavity of the first or a second embodiment of the cartridge device according to the invention before use.
Figure 7A:
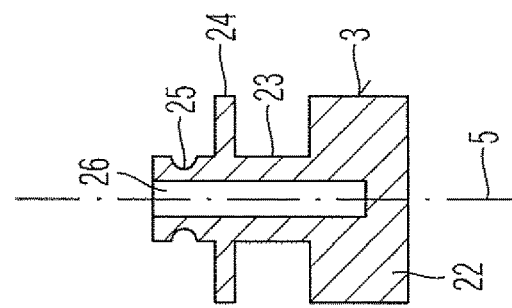
FIG. 7a is a schematic drawing of a first embodiment of a probe element.
Figure 10A:
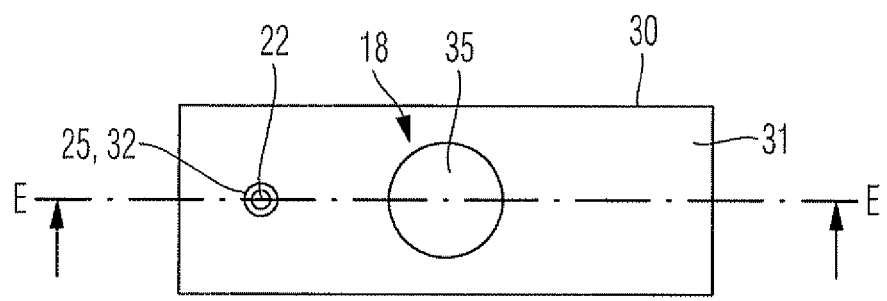
Figure 10B:
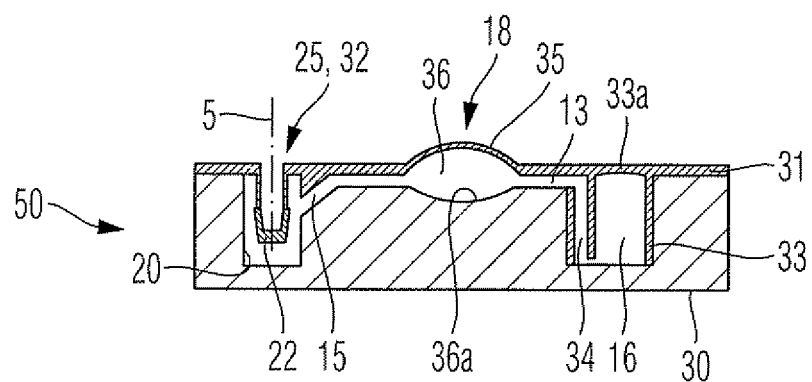
Figure 13A:
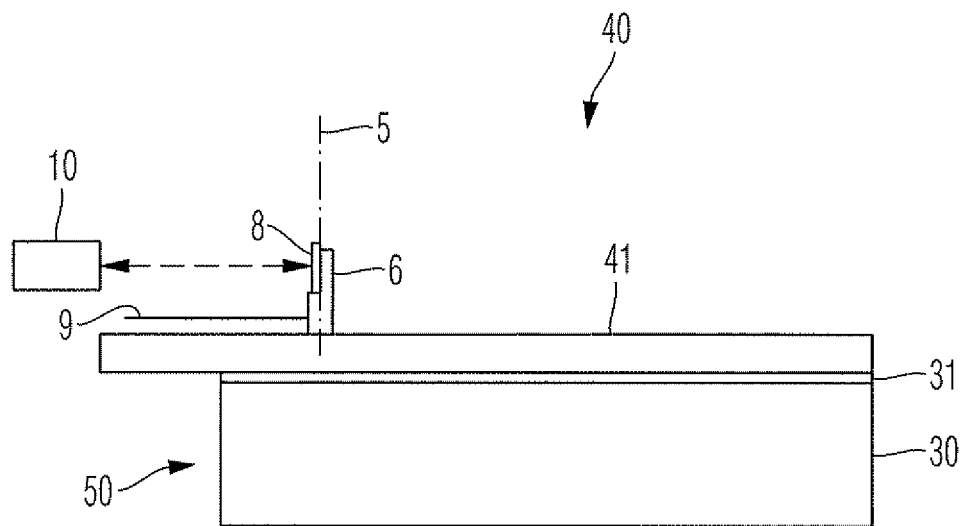
FIG. 13a is a side view of an embodiment of a measuring system according to the invention.
Figure 13B:
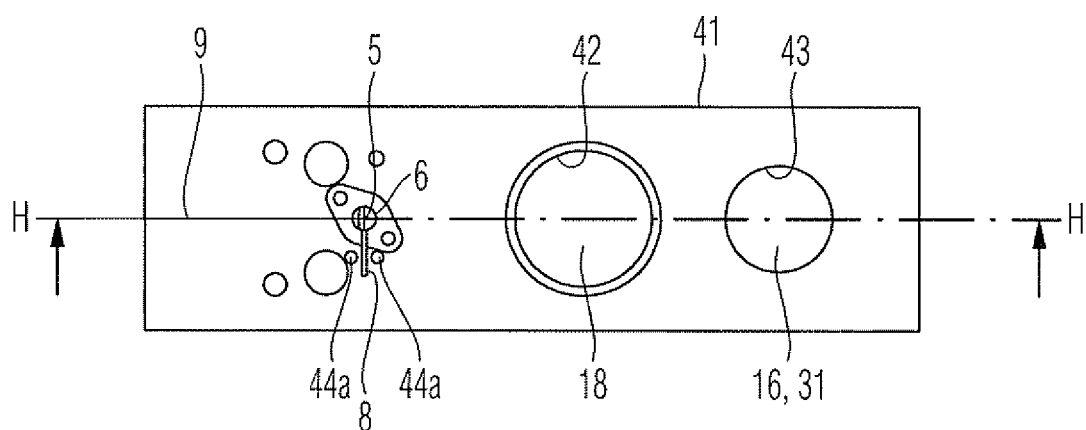
Figure 13C:
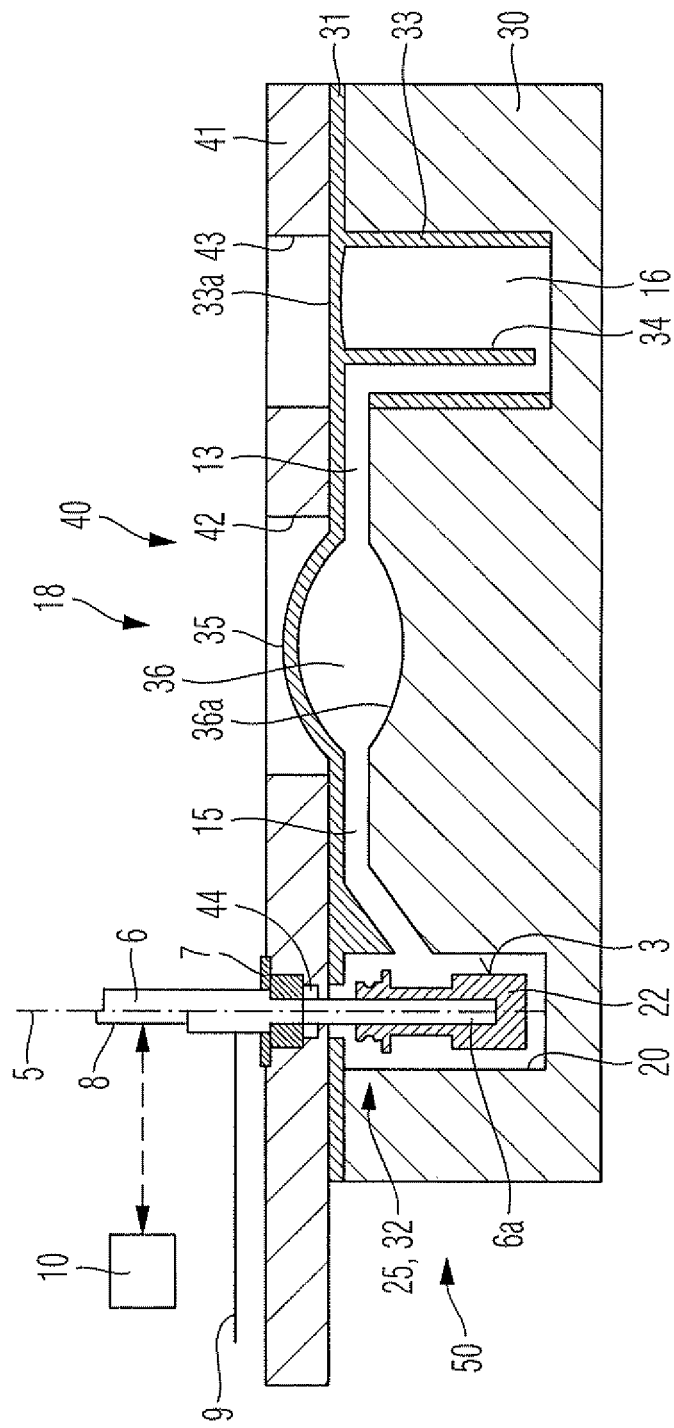
FIG. 13c is a sectional view H-H of the measuring system of FIG. 13b.

FIG. 7a is a schematic drawing of a first embodiment of a probe element 22 arranged in the measurement cavity 20 (see also FIGS. 10b and 13c). FIGS. 7b and 7c show a second embodiment of the cartridge device 50 in form of a cartridge body 30 which comprises only the measurement cavity 20. In the shown example this cavity 20 is accessible via a ductwork 15, 15' through a cavity wall. Alternatively the cavity 20 can be filled through a cover 31, e.g. by injection needles or the like.

Figure 3:
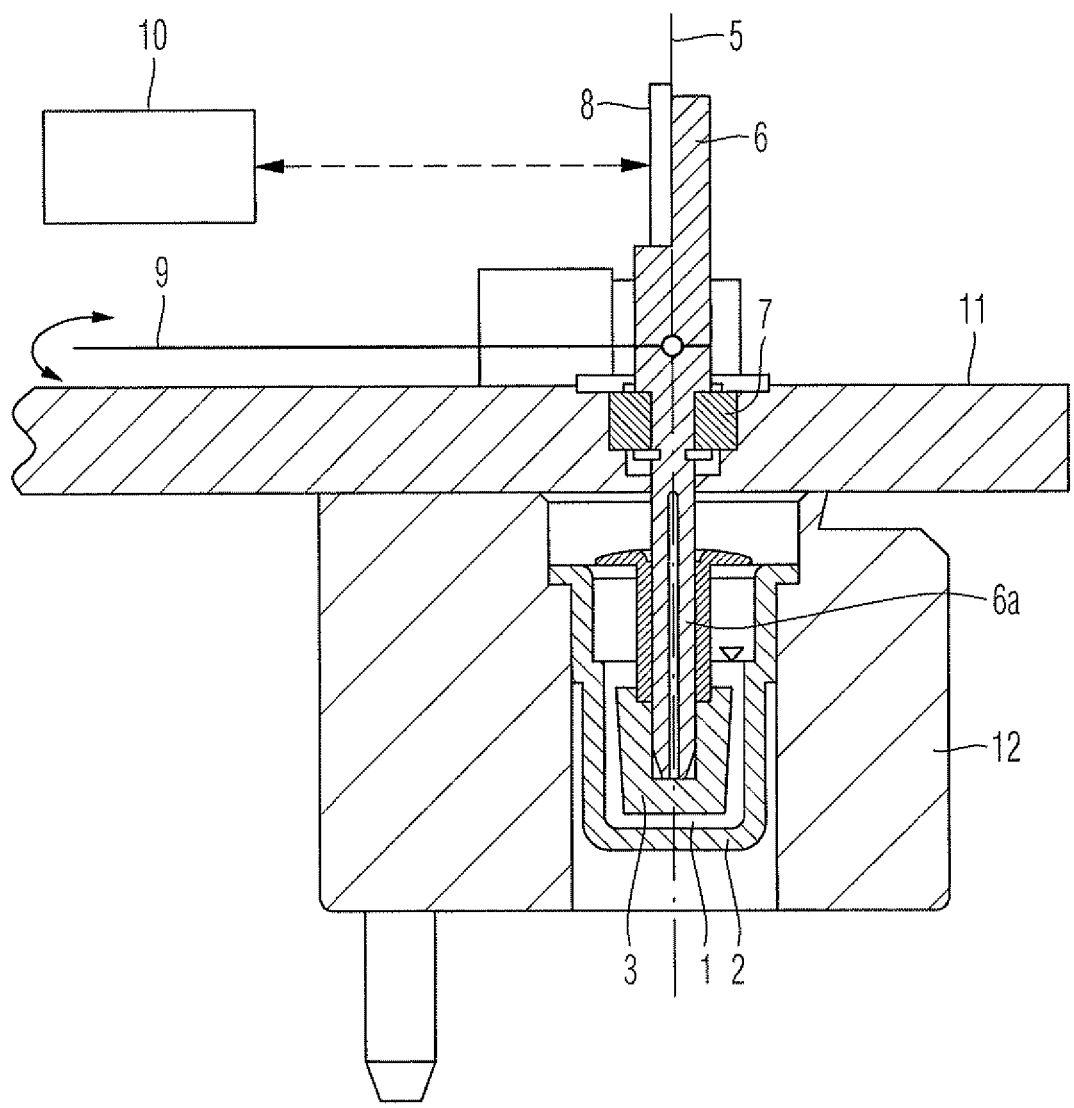
FIG. 3 is a schematic drawing of the thromboelastometry.

The probe element 22 comprises the probe pin 3 (see FIG. 1) which is connected to a flange 24 and a fixing section 25 via an intermediate section 23. The probe element 22 is formed as a rotational part and further comprises a connector section 26 formed as a bore extending within the probe element 22 along its longitudinal axis, which is the rotational axis 5 as well (see FIG. 3).

The probe element 22 is arranged in the measurement cavity 20 of the cartridge body 30 of the cartridge device 50 as shown in FIG. 7b. The measurement cavity 20 is covered by the cover 31 (see also FIGS. 10b and 13c). The cover 31 comprises an opening with fixing means 32 above the measurement cavity 20. The probe element 22 is arranged such that its fixing section 25 corresponding to the fixing means 32 engage with them. In this manner the probe element 22 is detachably fixed to the cover 31, The fixing means 32 in this example are equipped with a circular nose corresponding to a circular notch of the fixing section 25 of the probe element 22. Other fixing means e.g. clip means or the like are possible. The flange 24 is in contact to the inner side of the cover 31.

During attaching the cartridge device 50 to the measuring system 40 (see also FIG. 13c) the shaft 6 of the measuring system 40 (see FIG. 3 and FIGS. 13a . . . c) is inserted with its bottom portion, an insert section 6a, into the connector section 26. By insertion into the connector section 26 of the probe element 22 the probe element 22 will be detached from the cover 31 not before the insert section 6a is completely inserted in the connector section 26. Then the probe element 22 will be put into in a measuring position as shown in FIG. 7c and kept there. The insert section 6a of the shaft 6 is engaged with the connector section 26 of the probe element 22 e.g. by friction, clip means, thread or the Ike. In case of a thread the probe element 22 will be hold by the engagement with or perforation of the cover 31. The shaft 6 having a corresponding thread on its insert section 6a will be inserted into the connector section of the probe element 22 by rotation until the insert section 6a will be completely inserted into the connector section 26. Then the shaft 6 can be pushed down and/or rotated together with the fully engaged probe element 22 until the probe element 22 will be detached from the cover 31. FIG. 7c shows the sample liquid 1,
which has been pumped into the measurement cavity 20. The probe pin 3 of the probe element 22 is immersed in the sample liquid 1. A measurement as described above can be carried out. After the measurement the cartridge device 50 is detached from the measuring system 40, wherein the shaft 6 is drawn up together with the probe element 22 against the cover 31. The insert section 6a of the shaft 6 will be drawn out of the connector section 26 of the probe element 22 the flange 24 thereof contacting and sealing the opening of the cover 31. Instead of a flange 24 the upper end of the probe element 22 can have a larger diameter than the opening in the cover 31. It is preferred that the insert section 6a of the shaft 6 and the measurement cavity 20, 20' are formed symmetrically.

It is also possible to insert the insert section 6a of the shaft 6 into the connector section 26 of the probe element 22 and push the probe element 22 down until its bottom contacts the bottom of the measurement cavity 20, 20' ensuring that the insert section 6a is completely inserted into the connector section 26. Then the shaft 6 will be moved up into the measuring reap. working position of the probe element 22 as shown in FIG. 7c.

Figure 8A:
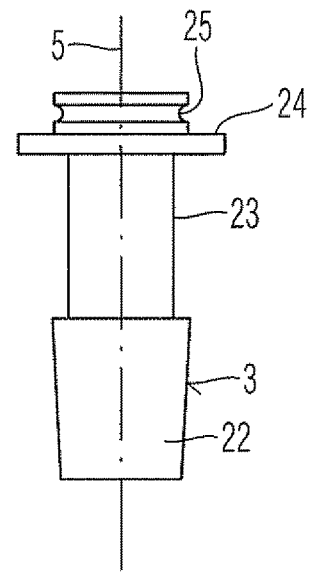
Figure 8B:
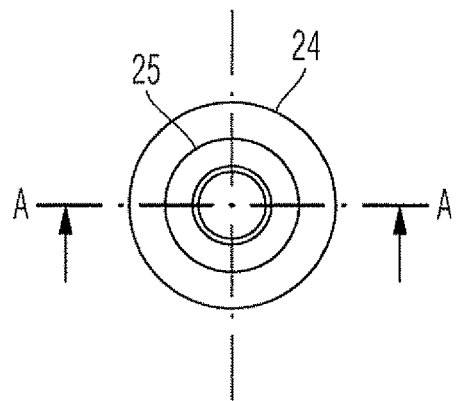
Figure 8C:
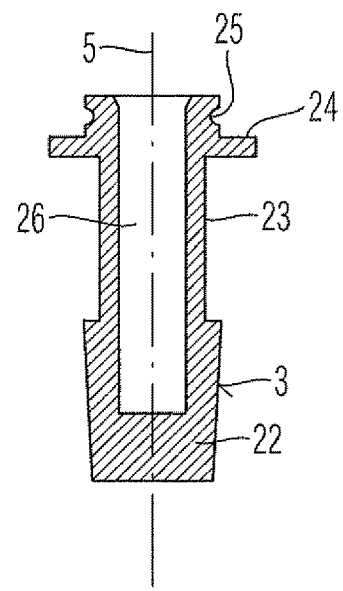

FIGS. 8a . . . c are technical drawings of a preferred embodiment of the probe element 22 of FIG. 7a. FIG. 8a shows a side view and FIG. 8b shows a top view of the probe element 22 parts of which have been described above regarding FIG. 7a. Finally, FIG. 8c illustrates a sectional view along rotational axis 5. The connector section 26 extends over more than about 75% of the length of the probe element 22.

Now a third embodiment of the cartridge device 50 will be described with reference to FIGS. 9a . . . d and FIGS. 10a . . . b.

Figure 9A:
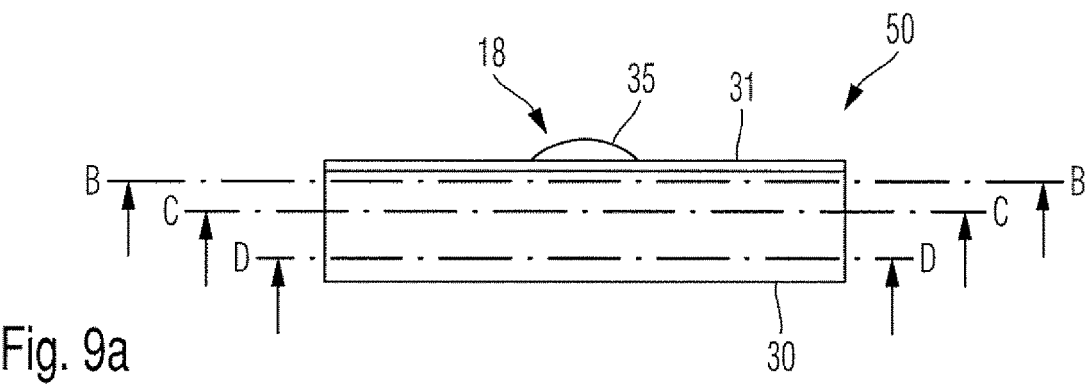
FIG. 9a is a side view of a third embodiment of a cartridge device according to the invention.
Figure 9B:
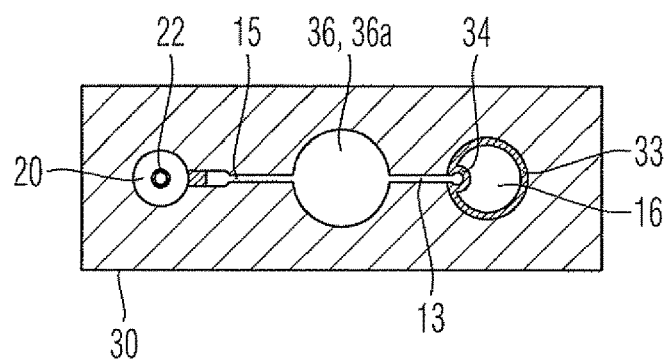
Figure 9C:
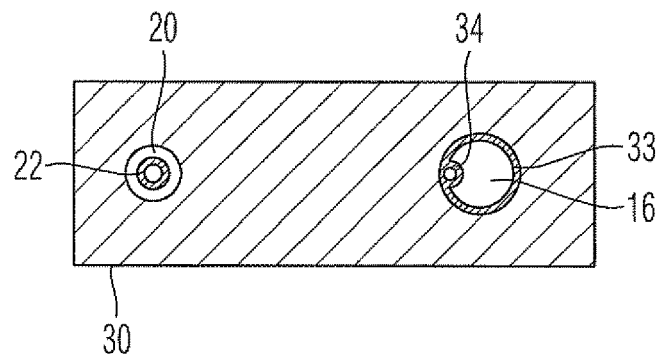
Figure 9D:
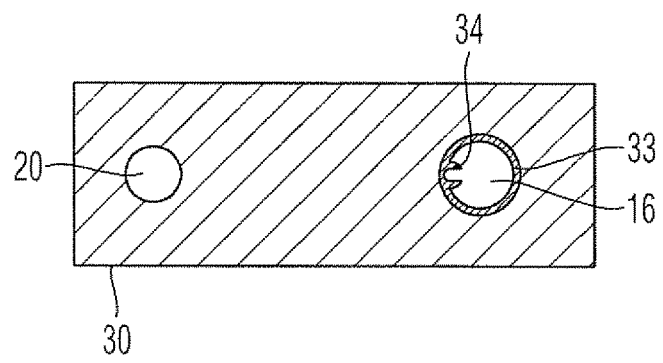

FIG. 9a is a side view of a second embodiment of a third embodiment of the cartridge device 50 according to the invention. FIG. 9b is a sectional view B-B of the cartridge device 50 of FIG. 9a. FIG. 9c is a sectional view C-C of the cartridge device of FIG. 9a. FIG. 9b is a sectional view D-D of the cartridge device of FIG. 9a. FIG. 10a is a top view of the cartridge device of FIG. 9a. FIG. 10b is a sectional view E-E of the cartridge device of FIG. 10a.

The cartridge device 50 of this example is equipped with the ductwork 13 and 15. The ducts are formed with an diameter of approximately 1 mm in this embodiment The ductwork requires that the cartridge device 50 comprises two parts: the cartridge body 30 and the cover 31, which are glued or welded together to obtain a leak-proof device. The cartridge body 30 is relative rigid and the cover 31 is formed as an elastic part. So it is possible to integrate the pump means 18 into the cover 31. Moreover, the cover 31 covers the receiving cavity 16 with the receiving cavity cover 33a and forms a type of liner wall 33 and a separation wall 34 forming an inlet for the inlet duct 13 within the receiving cavity 16. The receiving cavity cover 33a might act as a self seal for injection of a sample liquid 1 by a syringe for example. The cover 31 forms top parts of the ductwork 13 and 15 and a cover of the measurement cavity 20 (see also FIGS. 7b . . . c), In this example the pump means 18 comprises a pump membrane 35 formed by the cover 31. The pump membrane 35 cooperates with a pump cavity 36 formed with a pump cavity bottom 36a in the cartridge body 30 below the pump membrane 35.

In this embodiment a reagent cavity 19, 19' is formed, e.g. by sections of the ductwork or/and the pump means 18, 18' in which the reagents can be stored resp. deposited, especially on the pump cavity bottom 36a, for example.

The pump means 18 will now be described with reference to FIGS. 11a . . . b and FIG. 12.

Figure 11A:
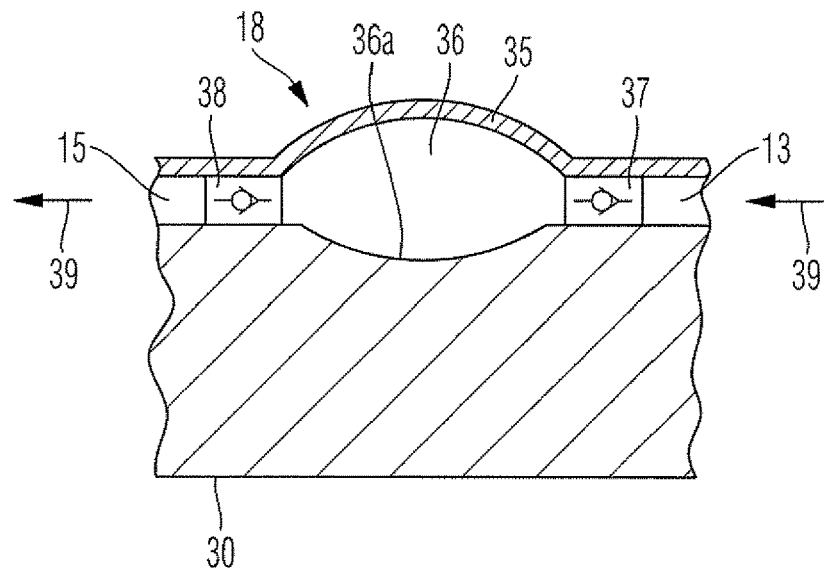
Figure 11B:
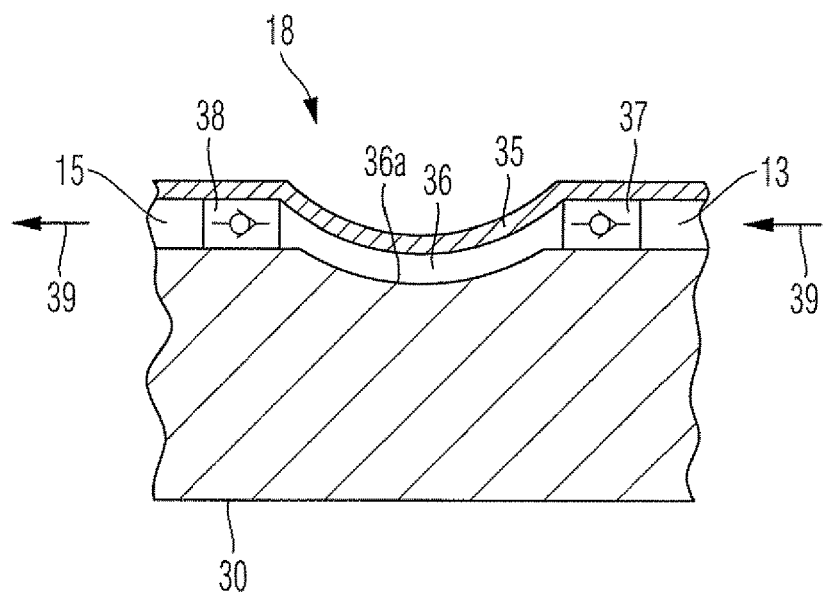
FIG. 11b is a sectional view of the pump means of FIG. 11a in operated position.
Figure 12:
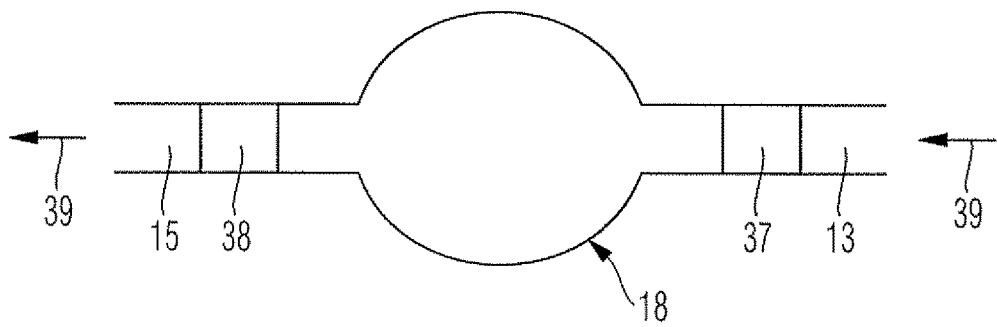

FIG. 11a Is a sectional view of the pump means 18, 18' of the cartridge device 50, FIG. 11b is a sectional view of the pump means 18 of FIG. 11a in operated position, and FIG. 12 is a schematic top view of the pump means 18 of FIG. 11a.

In this example the pump cavity 36 is connected to the inlet duct 13 via an inlet valve 37 and to the outlet valve via an outlet valve 38. Actuation of the pump membrane 35 (shown in FIG. 11b in a working cycle) by an appropriate actuating means (not shown) of the control apparatus the pump means 18 will create a directed flow of the sample liquid 1 in a flow direction 39 depicted by the arrows. The pump membrane 35 being an integrated part of the cover 31 can be made of the cover material or a part made of another material integrally manufactured with the cover 31, e.g. two components manufacturing. The valves 37, 38 can be a type of non-return valve. FIG. 12 shows a top view of the pump means in a schematic way.

An external force exerted on the pump membrane 35 increase the pressure within the pump cavity 36 and opens outlet valve 38 and closes inlet valve 37. Releasing the external force the elastic pump membrane 35 returns into the position shown in FIG. 11a whereby outlet valve 38 will be closed and inlet valve 37 opened to let sample liquid 1 into the pump cavity 36. This mechanism is state of the art according to DE10135569. In context with the present invention the actuation means of the control apparatus activating the pump membrane 35 from outside has the advantage of strict separation between those parts coming into contact with the sample liquid 1 and the control apparatus. At the same time the total number of parts required for the cartridge device 50 being a disposable part as well is kept on a minimum.

Now the measuring system 40 according to the invention is described in an embodiment with reference to FIGS. 13a . . . c.

FIG. 13a is a side view of an embodiment of the measuring system 40, FIG. 13b is a top view of the measuring system 40 of FIG. 13a, and FIG. 13c is a sectional view H-H of the measuring system 40 of FIG. 13b.

The measuring system 40 comprises an interface element 41 to which the cartridge device 50 is attached and fixed. The interface element 41 is shown in FIGS. 13a to 13a in way of example as a base plate. The function of the interface element 41 is to support the shaft 6 and to maintain its position and thus the position of the probe element 22 fixed to the insert section 6a in a measurement position. The interface element 41 can be connected to the whole cover 31 as shown in FIGS. 13a to 13c or only to parts of the cover 31, e.g. surrounding the rotation axis 5. The shaft 6 is rotatable supported in a bearing 7 within a shaft passage 44 (FIG. 13c) and can be rotated around the rotation axis 5 (see also FIG. 3) by driving the spring 9 via driving means (not shown). The detecting means 10 cooperate with the mirror 8 fixed on the shaft 3, also shown in FIG. 3. The control apparatus mentioned above is not shown as well, but easy to imagine. Its actuation and/or operating means can access the pump means 18 through an opening pump access 42 in the interface element 41. The receiving cavity 16 is accessible through another inlet opening 43. These and other different passages or passage ways of the interface element 41 to have access to the cartridge device 50 and/or its cover 31 are illustrated by FIG. 13b as a top view of the measuring system 40 of FIG. 13a. Passage holes 44a are arranged next to the rotational axis 5 to form an access to the cover 31 above the measurement cavity 20, 20', e.g. for injection of liquid sample or reagents. Additional access passage holes can be arranged in the interface element 41, e.g. above the ductwork to access said ductwork.

FIG. 13c illustrates a sectional view H-H of FIG. 13b showing the mounted cartridge device 50 and the measuring system 40. The shaft 6 with its insert section 6a is inserted into the probe element 22 and keeps it in a measurement position as mentioned above. This embodiment comprises only one measurement cavity 20, but it is apparent to a person skilled in the art that modifications and combinations of the invention can be carried out in different ways.

Figure 14:
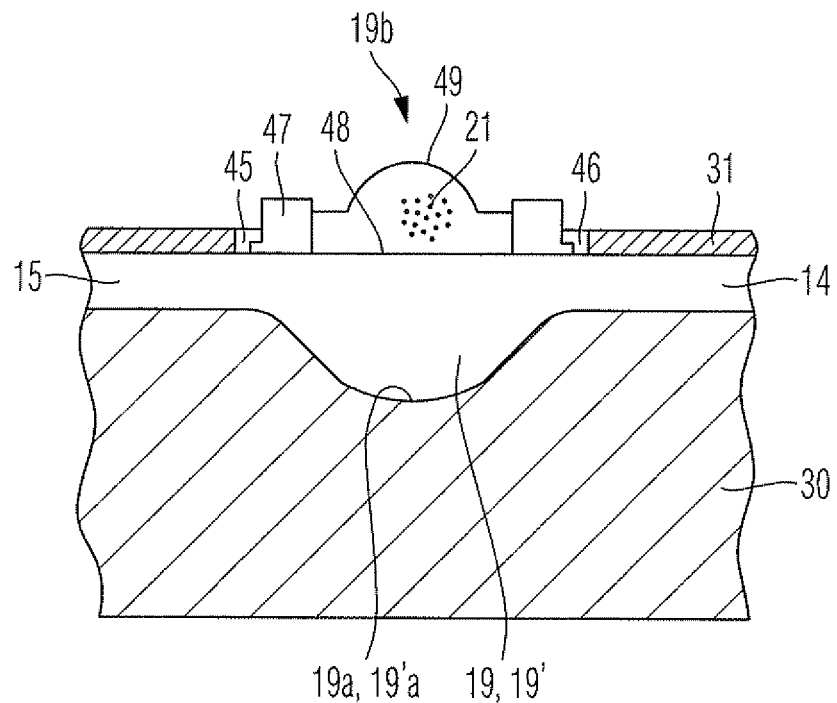
FIG. 14 is a sectional view of a reagent receptacle of a third embodiment of the cartridge device according to the invention.

Thus it is possible to e.g. arrange a reagent receptacle 19b in a blister receptacle e.g. as shown in FIG. 14 which is a sectional view of the reagent receptacle 19b of a third embodiment of the cartridge device 50 according to the invention. The receptacle 19b contains reagent 21 hold within a chamber defined by a blister cover 49, a bottom part 48 and a frame 47 hold in a retaining ring 46 within an reagent cover opening 45 in the cover 31 above the reagent cavity 19, 19' with a reagent cavity bottom 19a, 19a'. Upon exertion of a force by the control apparatus onto the blister cover 49 the bottom part 48 will open and discharge the reagent 21 into the reagent cavity 19, 19'. The receptacle 19b can be fixed to the cover by e.g. clip means as depicted. The frame 47 can be a reinforced ring. The blister cover 49 Is reinforced so that it will not break when a force is exerted on it. Thus the leak-tightness of the cartridge device 50 will be ensured. In this way a unitized construction system can be made, wherein the respective reagents can be easily integrated into the cartridge device 50. It is also advantageous that the reagents can be designed as a small component being cooled reap. transported and supplied easily.

It is also possible to insert reagent receptacles into provided cavities being connected to the ductwork. The reagents can be designed as globules with an appropriate diameter so that they cannot flow through openings into the ductwork before being dissolved by the sample liquid.

Figure 15:
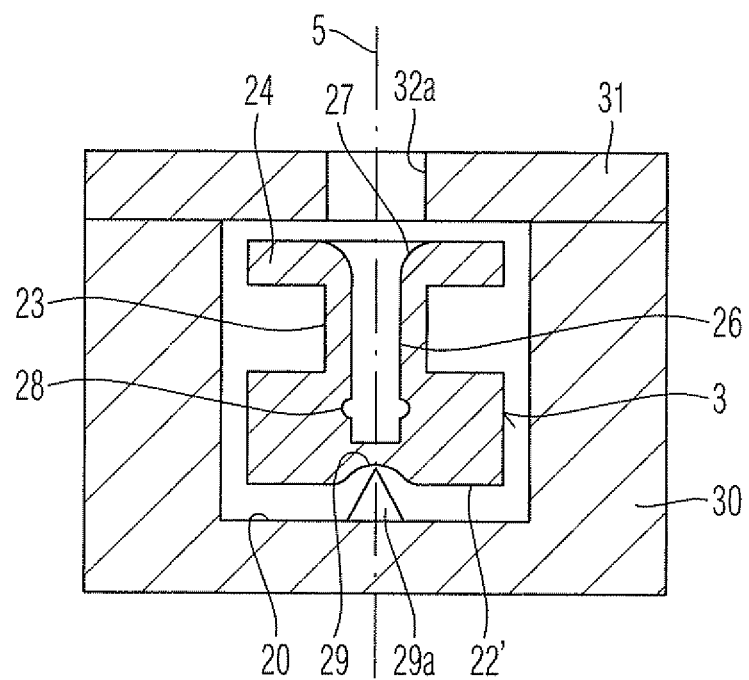
FIG. 15 is a schematic drawing of a second embodiment of the probe element.

FIG. 15 is a schematic drawing of a second embodiment of a probe element 22'. The probe element 22' is arranged in the measurement cavity 20. The probe pin 3 is provided with a dimple 29 at its bottom side. The dimple 29 forms with a nose 29a a toe bearing to support the probe element 22'. The probe element 22' is similar to the probe element 22 of FIG. 7a, but has no fixing section 25, only the flange 24. The connector section 26 comprises a top end formed with an insertion guide 27 for the insertion section 6a of the shaft. The probe element 22' is hold in the measurement cavity 20 in a specific manner so that the insertion section 6a of the shaft 6 can be inserted easily through an opening 32a of the cover 31 which has no fixing means.

The insertion section 6a can engage with a groove 28 inside the connector section 26 of the probe element 22'. After that engagement which is supported by the toe bearing the shaft 6 will be drawn up together with the probe element 22' in the measuring position. It is a matter of fact that other engagement means can be used.

LIST OF REFERENCE NUMERALS

1 Sample liquid
2 Cup
3 Probe pin
4 Torsion wire
5 Rotation axis
6 Shaft
6a Insert section
7 Bearing
8 Mirror
9 Spring
10 Detecting means
11 Base plate
12 Cup holder
13, 13' Inlet duct
14, 14' Intermediate duct
15, 15' Outlet duct
16, 16' Receiving cavity
17 Branch duct
18, 18' Pump means
19, 19' Reagent cavity
19a, 19'a Reagent cavity bottom
19b Reagent receptacle
20, 20' Measurement cavity
21, 21' Reagent
22, 22' Probe element
23 Intermediate section
24 Range
25 Fixing section
26 Connector section
27 Insertion guide
28 Groove
29 Dimple
29a Nose
30 Cartridge body
31 Cover
32 Fixing means
32a Opening
33 Wall
33a Receiving cavity cover
34 Separation wall
35 Pump membrane
36 Pump cavity
36a Pump cavity bottom
37 Inlet valve
38 Outlet valve
39 Flow direction
40 Measuring system
41 Interface element
42 Pump access
43 Inlet opening
44 Shaft passage
44a Passage hole
45 Reagent cover opening
46 Retaining ring
47 Frame
48 Bottom foil
49 Blister cover
50 Cartridge device

The invention claimed is:

1. A cartridge for a measuring system, the cartridge comprising:
    at least two testing cavities, each testing cavity of the at least two testing cavities being configured to perform a respective test to determine a respective viscoelastic characteristic associated with a respective liquid;
    at least two receiving cavities, each receiving cavity of the at least two receiving cavities being configured to receive a respective component used to produce the respective liquid, each receiving cavity being a different structure, and each receiving cavity being empty prior to receiving the respective component used to produce the respective liquid;
    at least two reagent cavities, each reagent cavity of the at least two reagent cavities being configured to hold at least one respective reagent; and
    ductwork that is part of respective fluid flow paths from each respective receiving cavity to and through each respective reagent cavity and subsequently to each respective testing cavity;
    wherein each of the at least two receiving cavities and each of the at least two reagent cavities are different from the ductwork;
    wherein each respective reagent cavity enables mixing the at least one respective reagent with liquid of the respective component to produce the respective liquid; and
    wherein each receiving cavity is associated with a single testing cavity.

2. The cartridge of claim 1, wherein the ductwork is configured so that, in response to pressure, the respective component and the at least one respective reagent mix to form the respective liquid during transport.

3. The cartridge of claim 1, wherein the at least two receiving cavities comprise a first receiving cavity and a second receiving cavity, wherein the at least two testing cavities comprise a first testing cavity and a second testing cavity, and wherein the at least two reagent cavities comprise a first reagent cavity and a second reagent cavity; and
    wherein the ductwork comprises respective first ducts fluidically connected between the first receiving cavity and the first reagent cavity and between the second receiving cavity and the second reagent cavity, and respective second ducts fluidically connected between the first reagent cavity and the first testing cavity and between the second reagent cavity and the second testing cavity so as to create a single first fluid flow path of the respective fluid flow paths from the first receiving cavity through the first reagent cavity to the first testing cavity and a single second fluid flow path of the respective fluid flow paths from the second receiving cavity through the second reagent cavity to the second testing cavity.

4. The cartridge of claim 3, wherein different reagents of the at least one respective reagent are positioned in each of the first reagent cavity and the second reagent cavity such that a reagent in the first reagent cavity is different from a reagent in the second reagent cavity.

5. The cartridge of claim 1, wherein the at least one respective reagent comprises reagent globules configured to dissolve in liquid.

6. A cartridge configured for use by a measuring system to measure viscoelastic characteristics associated with a test sample, the cartridge comprising:
    a first receiving cavity configured to receive a first part of the test sample;
    a second receiving cavity configured to receive a second part of the test sample; the second receiving cavity being different from the first receiving cavity;
    a first reagent cavity configured to hold at least one first reagent for mixing with the first part of the test sample;
    a second reagent cavity configured to hold at least one second reagent for mixing with the second part of the test sample;
    a first testing cavity configured to hold a first liquid that is based on the first part of the test sample and the at least one first reagent, the first testing cavity being configured to enable performance of a first viscoelastic test based on the first liquid in the first testing cavity;
    a second testing cavity configured to hold a second liquid that is based on the second part of the test sample and the at least one second reagent, the second testing cavity being configured to enable performance of a second viscoelastic test based on the second liquid in the second testing cavity;
    first ductwork fluidically connected between the first reagent cavity and the first receiving cavity and between first reagent cavity and the first testing cavity;
    second ductwork fluidically connected between the second reagent cavity and the second receiving cavity and between second reagent cavity and the second testing cavity;
    wherein the first receiving cavity is associated with a single testing cavity which is the first testing cavity, and the first receiving cavity is empty prior to receiving the first part of the test sample; and
    wherein the second receiving cavity is associated with a single testing cavity which is the second testing cavity, and the second receiving cavity is empty prior to receiving the second part of the test sample.

7. The cartridge of claim 6, wherein the at least one first reagent and the at least one second reagent comprise reagent globules configured to dissolve in liquid.

8. The cartridge of claim 6, wherein the at least one first reagent comprises one of:
    a reagent that interacts with the first part of the test sample and that is configured to activate coagulation via an intrinsic pathway;
    a reagent that interacts with the first part of the test sample and that comprises (i) a reagent or a combination of reagents configured to activate coagulation or (ii) a reagent or a combination of reagents configured to suppress thrombocyte contraction; or
    a reagent that interacts with the first part of the test sample and that is configured to activate coagulation via an extrinsic pathway; and
    wherein the at least one second reagent comprises one of:
    a reagent that interacts with the second part of the test sample and that is configured to activate coagulation via an intrinsic pathway;
    a reagent that interacts with the second part of the test sample and that comprises (i) a reagent or a combination of reagents configured to activate coagulation or (ii) a reagent or a combination of reagents configured to suppress thrombocyte contraction; or
    a reagent that interacts with the second part of the test sample and that is configured to activate coagulation via an extrinsic pathway.

9. The cartridge of claim 6, further comprising:
    a first pressure-controlled stop to inhibit entry of the first part of the test sample into the first reagent cavity; and a second pressure-controlled stop to inhibit entry of the second part of the test sample into the second reagent cavity.

10. The cartridge of claim 9, wherein the first pressure-controlled stop comprises a first valve and the second-pressure controlled stop comprise a second valve.

11. The cartridge of claim 6, wherein the first receiving cavity, the first reagent cavity, the first testing cavity, and the first ductwork are along a first fluid flow path; and
wherein the second receiving cavity, the second reagent cavity, the second testing cavity, and the second ductwork are along a second fluid flow path, the first fluid flow path being arranged in parallel to the second fluid flow path.

12. The cartridge of claim 6, wherein a first fluid flow path through the cartridge comprises a single first fluid flow path associated with both the first receiving cavity and the first testing cavity, the first fluid flow path being configured to transport liquids between the first receiving cavity and the first testing cavity; and
wherein a second fluid flow path through the cartridge comprises a single second fluid flow path associated with both the second receiving cavity and the second testing cavity, the second fluid flow path being configured to transport liquids between the second receiving cavity and the second testing cavity.

13. A measuring system comprising the cartridge of claim 6, the measuring system comprising:
a first element arranged relative to the first testing cavity, the first element being configured to measure a viscoelastic characteristic based on the first liquid; and
a second element arranged relative to the second testing cavity, the second element being configured to measure a viscoelastic characteristic based on the second liquid.

14. The measuring system of claim 13, wherein the first element comprises means for measuring the viscoelastic characteristic based on the first liquid; and
wherein the second element comprises means for measuring the viscoelastic characteristic based on the second liquid.

15. A cartridge for a measuring system, the cartridge comprising:
testing cavities comprising at least (i) a first testing cavity configured to hold a first liquid that is based on a mixture of first test sample and at least one first reagent, the first testing cavity being configured to enable a first viscoelastic test based on the first liquid, and (ii) a second testing cavity configured to hold a second liquid that is based on a mixture of second test sample and at least one second reagent, the second testing cavity being configured to enable a second viscoelastic test based on the second liquid, the first viscoelastic test being independent of the second viscoelastic test;
flow paths comprising at least (i) a first flow path configured to transport liquids including transporting the first liquid to the first testing cavity, the first flow path comprising first ductwork, and (ii) a second flow path configured to transport liquids including transporting the second liquid to the second testing cavity, the second flow path comprising second ductwork;
a first reagent cavity along the first flow path, the first reagent cavity containing the at least one first reagent, and the first reagent cavity being configured to receive liquid from the first test sample via the first flow path;
a second reagent cavity along the second flow path, the second reagent cavity containing the at least one second reagent, and the second reagent cavity being configured to receive liquid from the second test sample via the second flow path;
a first receiving cavity configured to receive the first test sample, the first receiving cavity being associated with a single testing cavity which is the first testing cavity and the first receiving cavity being empty prior to receiving the first test sample; and
a second receiving cavity configured to receive the second test sample, the second receiving cavity being associated with a single testing cavity which is the second testing cavity, the second receiving cavity being empty prior to receiving the second test sample, and the second receiving cavity being different from the first receiving cavity.

16. The cartridge of claim 15, wherein the at least one first reagent comprises one of the following:
a reagent that interacts with the first test sample and that is configured to activate coagulation via an intrinsic pathway;
a reagent that interacts with the first test sample and that comprises at least one of (i) a reagent configured to activate coagulation or (ii) a reagent configured to suppress thrombocyte function; or
a reagent that interacts with the first test sample and that is configured to activate coagulation via an extrinsic pathway, and
wherein the at least one second reagent comprises one of the following:
a reagent that interacts with the second test sample and that is configured to activate coagulation via an intrinsic pathway;
a reagent that interacts with the second test sample and that comprises at least one of (i) a reagent configured to activate coagulation or (ii) a reagent configured to suppress thrombocyte function; or
a reagent that interacts with the second test sample and that is configured to activate coagulation via an extrinsic pathway.

17. The cartridge of claim 15, wherein the first receiving cavity is fluidically connected to a single flow path over which the first liquid is transported to the first testing cavity, the single flow path to which the first receiving cavity is fluidically connected being the first flow path; and
wherein the second receiving cavity is fluidically connected to a single flow path over which the second liquid is transported to the second testing cavity, the single flow path to which the second receiving cavity is fluidically connected being the second flow path.

18. The cartridge of claim 15, wherein the first flow path is configured for connection to a pump to implement pressure changes to control flow of fluids along the first flow path using positive and negative pressure.

19. The cartridge of claim 15, further comprising:
a first pressure-controlled stop to control entry of the first test sample from the first ductwork into the first reagent cavity; and
a second pressure-controlled stop to control entry of the second test sample from the second ductwork into the second reagent cavity.

20. The cartridge of claim 15, wherein the first flow path is configured so that, in response to pressure, the first test sample and the at least one first reagent mix to form the first liquid during transport; and wherein the second flow path is configured so that, in response to pressure, the second test sample and the at least one second reagent mix to form the second liquid during transport.

* * * * *